United States Patent
Park et al.

(10) Patent No.: US 11,268,074 B2
(45) Date of Patent: *Mar. 8, 2022

(54) MICROORGANISMS FOR PRODUCING PUTRESCINE OR ORNITHINE AND PROCESS FOR PRODUCING PUTRESCINE OR ORNITHINE USING THEM

(71) Applicant: CJ Cheiljedang Corporation, Seoul (KR)

(72) Inventors: Su Jin Park, Seoul (KR); Young Lyeol Yang, Seoul (KR); Hye Won Um, Gyeonggi-do (KR); Hong Xian Li, Gyeonggi-do (KR); Kyoung Min Lee, Gyeonggi-do (KR); Baek Seok Lee, Seoul (KR); Hyo Hyoung Lee, Incheon (KR); Hee Kyoung Jung, Seoul (KR)

(73) Assignee: CJ Cheiljedang Corporation, Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 16/805,040

(22) Filed: Feb. 28, 2020

(65) Prior Publication Data

US 2020/0190486 A1    Jun. 18, 2020

Related U.S. Application Data

(63) Continuation of application No. 15/746,300, filed as application No. PCT/KR2016/007841 on Jul. 19, 2016, now Pat. No. 10,640,753.

(30) Foreign Application Priority Data

Jul. 20, 2015  (KR) .................. 10-2015-0102624

(51) Int. Cl.
| | | |
|---|---|---|
| *C12N 15/52* | (2006.01) | |
| *C12N 15/00* | (2006.01) | |
| *C12N 9/12* | (2006.01) | |
| *C12N 9/00* | (2006.01) | |
| *C12N 9/10* | (2006.01) | |
| *C12N 9/80* | (2006.01) | |
| *C12P 13/00* | (2006.01) | |
| *C12N 1/00* | (2006.01) | |
| *C12N 9/88* | (2006.01) | |
| *C12P 13/10* | (2006.01) | |

(52) U.S. Cl.
CPC ............. *C12N 9/1029* (2013.01); *C12N 1/00* (2013.01); *C12N 9/1018* (2013.01); *C12N 9/1217* (2013.01); *C12N 9/80* (2013.01); *C12N 9/88* (2013.01); *C12N 9/93* (2013.01); *C12N 15/00* (2013.01); *C12N 15/52* (2013.01); *C12P 13/001* (2013.01); *C12P 13/10* (2013.01); *C12Y 201/03003* (2013.01); *C12Y 203/01001* (2013.01); *C12Y 203/01008* (2013.01); *C12Y 207/02001* (2013.01); *C12Y 305/01016* (2013.01); *C12Y 401/01017* (2013.01); *C12Y 602/01001* (2013.01)

(58) Field of Classification Search
CPC ................................. C12N 15/00; C12N 15/52
USPC .......................................................... 435/195
See application file for complete search history.

(56) References Cited

U.S. PATENT DOCUMENTS

| 8,497,098 B2 | 7/2013 | Eppelmann et al. |
|---|---|---|
| 2012/0214211 A1 | 8/2012 | Bathe et al. |
| 2017/0002386 A1 | 1/2017 | Lee et al. |

FOREIGN PATENT DOCUMENTS

| CN | 1367244 A | 9/2002 |
|---|---|---|
| EP | 0259858 A2 | 3/1988 |
| EP | 1201758 A1 | 5/2002 |
| JP | H0523750 B2 | 4/1993 |
| JP | 2012223091 A | 11/2012 |
| JP | 2013543723 A | 12/2013 |
| KR | 100620092 B1 | 9/2006 |
| KR | 20130082478 A | 7/2013 |
| KR | 101372635 B1 | 3/2014 |
| KR | 20140115244 A | 9/2014 |
| WO | 2006005603 A1 | 1/2006 |
| WO | 2006065095 A1 | 6/2006 |
| WO | 2009096689 A2 | 8/2009 |
| WO | 2009125924 A2 | 10/2009 |
| WO | 2009125992 A2 | 10/2009 |
| WO | 2014148743 A1 | 9/2014 |

OTHER PUBLICATIONS

Dou et al., 2011 "Improvement of L-Arginine Production by Overexpression of a Bifunctional Ornithine Acetyltransferase in Corynebacterium crenatum," Appl Biochem Biotechnol 165:845-855.
Gotoh et al., 2010 "Direct production of L-omithine from casein by commercial digestive enzymes and in situ activated arginase," Bioprocess Biosyst Eng 33:773-777.
Qian et al., 2009 "Metabolic Engineering of *Escherichia coli* for the Production of Putrescine: A Four Carbon Diamine," Biotechnol Bioeng 104(4):651-662.
Schneider et al., 2010 "Putrescine production by engineered Corynebacterium glutamicum," Appl Microbiol Biotechnol 88:859-868.
Schneider et al., 2011 "Biotechnological production of polyamines by Bacteria: recent achievements and future perspectives," Appl Microbiol Biotechnol 91:17-30.

(Continued)

*Primary Examiner* — Sheridan Swope
(74) *Attorney, Agent, or Firm* — Andrea L. C. Reid; Todd K. Macklin; Dechert LLP

(57) ABSTRACT

Disclosed is a modified microorganism producing putrescine or ornithine, and a method for producing putrescine or ornithine using the same.

9 Claims, 2 Drawing Sheets
Specification includes a Sequence Listing.

(56) References Cited

OTHER PUBLICATIONS

Schneider et al., 2012 "Improving putrescine production by Corynebacterium glutamicum by fine-tuning ornithine transcarbamoylase activity using a plasmid addiction system," Appl Microbiol Biotechnol 95:169-179.

International Search Report from related International Application No. PCT/KR2016/007841 dated Nov. 1, 2016 (3 pages).

Genbank Database [Online] (2008) "acetylornithine deacetylase [*Escherichia coli* str. K-12 substr. W3110]," Accession No. BAE77354.1. National Center for Biotechnology Information. Accessible on the Internet at URL: http://www.ncbi.nlm.nih.gov/protein/BAE77354.1 (12 pages).

Jensen et al., 2015 "Modular pathway engineering of Corynebacterium glutamicum for production of the glutamate-derived compounds ornithine, proline, putrescine, citrulline, and arginine," J Biotechnol 214:85-94.

SEQUENCE LISTING

```
<160> NUMBER OF SEQ ID NOS: 39

<210> SEQ ID NO 1
<211> LENGTH: 443
<212> TYPE: PRT
<213> ORGANISM: Escherichia coli
<220> FEATURE:
<221> NAME/KEY: MISC_FEATURE
<223> OTHER INFORMATION: N-acetylglutamate synthase

<400> SEQUENCE: 1

Val Val Lys Glu Arg Lys Thr Glu Leu Val Glu Gly Phe Arg His Ser
1               5                   10                  15

Val Pro Tyr Ile Asn Thr His Arg Gly Lys Thr Phe Val Ile Met Leu
            20                  25                  30

Gly Gly Glu Ala Ile Glu His Glu Asn Phe Ser Ser Ile Val Asn Asp
        35                  40                  45

Ile Gly Leu Leu His Ser Leu Gly Ile Arg Leu Val Val Val Tyr Gly
    50                  55                  60

Ala Arg Pro Gln Ile Asp Ala Asn Leu Ala Ala His His Glu Pro
65                  70                  75                  80

Leu Tyr His Lys Asn Ile Arg Val Thr Asp Ala Lys Thr Leu Glu Leu
                85                  90                  95

Val Lys Gln Ala Ala Gly Thr Leu Gln Leu Asp Ile Thr Ala Arg Leu
            100                 105                 110

Ser Met Ser Leu Asn Asn Thr Pro Leu Gln Gly Ala His Ile Asn Val
        115                 120                 125

Val Ser Gly Asn Phe Ile Ile Ala Gln Pro Leu Gly Val Asp Asp Gly
    130                 135                 140

Val Asp Tyr Cys His Ser Gly Arg Ile Arg Arg Ile Asp Glu Asp Ala
145                 150                 155                 160

Ile His Arg Gln Leu Asp Ser Gly Ala Ile Val Leu Met Gly Pro Val
                165                 170                 175

Ala Val Ser Val Thr Gly Glu Ser Phe Asn Leu Thr Ser Glu Glu Ile
            180                 185                 190

Ala Thr Gln Leu Ala Ile Lys Leu Lys Ala Glu Lys Met Ile Gly Phe
        195                 200                 205

Cys Ser Ser Gln Gly Val Thr Asn Asp Asp Gly Asp Ile Val Ser Glu
    210                 215                 220

Leu Phe Pro Asn Glu Ala Gln Ala Arg Val Glu Ala Gln Glu Glu Lys
225                 230                 235                 240

Gly Asp Tyr Asn Ser Gly Thr Val Arg Phe Leu Arg Gly Ala Val Lys
                245                 250                 255

Ala Cys Arg Ser Gly Val Arg Arg Cys His Leu Ile Ser Tyr Gln Glu
            260                 265                 270

Asp Gly Ala Leu Leu Gln Glu Leu Phe Ser Arg Asp Gly Ile Gly Thr
```

|     |     |     |     | 275 |     |     |     | 280 |     |     |     | 285 |     |     |
| --- | --- | --- | --- | --- | --- | --- | --- | --- | --- | --- | --- | --- | --- | --- |
| Gln | Ile | Val | Met | Glu | Ser | Ala | Glu | Gln | Ile | Arg | Arg | Ala | Thr | Ile | Asn |
|     |     |     |     | 290 |     |     |     |     | 295 |     |     |     |     | 300 |     |

Asp Ile Gly Gly Ile Leu Glu Leu Ile Arg Pro Leu Glu Gln Gln Gly
305                 310                 315                 320

Ile Leu Val Arg Arg Ser Arg Glu Gln Leu Glu Met Glu Ile Asp Lys
                325                 330                 335

Phe Thr Ile Ile Gln Arg Asp Asn Thr Thr Ile Ala Cys Ala Ala Leu
            340                 345                 350

Tyr Pro Phe Pro Glu Glu Lys Ile Gly Glu Met Ala Cys Val Ala Val
        355                 360                 365

His Pro Asp Tyr Arg Ser Ser Arg Gly Glu Val Leu Leu Glu Arg
    370                 375                 380

Ile Ala Ala Gln Ala Lys Gln Ser Gly Leu Ser Lys Leu Phe Val Leu
385                 390                 395                 400

Thr Thr Arg Ser Ile His Trp Phe Gln Glu Arg Gly Phe Thr Pro Val
                405                 410                 415

Asp Ile Asp Leu Leu Pro Glu Ser Lys Lys Gln Leu Tyr Asn Tyr Gln
            420                 425                 430

Arg Lys Ser Lys Val Leu Met Ala Asp Leu Gly
        435                 440

```
<210> SEQ ID NO 2
<211> LENGTH: 1332
<212> TYPE: DNA
<213> ORGANISM: Escherichia coli
<220> FEATURE:
<221> NAME/KEY: misc_feature
<223> OTHER INFORMATION: N-acetylglutamate synthase

<400> SEQUENCE: 2
gtggtaaagg aacgtaaaac cgagttggtc gagggattcc gccattcggt tccctatatc      60
aatacccacc ggggaaaaac gtttgtcatc atgctcggcg gtgaagccat tgagcatgag     120
aatttctcca gtatcgttaa tgatatcggt tgttgcaca gcctcggcat ccgtctggtg      180
gtggtctatg gcgcacgtcc gcagatcgac gcaaatctgg ctgcgcatca ccacgaaccg     240
ctgtatcaca gaatatacg tgtgaccgac gccaaaacac tggaactggt gaagcaggct      300
gcgggaacat tgcaactgga tattactgct cgcctgtcga tgagtctcaa taacacgccg     360
ctgcagggcg cgcatatcaa cgtcgtcagt ggcaattta ttattgccca gccgctgggc      420
gtcgatgacg gcgtggatta ctgccatagc gggcgtatcc ggcggattga tgaagacgcg     480
atccatcgtc aactggacag cggtgcaata gtgctaatgg ggccggtcgc tgtttcagtc     540
actggcgaga gctttaacct gacctcggaa gagattgcca ctcaactggc catcaaactg     600
aaagctgaaa agatgattgg tttttgctct tcccagggcg tcactaatga cgacggtgat     660
attgtctccg aacttttccc taacgaagcg caagcgcggg tagaagccca ggaagagaaa     720
ggcgattaca actccggtac ggtgcgcttt ttgcgtggcg cagtgaaagc ctgccgcagc     780
ggcgtgcgtc gctgtcattt aatcagttat caggaagatg gcgcgctgtt gcaagagttg     840
ttctcacgcg acggtatcgg tacgcagatt gtgatgaaa gcgccgagca gattcgtcgc     900
gcaacaatca cgatattgg cggtattctg gagttgattc gcccactgga gcagcaaggt     960
attctggtac gccgttctcg cgagcagctg gagatgaaa tcgacaaatt caccattatt    1020
cagcgcgata acacgactat tgcctgcgcc gcgctctatc cgttcccgga agagaagatt    1080
```

-continued

```
ggggaaatgg cctgtgtggc agttcacccg gattaccgca gttcatcaag gggtgaagtt   1140
ctgctggaac gcattgccgc tcaggcgaag cagagcggct taagcaaatt gtttgtgctg   1200
accacgcgca gtattcactg gttccaggaa cgtggattta ccccagtgga tattgattta   1260
ctgcccgaga gcaaaaagca gttgtacaac taccagcgta atccaaagt gttgatggcg    1320 gatttagggt aa                                                        1332
```

<210> SEQ ID NO 3
<211> LENGTH: 408
<212> TYPE: PRT
<213> ORGANISM: Escherichia coli
<220> FEATURE:
<221> NAME/KEY: MISC_FEATURE
<223> OTHER INFORMATION: Acetylornithine deacetylase

<400> SEQUENCE: 3

```
Met Asp Lys Leu Leu Glu Arg Phe Leu Asn Tyr Val Ser Leu Asp Thr
  1               5                  10                  15

Gln Ser Lys Ala Gly Val Arg Gln Val Pro Ser Thr Glu Gly Gln Trp
             20                  25                  30

Lys Leu Leu His Leu Leu Lys Glu Gln Leu Glu Glu Met Gly Leu Ile
         35                  40                  45

Asn Val Thr Leu Ser Glu Lys Gly Thr Leu Met Ala Thr Leu Pro Ala
     50                  55                  60

Asn Val Pro Gly Asp Ile Pro Ala Ile Gly Phe Ile Ser His Val Asp
 65                  70                  75                  80

Thr Ser Pro Asp Cys Ser Gly Lys Asn Val Asn Pro Gln Ile Val Glu
                 85                  90                  95

Asn Tyr Arg Gly Gly Asp Ile Ala Leu Gly Ile Gly Asp Glu Val Leu
            100                 105                 110

Ser Pro Val Met Phe Pro Val Leu His Gln Leu Leu Gly Gln Thr Leu
        115                 120                 125

Ile Thr Thr Asp Gly Lys Thr Leu Leu Gly Ala Asp Asp Lys Ala Gly
    130                 135                 140

Ile Ala Glu Ile Met Thr Ala Leu Ala Val Leu Gln Gln Lys Lys Ile
145                 150                 155                 160

Pro His Gly Asp Ile Arg Val Ala Phe Thr Pro Asp Glu Glu Val Gly
                165                 170                 175

Lys Gly Ala Lys His Phe Asp Val Asp Ala Phe Asp Ala Arg Trp Ala
            180                 185                 190

Tyr Thr Val Asp Gly Gly Gly Val Gly Glu Leu Glu Phe Glu Asn Phe
        195                 200                 205

Asn Ala Ala Ser Val Asn Ile Lys Ile Val Gly Asn Asn Val His Pro
    210                 215                 220

Gly Thr Ala Lys Gly Val Met Val Asn Ala Leu Ser Leu Ala Ala Arg
225                 230                 235                 240

Ile His Ala Glu Val Pro Ala Asp Glu Ser Pro Glu Met Thr Glu Gly
                245                 250                 255

Tyr Glu Gly Phe Tyr His Leu Ala Ser Met Lys Gly Thr Val Glu Arg
            260                 265                 270

Ala Asp Met His Tyr Ile Ile Arg Asp Phe Asp Arg Lys Gln Phe Glu
        275                 280                 285

Ala Arg Lys Arg Lys Met Met Glu Ile Ala Lys Lys Val Gly Lys Gly
    290                 295                 300

Leu His Pro Asp Cys Tyr Ile Glu Leu Val Ile Glu Asp Ser Tyr Tyr
```

```
                305                 310                 315                 320
Asn Met Arg Glu Lys Val Val Glu His Pro His Ile Leu Asp Ile Ala
                325                 330                 335
Gln Gln Ala Met Arg Asp Cys Asp Ile Glu Pro Glu Leu Lys Pro Ile
                340                 345                 350
Arg Gly Gly Thr Asp Gly Ala Gln Leu Ser Phe Met Gly Leu Pro Cys
                355                 360                 365
Pro Asn Leu Phe Thr Gly Gly Tyr Asn Tyr His Gly Lys His Glu Phe
                370                 375                 380
Val Thr Leu Glu Gly Met Glu Lys Ala Val Gln Val Ile Val Arg Ile
385                 390                 395                 400
Ala Glu Leu Thr Ala Gln Arg Lys
                405

<210> SEQ ID NO 4
<211> LENGTH: 1227
<212> TYPE: DNA
<213> ORGANISM: Escherichia coli
<220> FEATURE:
<221> NAME/KEY: misc_feature
<223> OTHER INFORMATION: Acetylornithine deacetylase

<400> SEQUENCE: 4
atggataaac tacttgagcg attttttgaac tacgtgtctc tggatacccca atcaaaagca         60 ggggtgagac aggttcccag cacggaaggc caatggaagt tattgcatct gctgaaagag        120
cagctcgaag atgggggct tatcaatgtg accttaagtg agaagggcac tttgatggcg        180
acgttaccgg ctaacgtccc tggcgatatc ccggcgattg gctttattttc tcatgtggat        240 acctcaccgg attgcagcgg caaaaatgtg aatccgcaaa ttgttgaaaa ctatcgcggt        300
ggcgatattg cgctgggtat cggcgatgaa gttttatcac cggttatgtt cccggtgctg        360
catcagctac tgggtcagac gctgattacc accgatggta aaaccttgtt aggtgccgat        420
gacaaagcag gtattgcaga atcatgacc gcgctggcgg tattgcaaca gaaaaaaatt        480
ccgcatggtg atattcgcgt cgccttttacc ccggatgaag aagtgggcaa aggggcgaaa        540
cattttgatg ttgacgcctt cgatgcccgc tgggcttaca ctgttgatgg tggtggcgta        600
ggcgaactgg agttttgaaaa cttcaacgcc gcgtcggtca atatcaaaat tgtcggtaac        660
aatgttcatc cgggcacggc gaaaggagtg atggtaaatg cgctgtcgct ggcggcacgt        720
attcatgcgg aagttccggc ggatgaaagc ccggaaatga cagaaggcta tgaaggtttc        780
tatcatctgg cgagcatgaa aggcaccgtt gaacgggccg atatgcacta catcatccgt        840
gatttcgacc gtaaacagtt tgaagcgcgt aaacgtaaaa tgatggagat cgccaaaaaa        900
gtgggcaaag ggttacatcc tgattgctac attgaactgg tgattgaaga cagttactac        960
aatatgcgcg agaaagtggt tgagcatccg catattctcg atatcgccca gcaggcgatg       1020
cgcgattgcg atattgaacc ggaactgaaa ccgatccgcg gtggtaccga cggcgcgcag       1080
ttgtcgttta tggattacc gtgcccgaac ctgttcactg gcggttacaa ctatcatggt       1140
aagcatgagt ttgtgactct ggaaggtatg gaaaaagcgg tgcaggtgat cgtccgtatt       1200
gccgagttaa cggcgcaacg gaagtaa                                          1227

<210> SEQ ID NO 5
<211> LENGTH: 858
<212> TYPE: PRT
<213> ORGANISM: Corynebacterium glutamicum
<220> FEATURE:
```

<221> NAME/KEY: MISC_FEATURE
<223> OTHER INFORMATION: ATCC 13032 pta-ackA

<400> SEQUENCE: 5

Met Ser Asp Thr Pro Thr Ser Ala Leu Ile Thr Val Asn Arg Ser
1               5                   10                  15

Phe Asp Gly Phe Asp Leu Glu Glu Val Ala Ala Asp Leu Gly Val Arg
                20                  25                  30

Leu Thr Tyr Leu Pro Asp Glu Glu Leu Glu Val Ser Lys Val Leu Ala
            35                  40                  45

Ala Asp Leu Leu Ala Glu Gly Pro Ala Leu Ile Ile Gly Val Gly Asn
50                  55                  60

Thr Phe Phe Asp Ala Gln Val Ala Ala Leu Gly Val Pro Val Leu
65                  70                  75                  80

Leu Leu Val Asp Lys Gln Gly Lys His Val Ala Leu Ala Arg Thr Gln
                85                  90                  95

Val Asn Asn Ala Gly Ala Val Val Ala Ala Phe Thr Ala Glu Gln
            100                 105                 110

Glu Pro Met Pro Asp Lys Leu Arg Lys Ala Val Arg Asn His Ser Asn
            115                 120                 125

Leu Glu Pro Val Met Ser Ala Glu Leu Phe Glu Asn Trp Leu Leu Lys
130                 135                 140

Arg Ala Arg Ala Glu His Ser His Ile Val Leu Pro Glu Gly Asp Asp
145                 150                 155                 160

Asp Arg Ile Leu Met Ala Ala His Gln Leu Leu Asp Gln Asp Ile Cys
                165                 170                 175

Asp Ile Thr Ile Leu Gly Asp Pro Val Lys Ile Lys Glu Arg Ala Thr
            180                 185                 190

Glu Leu Gly Leu His Leu Asn Thr Ala Tyr Leu Val Asn Pro Leu Thr
            195                 200                 205

Asp Pro Arg Leu Glu Glu Phe Ala Glu Gln Phe Ala Glu Leu Arg Lys
210                 215                 220

Ser Lys Ser Val Thr Ile Asp Glu Ala Arg Glu Ile Met Lys Asp Ile
225                 230                 235                 240

Ser Tyr Phe Gly Thr Met Met Val His Asn Gly Asp Ala Asp Gly Met
                245                 250                 255

Val Ser Gly Ala Ala Asn Thr Thr Ala His Thr Ile Lys Pro Ser Phe
            260                 265                 270

Gln Ile Ile Lys Thr Val Pro Glu Ala Ser Val Val Ser Ser Ile Phe
            275                 280                 285

Leu Met Val Leu Arg Gly Arg Leu Trp Ala Phe Gly Asp Cys Ala Val
290                 295                 300

Asn Pro Asn Pro Thr Ala Glu Gln Leu Gly Glu Ile Ala Val Val Ser
305                 310                 315                 320

Ala Lys Thr Ala Ala Gln Phe Gly Ile Asp Pro Arg Val Ala Ile Leu
                325                 330                 335

Ser Tyr Ser Thr Gly Asn Ser Gly Gly Ser Asp Val Asp Arg Ala
            340                 345                 350

Ile Asp Ala Leu Ala Glu Ala Arg Arg Leu Asn Pro Glu Leu Cys Val
            355                 360                 365

Asp Gly Pro Leu Gln Phe Asp Ala Ala Val Asp Pro Gly Val Ala Arg
370                 375                 380

Lys Lys Met Pro Asp Ser Asp Val Ala Gly Gln Ala Asn Val Phe Ile
385                 390                 395                 400

```
Phe Pro Asp Leu Glu Ala Gly Asn Ile Gly Tyr Lys Thr Ala Gln Arg
                405                 410                 415
Thr Gly His Ala Leu Ala Val Gly Pro Ile Leu Gln Gly Leu Asn Lys
            420                 425                 430
Pro Val Asn Asp Leu Ser Arg Gly Ala Thr Val Pro Asp Ile Val Asn
        435                 440                 445
Thr Val Ala Ile Thr Ala Ile Gln Ala Gly Gly Arg Ser Met Ala Leu
    450                 455                 460
Ala Leu Val Leu Asn Ser Gly Ser Ser Ile Lys Phe Gln Leu Val
465                 470                 475                 480
Asn Pro Glu Asn Ser Ala Ile Asp Glu Pro Tyr Val Ser Gly Leu Val
                485                 490                 495
Glu Gln Ile Gly Glu Pro Asn Gly Arg Ile Val Leu Lys Ile Glu Gly
            500                 505                 510
Glu Lys Tyr Thr Leu Glu Thr Pro Ile Ala Asp His Ser Glu Gly Leu
        515                 520                 525
Asn Leu Ala Phe Asp Leu Met Asp Gln His Asn Cys Gly Pro Ser Gln
    530                 535                 540
Leu Glu Ile Thr Ala Val Gly His Arg Val Val His Gly Gly Ile Leu
545                 550                 555                 560
Phe Ser Ala Pro Glu Leu Ile Thr Asp Glu Ile Val Glu Met Ile Arg
                565                 570                 575
Asp Leu Ile Pro Leu Ala Pro Leu His Asn Pro Ala Asn Val Asp Gly
            580                 585                 590
Ile Asp Val Ala Arg Lys Ile Leu Pro Asp Val Pro His Val Ala Val
        595                 600                 605
Phe Asp Thr Gly Phe Phe His Ser Leu Pro Pro Ala Ala Ala Leu Tyr
    610                 615                 620
Ala Ile Asn Lys Asp Val Ala Ala Glu His Gly Ile Arg Arg Tyr Gly
625                 630                 635                 640
Phe His Gly Thr Ser His Glu Phe Val Ser Lys Arg Val Val Glu Ile
                645                 650                 655
Leu Glu Lys Pro Thr Glu Asp Ile Asn Thr Ile Thr Phe His Leu Gly
            660                 665                 670
Asn Gly Ala Ser Met Ala Ala Val Gln Gly Gly Arg Ala Val Asp Thr
        675                 680                 685
Ser Met Gly Met Thr Pro Leu Ala Gly Leu Val Met Gly Thr Arg Ser
    690                 695                 700
Gly Asp Ile Asp Pro Gly Ile Val Phe His Leu Ser Arg Thr Ala Gly
705                 710                 715                 720
Met Ser Ile Asp Glu Ile Asp Asn Leu Leu Asn Lys Lys Ser Gly Val
                725                 730                 735
Lys Gly Leu Ser Gly Val Asn Asp Phe Arg Glu Leu Arg Glu Met Ile
            740                 745                 750
Asp Asn Asn Asp Gln Asp Ala Trp Ser Ala Tyr Asn Ile Tyr Ile His
        755                 760                 765
Gln Leu Arg Arg Tyr Leu Gly Ser Tyr Met Val Ala Leu Gly Arg Val
    770                 775                 780
Asp Thr Ile Val Phe Thr Ala Gly Val Gly Glu Asn Ala Gln Phe Val
785                 790                 795                 800
Arg Glu Asp Ala Leu Ala Gly Leu Glu Met Tyr Gly Ile Glu Ile Asp
                805                 810                 815
```

```
        Pro Glu Arg Asn Ala Leu Pro Asn Asp Gly Pro Arg Leu Ile Ser Thr
                820                 825                 830

Asp Ala Ser Lys Val Lys Val Phe Val Ile Pro Thr Asn Glu Glu Leu
                835                 840                 845

Ala Ile Ala Arg Tyr Ala Val Lys Phe Ala
                850                 855

<210> SEQ ID NO 6
<211> LENGTH: 2579
<212> TYPE: DNA
<213> ORGANISM: Corynebacterium glutamicum
<220> FEATURE:
<221> NAME/KEY: misc_feature
<223> OTHER INFORMATION: ATCC 13032 pta-ackA

<400> SEQUENCE: 6
atgtctgaca caccgacctc agctctgatc accacggtca accgcagctt cgatggattc    60
gatttggaag aagtagcagc agaccttgga gttcggctca cctacctgcc cgacgaagaa   120
ctagaagtat ccaaagttct cgcggcggac ctcctcgctg aggggccagc tctcatcatc   180
ggtgtaggaa acacgttttt cgacgcccag gtcgccgctg ccctcggcgt cccagtgcta   240
ctgctggtag acaagcaagg caagcacgtt gctcttgctc gcacccaggt aaacaatgcc   300
ggcgcagttg ttgcagcagc atttaccgct gaacaagagc caatgccgga taagctgcgc   360
aaggctgtgc gcaaccacag caacctcgaa ccagtcatga cgccgaact ctttgaaaac   420 tggctgctca agcgcgcacg cgcagagcac tcccacattg tgctgccaga aggtgacgac   480
gaccgcatct tgatggctgc ccaccagctg cttgatcaag acatctgtga catcacgatc   540
ctgggcgatc cagtaaagat caaggagcgc gctaccgaac ttggcctgca ccttaacact   600
gcatacctgg tcaatccgct gacagatcct cgcctggagg aattcgccga acaattcgcg   660
gagctgcgca gtcaaagag cgtcactatc gatgaagccc gcgaaatcat gaaggatatt   720
tcctacttcg gcaccatgat ggtccacaac ggcgacgccg acggaatggt atccggtgca   780
gcaaacacca ccgcacacac cattaagcca agcttccaga tcatcaaaac tgttccagaa   840
gcatccgtcg tttcttccat cttcctcatg gtgctgcgcg gcgactgtg ggcattcggc   900 gactgtgctg ttaacccgaa cccaactgct gaacagcttg gtgaaatcgc cgttgtgtca   960
gcaaaaactg cagcacaatt tggcattgat cctcgcgtag ccatcttgtc ctactccact  1020
ggcaactccg gcggaggctc agatgtggat cgcgccatcg acgctcttgc agaagcacgc  1080
cgacttaacc cagaactatg cgtcgatgga ccacttcagt cgacgccgc cgtcgacccg  1140 ggtgtggcgc gcaagaagat gccagactct gacgtcgctg gccaggcaaa tgtgtttatc  1200
ttccctgacc tggaagccgg aaacatcggc tacaaaactg cacaacgcac cggtcacgcc  1260
ctggcagttg gtccgattct gcagggccta acaaaccag tcaacgacct tcccgtggc  1320 gcaacagtcc ctgacatcgt caacacagta gccatcacag caattcaggc aggaggacgc  1380
agctaatggc attggcactt gttttgaact ccggttcatc ttccatcaaa ttccagctgg  1440
tcaaccccga aaactctgcc atcgacgagc catatgtttc tggtcttgtg agcagattg  1500 gtgagccaaa cggccgcatc gtactcaaaa tagagggtga aaaatatacc ctagagacac  1560
ccatcgcaga tcactccgaa ggcctaaacc tggcgttcga tctcatggac agcacaact  1620 gtggtccttc ccaactggaa atcaccgcag ttggacaccg cgtggtccac ggcggaatct  1680
tgttctccgc accggaactt atcactgatg aaatcgtgga aatgatccgc gatctcattc  1740
cactcgcacc actgcacaac cctgcaaacg ttgacggcat tgatgttgct cgaaaaattc  1800
```

```
tccccgatgt cccacacgta gctgtctttg acaccggttt cttccactca cttccaccag    1860
cagctgcgct gtatgccatc aacaaggatg tcgcagctga acacggaatc aggcgctatg    1920
gtttccacgg cacctcccat gaatttgtgt ccaagcgcgt ggtggaaatt ctggaaaagc    1980
ccaccgaaga catcaacacc atcaccttcc acctgggcaa cggcgcatcc atggctgctg    2040
ttcaaggtgg ccgtgcggta gatacttcca tgggtatgac acctctcgcg ggccttgtca    2100
tgggtacccg aagcggtgac attgatccag gtatcgtctt ccacctttcc cgcaccgctg    2160
gcatgagcat cgatgagatc gataatctgc tgaacaaaaa gtcgggtgta aagggacttt    2220
ccggtgttaa tgatttccgt gaactgcggg aaatgatcga caacaatgat caagatgcct    2280
ggtccgcgta caacatttac atacaccaac tccgccgcta cctcggttcc tacatggtgg    2340
cactgggacg ggtagacacc atcgtgttca ccgccggtgt cggtgaaaat gcccagtttg    2400
tccgtgagga tgccttggca ggtttggaaa tgtacggaat tgagatcgat ccagagcgta    2460
acgcattgcc aaacgatggt cctcgattga tttccaccga tgcctccaag gtgaaggtgt    2520 tgttattcc aactaatgaa gagttagcta tcgctaggta cgcggtgaag ttcgcttag     2579
```

<210> SEQ ID NO 7
<211> LENGTH: 858
<212> TYPE: PRT
<213> ORGANISM: Corynebacterium glutamicum
<220> FEATURE:
<221> NAME/KEY: MISC_FEATURE
<223> OTHER INFORMATION: ATCC 13869 pta-ackA

<400> SEQUENCE: 7

```
Met Ser Asp Thr Pro Thr Ser Ala Leu Ile Thr Val Asn Arg Ser
1               5                   10                  15

Phe Asp Gly Phe Asp Leu Glu Glu Val Ala Ala Asp Leu Gly Val Arg
            20                  25                  30

Leu Thr Asp Leu Pro Asp Glu Glu Leu Glu Val Ser Lys Val Leu Ala
        35                  40                  45

Ala Asp Leu Leu Ala Glu Gly Pro Ala Leu Ile Ile Gly Val Gly Asn
    50                  55                  60

Thr Phe Phe Asp Ala Gln Val Ala Ala Leu Gly Val Pro Val Leu
65                  70                  75                  80

Leu Leu Val Asp Lys Gln Gly Lys His Val Ala Leu Ala Arg Thr Gln
                85                  90                  95

Val Asn Asn Ala Gly Ala Val Val Ala Ala Ala Phe Thr Ala Glu Gln
            100                 105                 110

Glu Pro Met Pro Asp Lys Leu Arg Lys Ala Val Arg Asn His Ser Asn
        115                 120                 125

Leu Glu Pro Val Met Ser Ala Glu Leu Phe Glu Asn Trp Leu Leu Lys
    130                 135                 140

Arg Ala Arg Ala Glu His Ser His Ile Val Leu Pro Glu Gly Asp Asp
145                 150                 155                 160

Asp Arg Ile Leu Met Ala Ala His Gln Leu Leu Asp Gln Asp Ile Cys
                165                 170                 175

Asp Ile Thr Ile Leu Gly Asp Pro Val Gln Ile Lys Glu Arg Ala Thr
            180                 185                 190

Glu Leu Gly Leu His Leu Asn Thr Ala Tyr Leu Val Asn Pro Leu Thr
        195                 200                 205

Asp Pro Arg Leu Glu Glu Phe Ala Glu Gln Phe Ala Glu Leu Arg Lys
    210                 215                 220
```

-continued

Ser Lys Ser Val Thr Ile Asp Glu Ala Arg Glu Ile Met Lys Asp Ile
225                 230                 235                 240

Cys Tyr Phe Gly Thr Met Met Val His Asn Gly Asp Ala Asp Gly Met
            245                 250                 255

Val Ser Gly Ala Ala Asn Thr Thr Ala His Thr Ile Lys Pro Ser Phe
            260                 265                 270

Gln Ile Ile Lys Thr Val Pro Glu Ala Ser Val Val Ser Ser Ile Phe
            275                 280                 285

Leu Met Val Leu Arg Gly Arg Leu Trp Ala Phe Gly Asp Cys Ala Val
        290                 295                 300

Asn Pro Asn Pro Thr Ala Glu Gln Leu Gly Ile Ala Val Val Ser
305                 310                 315                 320

Ala Lys Thr Ala Ala Gln Phe Gly Ile Asp Pro Arg Val Ala Ile Leu
                325                 330                 335

Ser Tyr Ser Thr Gly Asn Ser Gly Gly Gly Ser Asp Val Asp Arg Ala
            340                 345                 350

Ile Asp Ala Leu Ala Glu Ala Arg Arg Leu Asn Pro Glu Leu Cys Val
        355                 360                 365

Asp Gly Pro Leu Gln Phe Asp Ala Ala Val Asp Pro Gly Val Ala Arg
    370                 375                 380

Lys Lys Met Pro Asp Ser Asp Val Ala Gly Gln Ala Asn Val Phe Ile
385                 390                 395                 400

Phe Pro Asp Leu Glu Ala Gly Asn Ile Gly Tyr Lys Thr Ala Gln Arg
                405                 410                 415

Thr Gly His Ala Leu Ala Val Gly Pro Ile Leu Gln Gly Leu Asn Lys
            420                 425                 430

Pro Val Asn Asp Leu Ser Arg Gly Ala Thr Val Pro Asp Ile Val Asn
        435                 440                 445

Thr Val Ala Ile Thr Ala Ile Gln Ala Gly Gly Arg Ser Met Ala Leu
    450                 455                 460

Ala Leu Val Leu Asn Ser Gly Ser Ser Ser Ile Lys Phe Gln Leu Val
465                 470                 475                 480

Asn Pro Glu Asn Ser Ala Ile Asp Glu Pro Tyr Val Ser Gly Leu Val
                485                 490                 495

Glu Gln Ile Gly Glu Pro Asn Gly Arg Ile Val Leu Lys Val Glu Gly
            500                 505                 510

Glu Lys Tyr Thr Leu Glu Thr Pro Ile Ala Asp His Ser Glu Gly Leu
        515                 520                 525

Asn Leu Ala Phe Asp Leu Met Asp Gln His Asn Cys Gly Pro Ser Gln
    530                 535                 540

Leu Glu Ile Thr Ala Val Gly His Arg Val Val His Gly Gly Ile Leu
545                 550                 555                 560

Phe Ser Ala Pro Glu Leu Ile Thr Asp Glu Ile Val Glu Met Ile Arg
                565                 570                 575

Asp Leu Ile Pro Leu Ala Pro Leu His Asn Pro Ala Asn Val Asp Gly
            580                 585                 590

Ile Asp Val Ala Arg Lys Ile Leu Pro Asp Val Pro His Val Ala Val
        595                 600                 605

Phe Asp Thr Gly Phe Phe His Ser Leu Pro Pro Ala Ala Ala Leu Tyr
    610                 615                 620

Ala Ile Asn Lys Asp Val Ala Ala Glu His Gly Ile Arg Arg Tyr Gly
625                 630                 635                 640

```
Phe His Gly Thr Ser His Glu Phe Val Ser Lys Arg Val Val Glu Ile
            645                 650                 655

Leu Glu Lys Pro Thr Glu Asp Ile Asn Thr Ile Thr Phe His Leu Gly
        660                 665                 670

Asn Gly Ala Ser Met Ala Ala Val Gln Gly Gly Arg Ala Val Asp Thr
    675                 680                 685

Ser Met Gly Met Thr Pro Leu Ala Gly Leu Val Met Gly Thr Arg Ser
690                 695                 700

Gly Asp Ile Asp Pro Gly Val Val Phe His Leu Ser Arg Thr Ala Gly
705                 710                 715                 720

Met Ser Ile Asp Glu Ile Asp Asn Leu Leu Asn Lys Lys Ser Gly Val
                725                 730                 735

Lys Gly Leu Ser Gly Val Asn Asp Phe Arg Glu Leu Arg Glu Met Ile
            740                 745                 750

Asp Asn Asn Asp Gln Asp Ala Trp Ser Ala Tyr Asn Ile Tyr Ile His
        755                 760                 765

Gln Leu Arg Arg Tyr Leu Gly Ser Tyr Met Val Ala Leu Gly Arg Val
    770                 775                 780

Asp Thr Ile Val Phe Thr Ala Gly Val Gly Glu Asn Ala Gln Phe Val
785                 790                 795                 800

Arg Glu Asp Ala Leu Ala Gly Leu Glu Met Tyr Gly Ile Glu Ile Asp
                805                 810                 815

Pro Glu Arg Asn Ala Leu Pro Asn Asp Gly Pro Arg Leu Ile Ser Thr
            820                 825                 830

Asp Ala Ser Lys Val Lys Val Phe Val Ile Pro Thr Asn Glu Glu Leu
        835                 840                 845

Ala Ile Ala Arg Tyr Ala Val Lys Phe Ala
    850                 855

<210> SEQ ID NO 8
<211> LENGTH: 2579
<212> TYPE: DNA
<213> ORGANISM: Corynebacterium glutamicum
<220> FEATURE:
<221> NAME/KEY: misc_feature
<223> OTHER INFORMATION: ATCC 13869 pta-ackA

<400> SEQUENCE: 8
atgtctgaca caccgacctc agctctgatc accacggtca accgcagctt cgatggattc      60
gatttggaag aagtagcagc agaccttgga gttcggctca ccgacctgcc cgacgaagaa     120
ctagaagtat ccaaagttct cgcggcggac ctcctcgctg aggggccagc tctcatcatc     180
ggtgtaggaa acacgttttt cgacgcccag gtcgccgctg ccctcggcgt cccagtgcta     240
ctgctggtag acaagcaagg caagcacgtt gctcttgctc gcacccaggt aaacaatgcc     300
ggcgcagttg ttgcagcagc atttaccgct gaacaagagc caatgccgga taagctgcgc     360
aaggctgtgc gcaaccacag caacctcgaa ccagtcatga cgccgaact ctttgaaaac     420 tggctgctca gcgcgcacg cgcagagcac tcccacattg tgctgccaga aggtgacgac     480
gaccgcatct tgatggctgc ccaccagctg cttgatcaag acatctgtga catcacgatc     540
ctgggcgatc cagtacagat caaggagcgc gctaccgaac ttggcctgca ccttaacact     600 gcataccctgg tcaatccgct gacagatcct cgcctggagg aattcgccga caattcgcg     660 gagctgcgca gtcaaagag cgtcactatc gatgaagccc gcgaaatcat gaaggatatt     720
tgctacttcg gcaccatgat ggtccacaac ggcgacgccg acggaatggt atccggtgca     780
```

```
gcaaacacca ccgcacacac cattaagcca agcttccaga tcatcaaaac tgttccagaa   840
gcatccgtcg tttcttccat cttcctcatg gtgctgcgcg ggcgactgtg ggcattcggc   900
gactgtgctg ttaacccgaa cccaactgct gaacagcttg gtgaaatcgc cgttgtgtca   960
gcaaaaactg cagcacaatt tggcattgat cctcgcgtag ccatcttgtc ctactccact  1020
ggcaactccg gcggaggctc agatgtggat cgcgccatcg acgctcttgc agaagcacgc  1080
cgactcaacc cagaactatg cgtcgatgga ccacttcagt tcgacgccgc cgtcgacccg  1140
ggtgtggcgc gcaagaagat gccagactct gacgtcgctg gccaggcaaa tgtgtttatc  1200
ttccctgacc tggaagccgg aaacatcggc tacaaaactg cacaacgcac cggtcacgcc  1260
ctggcagttg gtccgattct gcagggcctg aacaaaccag tcaacgacct tcccgtggc   1320 gcaacagtcc ctgacatcgt caacacagta gccatcaccg caattcaggc aggaggacgc  1380
agctaatggc attggcactt gttttgaact ccggttcatc ttccatcaaa ttccagctgg  1440
tcaaccccga aaactctgcc atcgacgagc catatgtttc tggtcttgtg gagcagattg  1500
gtgagccaaa cggccgcatc gtactcaaag tagagggtga aaaatacacc ctagagacac  1560
ccatcgcaga tcactccgaa ggcctaaacc tggcgttcga tctcatggac cagcacaact  1620
gtggtccttc ccaactggaa atcaccgcag ttggacaccg cgtggtccac ggtggaatct  1680
tgttctctgc gccggaactc atcactgatg aaatcgttga atgatccgc gatctcattc   1740 cactcgcacc actgcacaac cctgcaaacg ttgacggcat tgatgttgct cgaaaaattc  1800
tccccgatgt cccacacgta gctgtctttg acaccggttt cttccactca cttccaccag  1860
cagctgcact gtatgccatc aacaaggatg tcgcagctga acacggaatc aggcgctatg  1920
gtttccacgg tacctcccac gaatttgtgt ccaagcgcgt ggtggaaatt ttggaaaagc  1980
ccaccgaaga catcaacacc atcaccttcc acctgggcaa cggcgcatcc atggctgctg  2040
ttcaaggcgg ccgtgcggta gatacttcca tgggtatgac acctctcgcg ggacttgtca  2100
tgggtacccg aagcggtgac attgatccag gtgtcgtttt ccatctctca cgcaccgctg  2160
gcatgagcat cgatgagatc gataatctgc tgaacaaaaa gtcgggtgta agggactttt  2220
ccggagtcaa tgatttccgt gaactgcggg aaatgatcga caacaatgat caagatgcct  2280
ggtccgcgta caacatttac atacaccaac tccgccgcta cctcggttcc tacatggtgg  2340
cactgggacg ggtagacacc atcgtgttca ccgccggtgt tggtgaaaat gcccagtttg  2400
tccgtgagga tgccttggca ggtttggaaa tgtacggcat cgaaatcgat ccggagcgca  2460
acgcactgcc aaacgatggt cctagattga tttccaccga tgcctccaag gtgaaggtgt  2520 tgttattcc aactaatgaa gagttggcta tcgctaggta cgcggtgaag ttcgcttag    2579
```

<210> SEQ ID NO 9
<211> LENGTH: 652
<212> TYPE: PRT
<213> ORGANISM: Escherichia coli
<220> FEATURE:
<221> NAME/KEY: MISC_FEATURE
<223> OTHER INFORMATION: acetyl-CoA synthetase

<400> SEQUENCE: 9

Met Ser Gln Ile His Lys His Thr Ile Pro Ala Asn Ile Ala Asp Arg
1               5                   10                  15

Cys Leu Ile Asn Pro Gln Gln Tyr Glu Ala Met Tyr Gln Gln Ser Ile
            20                  25                  30

Asn Val Pro Asp Thr Phe Trp Gly Glu Gln Gly Lys Ile Leu Asp Trp
        35                  40                  45

```
Ile Lys Pro Tyr Gln Lys Val Lys Asn Thr Ser Phe Ala Pro Gly Asn
    50                  55                  60

Val Ser Ile Lys Trp Tyr Glu Asp Gly Thr Leu Asn Leu Ala Ala Asn
65                  70                  75                  80

Cys Leu Asp Arg His Leu Gln Glu Asn Gly Asp Arg Thr Ala Ile Ile
                85                  90                  95

Trp Glu Gly Asp Asp Ala Ser Gln Ser Lys His Ile Ser Tyr Lys Glu
                100                 105                 110

Leu His Arg Asp Val Cys Arg Phe Ala Asn Thr Leu Leu Glu Leu Gly
            115                 120                 125

Ile Lys Lys Gly Asp Val Val Ala Ile Tyr Met Pro Met Val Pro Glu
    130                 135                 140

Ala Ala Val Ala Met Leu Ala Cys Ala Arg Ile Gly Ala Val His Ser
145                 150                 155                 160

Val Ile Phe Gly Gly Phe Ser Pro Glu Ala Val Ala Gly Arg Ile Ile
                165                 170                 175

Asp Ser Asn Ser Arg Leu Val Ile Thr Ser Asp Glu Gly Val Arg Ala
            180                 185                 190

Gly Arg Ser Ile Pro Leu Lys Lys Asn Val Asp Asp Ala Leu Lys Asn
    195                 200                 205

Pro Asn Val Thr Ser Val Glu His Val Val Leu Lys Arg Thr Gly
    210                 215                 220

Gly Lys Ile Asp Trp Gln Glu Gly Arg Asp Leu Trp Trp His Asp Leu
225                 230                 235                 240

Val Glu Gln Ala Ser Asp Gln His Gln Ala Glu Met Asn Ala Glu
                245                 250                 255

Asp Pro Leu Phe Ile Leu Tyr Thr Ser Gly Ser Thr Gly Lys Pro Lys
                260                 265                 270

Gly Val Leu His Thr Thr Gly Gly Tyr Leu Val Tyr Ala Ala Leu Thr
    275                 280                 285

Phe Lys Tyr Val Phe Asp Tyr His Pro Gly Asp Ile Tyr Trp Cys Thr
    290                 295                 300

Ala Asp Val Gly Trp Val Thr Gly His Ser Tyr Leu Leu Tyr Gly Pro
305                 310                 315                 320

Leu Ala Cys Gly Ala Thr Thr Leu Met Phe Glu Gly Val Pro Asn Trp
                325                 330                 335

Pro Thr Pro Ala Arg Met Ala Gln Val Val Asp Lys His Gln Val Asn
            340                 345                 350

Ile Leu Tyr Thr Ala Pro Thr Ala Ile Arg Ala Leu Met Ala Glu Gly
    355                 360                 365

Asp Lys Ala Ile Glu Gly Thr Asp Arg Ser Ser Leu Arg Ile Leu Gly
    370                 375                 380

Ser Val Gly Glu Pro Ile Asn Pro Glu Ala Trp Glu Trp Tyr Trp Lys
385                 390                 395                 400

Lys Ile Gly Asn Glu Lys Cys Pro Val Val Asp Thr Trp Trp Gln Thr
                405                 410                 415

Glu Thr Gly Gly Phe Met Ile Thr Pro Leu Pro Gly Ala Thr Glu Leu
            420                 425                 430

Lys Ala Gly Ser Ala Thr Arg Pro Phe Phe Gly Val Gln Pro Ala Leu
        435                 440                 445

Val Asp Asn Glu Gly Asn Pro Leu Glu Gly Ala Thr Glu Gly Ser Leu
    450                 455                 460
```

```
Val Ile Thr Asp Ser Trp Pro Gly Gln Ala Arg Thr Leu Phe Gly Asp
465                 470                 475                 480

His Glu Arg Phe Glu Gln Thr Tyr Phe Ser Thr Phe Lys Asn Met Tyr
                485                 490                 495

Phe Ser Gly Asp Gly Ala Arg Arg Asp Glu Asp Gly Tyr Tyr Trp Ile
            500                 505                 510

Thr Gly Arg Val Asp Asp Val Leu Asn Val Ser Gly His Arg Leu Gly
        515                 520                 525

Thr Ala Glu Ile Glu Ser Ala Leu Val Ala His Pro Lys Ile Ala Glu
    530                 535                 540

Ala Ala Val Val Gly Ile Pro His Asn Ile Lys Gly Gln Ala Ile Tyr
545                 550                 555                 560

Ala Tyr Val Thr Leu Asn His Gly Glu Glu Pro Ser Pro Glu Leu Tyr
                565                 570                 575

Ala Glu Val Arg Asn Trp Val Arg Lys Glu Ile Gly Pro Leu Ala Thr
            580                 585                 590

Pro Asp Val Leu His Trp Thr Asp Ser Leu Pro Lys Thr Arg Ser Gly
        595                 600                 605

Lys Ile Met Arg Arg Ile Leu Arg Lys Ile Ala Ala Gly Asp Thr Ser
    610                 615                 620

Asn Leu Gly Asp Thr Ser Thr Leu Ala Asp Pro Gly Val Val Glu Lys
625                 630                 635                 640

Leu Leu Glu Glu Lys Gln Ala Ile Ala Met Pro Ser
                645                 650

<210> SEQ ID NO 10
<211> LENGTH: 1959
<212> TYPE: DNA
<213> ORGANISM: Escherichia coli
<220> FEATURE:
<221> NAME/KEY: misc_feature
<223> OTHER INFORMATION: acetyl-CoA synthetase

<400> SEQUENCE: 10
atgagccaaa ttcacaaaca caccattcct gccaacatcg cagaccgttg cctgataaac      60
cctcagcagt acgaggcgat gtatcaacaa tctattaacg tacctgatac cttctggggc     120
gaacagggaa aaattcttga ctggatcaaa ccttaccaga aggtgaaaaa cacctccttt     180
gcccccggta tgtgtccat taaatggtac gaggacggca cgctgaatct ggcggcaaac     240
tgccttgacc gccatctgca agaaaacggc gatcgtaccg ccatcatctg ggaaggcgac     300
gacgccagcc agagcaaaca tatcagctat aaagagctgc accgcgacgt ctgccgcttc     360
gccaataccc tgctcgagct gggcattaaa aaaggtgatg tggtggcgat ttatatgccg     420
atggtgccgg aagccgcggt tgcgatgctg gcctgcgccc gcattggcgc ggtgcattcg     480
gtgattttcg gcggcttctc gccggaagcc gttgccgggc gcattattga ttccaactca     540
cgactggtga tcacttccga cgaaggtgtg cgtgccgggc gcagtattcc gctgaagaaa     600
aacgttgatg acgcgctgaa aaacccgaac gtcaccagcg tagagcatgt ggtggtactg     660
aagcgtactg gcgggaaaat tgactggcag gaagggcgcg acctgtggtg gcacgacctg     720
gttgagcaag cgagcgatca gcaccaggcg gaagagatga cgccgaaga tccgctgttt     780 attctctaca cctccggttc taccggtaag ccaaaaggtg tgctgcatac taccggcggt     840
tatctggtgt acgcggcgct gacctttaaa tatgtctttg attatcatcc gggtgatatc     900
tactggtgca ccgccgatgt gggctgggtg accggacaca gttacttgct gtacggcccg     960
```

```
ctggcctgcg gtgcgaccac gctgatgttt gaaggcgtac ccaactggcc gacgcctgcc    1020
cgtatggcgc aggtggtgga caagcatcag gtcaatattc tctataccgc acccacggcg    1080
atccgcgcgc tgatggcgga aggcgataaa gcgatcgaag gcaccgaccg ttcgtcgctg    1140
cgcattctcg gttccgtggg cgagccaatt aacccggaag cgtgggagtg gtactggaaa    1200
aaaatcggca acgagaaatg tccggtggtc gatacctggt ggcagaccga accggcggt    1260 ttcatgatca ccccgctgcc tggcgctacc gagctgaaag ccggttcggc aacacgtccg    1320
ttcttcggcg tgcaaccggc gctggtcgat aacgaaggta acccgctgga ggggccacc    1380 gaaggtagcc tggtaatcac cgactcctgg ccgggtcagg cgcgtacgct gtttggcgat    1440
cacgaacgtt ttgaacagac ctacttctcc accttcaaaa atatgtattt cagcggcgac    1500
ggcgcgcgtc gcgatgaaga tggctattac tggataaccg gcgtgtgga cgacgtgctg    1560 aacgtctccg gtcaccgtct ggggacggca gagattgagt cggcgctggt ggcgcatccg    1620
aagattgccg aagccgccgt agtaggtatt ccgcacaata ttaaaggtca ggcgatctac    1680
gcctacgtca cgcttaatca cggggaggaa ccgtcaccag aactgtacgc agaagtccgc    1740
aactgggtgc gtaaagagat tggcccgctg gcgacgccag acgtgctgca ctggaccgac    1800
tccctgccta aaacccgctc cggcaaaatt atgcgccgta ttctgcgcaa aattgcggcg    1860
ggcgatacca gcaacctggg cgatacctcg acgcttgccg atcctggcgt agtcgagaag    1920
ctgcttgaag agaagcaggc tatcgcgatg ccatcgtaa                           1959

<210> SEQ ID NO 11
<211> LENGTH: 37
<212> TYPE: DNA
<213> ORGANISM: Artificial Sequence
<220> FEATURE:
<223> OTHER INFORMATION: PlysC-argA-F

<400> SEQUENCE: 11
gaaaggtgca caaagatggt aaaggaacgt aaaaccg                              37

<210> SEQ ID NO 12
<211> LENGTH: 34
<212> TYPE: DNA
<213> ORGANISM: Artificial Sequence
<220> FEATURE:
<223> OTHER INFORMATION: Tn-argA-RXh

<400> SEQUENCE: 12
gcccactagt ctcgagcatg cggcgttgat tttg                                 34

<210> SEQ ID NO 13
<211> LENGTH: 34
<212> TYPE: DNA
<213> ORGANISM: Artificial Sequence
<220> FEATURE:
<223> OTHER INFORMATION: Tn-PlysC-FXh

<400> SEQUENCE: 13
gaatgagttc ctcgagccga tgctagggcg aaaa                                 34

<210> SEQ ID NO 14
<211> LENGTH: 36
<212> TYPE: DNA
<213> ORGANISM: Artificial Sequence
<220> FEATURE:
<223> OTHER INFORMATION: PlysC-R

<400> SEQUENCE: 14
```
ctttgtgcac ctttcgatct acgtgctgac agttac        36

<210> SEQ ID NO 15
<211> LENGTH: 35
<212> TYPE: DNA
<213> ORGANISM: Artificial Sequence
<220> FEATURE:
<223> OTHER INFORMATION: PlysC-argE-F

<400> SEQUENCE: 15
gaaaggtgca caaagatgaa aaacaaatta ccgcc        35

<210> SEQ ID NO 16
<211> LENGTH: 36
<212> TYPE: DNA
<213> ORGANISM: Artificial Sequence
<220> FEATURE:
<223> OTHER INFORMATION: Tn-argE-RXh

<400> SEQUENCE: 16
gcccactagt ctcgaggttt gagtcactgt cggtcg        36

<210> SEQ ID NO 17
<211> LENGTH: 38
<212> TYPE: DNA
<213> ORGANISM: Artificial Sequence
<220> FEATURE:
<223> OTHER INFORMATION: Pro-pta-FX

<400> SEQUENCE: 17
ccggggatcc tctagagggg ttctaaaaaa tgtggagt        38

<210> SEQ ID NO 18
<211> LENGTH: 43
<212> TYPE: DNA
<213> ORGANISM: Artificial Sequence
<220> FEATURE:
<223> OTHER INFORMATION: pta-PlysC-R

<400> SEQUENCE: 18
gccgtgcttt tcgccctagc atcggacatc gcctttctaa ttt        43

<210> SEQ ID NO 19
<211> LENGTH: 25
<212> TYPE: DNA
<213> ORGANISM: Artificial Sequence
<220> FEATURE:
<223> OTHER INFORMATION: PlysC-F

<400> SEQUENCE: 19
ccgatgctag ggcgaaaagc acggc        25

<210> SEQ ID NO 20
<211> LENGTH: 40
<212> TYPE: DNA
<213> ORGANISM: Artificial Sequence
<220> FEATURE:
<223> OTHER INFORMATION: PlysC-pta-ackA-F

<400> SEQUENCE: 20
gaaaggtgca caaagatgtc tgacacaccg acctcagctc        40

<210> SEQ ID NO 21
<211> LENGTH: 34
<212> TYPE: DNA

<210> SEQ ID NO 21
<211> LENGTH: 34
<212> TYPE: DNA
<213> ORGANISM: Artificial Sequence
<220> FEATURE:
<223> OTHER INFORMATION: Pro-pta-RX

<400> SEQUENCE: 21
gcaggtcgac tctagattat ccggcattgg ctct                              34

<210> SEQ ID NO 22
<211> LENGTH: 18
<212> TYPE: DNA
<213> ORGANISM: Artificial Sequence
<220> FEATURE:
<223> OTHER INFORMATION: Pta-ackA-R

<400> SEQUENCE: 22
tgcagtttca ccccttaa                                                18

<210> SEQ ID NO 23
<211> LENGTH: 43
<212> TYPE: DNA
<213> ORGANISM: Artificial Sequence
<220> FEATURE:
<223> OTHER INFORMATION: 13869_pta-PlysC-R

<400> SEQUENCE: 23
gccgtgcttt tcgccctagc atcggacatc gcctttctag ttt                    43

<210> SEQ ID NO 24
<211> LENGTH: 33
<212> TYPE: DNA
<213> ORGANISM: Artificial Sequence
<220> FEATURE:
<223> OTHER INFORMATION: PlysC-acs-F

<400> SEQUENCE: 24
gaaaggtgca caaagatgag ccaaattcac aaa                               33

<210> SEQ ID NO 25
<211> LENGTH: 36
<212> TYPE: DNA
<213> ORGANISM: Artificial Sequence
<220> FEATURE:
<223> OTHER INFORMATION: Tn-acs-RXh

<400> SEQUENCE: 25
gcccactagt ctcgagaagg cgtttacgcc gcatcc                            36

<210> SEQ ID NO 26
<211> LENGTH: 494
<212> TYPE: PRT
<213> ORGANISM: Corynebacterium glutamicum
<220> FEATURE:
<221> NAME/KEY: MISC_FEATURE
<223> OTHER INFORMATION: ATCC 13032 putrescine exporter

<400> SEQUENCE: 26

Met Thr Ser Glu Thr Leu Gln Ala Gln Ala Pro Thr Lys Thr Gln Arg
1               5                   10                  15

Trp Ala Phe Leu Ala Val Ile Ser Gly Gly Leu Phe Leu Ile Gly Val
            20                  25                  30

Asp Asn Ser Ile Leu Tyr Thr Ala Leu Pro Leu Leu Arg Glu Gln Leu
        35                  40                  45

Ala Ala Thr Glu Thr Gln Ala Leu Trp Ile Ile Asn Ala Tyr Pro Leu
    50                  55                  60

```
Leu Met Ala Gly Leu Leu Gly Thr Gly Thr Leu Gly Asp Lys Ile
 65                  70                  75                  80

Gly His Arg Arg Met Phe Leu Met Gly Leu Ser Ile Phe Gly Ile Ala
                 85                  90                  95

Ser Leu Gly Ala Ala Phe Ala Pro Thr Ala Trp Ala Leu Val Ala Ala
                100                 105                 110

Arg Ala Phe Leu Gly Ile Gly Ala Ala Thr Met Met Pro Ala Thr Leu
                115                 120                 125

Ala Leu Ile Arg Ile Thr Phe Glu Asp Glu Arg Glu Arg Asn Thr Ala
                130                 135                 140

Ile Gly Ile Trp Gly Ser Val Ala Ile Leu Gly Ala Ala Ala Gly Pro
145                 150                 155                 160

Ile Ile Gly Gly Ala Leu Leu Glu Phe Phe Trp Trp Gly Ser Val Phe
                165                 170                 175

Leu Ile Asn Val Pro Val Ala Val Ile Ala Leu Ile Ala Thr Leu Phe
                180                 185                 190

Val Ala Pro Ala Asn Ile Ala Asn Pro Ser Lys His Trp Asp Phe Leu
                195                 200                 205

Ser Ser Phe Tyr Ala Leu Leu Thr Leu Ala Gly Leu Ile Ile Thr Ile
                210                 215                 220

Lys Glu Ser Val Asn Thr Ala Arg His Met Pro Leu Leu Gly Ala
225                 230                 235                 240

Val Ile Met Leu Ile Ile Gly Ala Val Leu Phe Ser Ser Arg Gln Lys
                245                 250                 255

Lys Ile Glu Glu Pro Leu Leu Asp Leu Ser Leu Phe Arg Asn Arg Leu
                260                 265                 270

Phe Leu Gly Gly Val Val Ala Ala Gly Met Ala Met Phe Thr Val Ser
                275                 280                 285

Gly Leu Glu Met Thr Thr Ser Gln Arg Phe Gln Leu Ser Val Gly Phe
                290                 295                 300

Thr Pro Leu Glu Ala Gly Leu Leu Met Ile Pro Ala Ala Leu Gly Ser
305                 310                 315                 320

Phe Pro Met Ser Ile Ile Gly Gly Ala Asn Leu His Arg Trp Gly Phe
                325                 330                 335

Lys Pro Leu Ile Ser Gly Gly Phe Ala Ala Thr Ala Val Gly Ile Ala
                340                 345                 350

Leu Cys Ile Trp Gly Ala Thr His Thr Asp Gly Leu Pro Phe Phe Ile
                355                 360                 365

Ala Gly Leu Phe Phe Met Gly Ala Gly Ala Gly Ser Val Met Ser Val
                370                 375                 380

Ser Ser Thr Ala Ile Ile Gly Ser Ala Pro Val Arg Lys Ala Gly Met
385                 390                 395                 400

Ala Ser Ser Ile Glu Glu Val Ser Tyr Glu Phe Gly Thr Leu Leu Ser
                405                 410                 415

Val Ala Ile Leu Gly Ser Leu Phe Pro Phe Phe Tyr Ser Leu His Ala
                420                 425                 430

Pro Ala Glu Val Ala Asp Asn Phe Ser Ala Gly Val His His Ala Ile
                435                 440                 445

Asp Gly Asp Ala Ala Arg Ala Ser Leu Asp Thr Ala Tyr Ile Asn Val
                450                 455                 460

Leu Ile Ile Ala Leu Val Cys Ala Val Ala Ala Leu Ile Ser Ser
465                 470                 475                 480

Tyr Leu Phe Arg Gly Asn Pro Lys Gly Ala Asn Asn Ala His
```

<210> SEQ ID NO 27
<211> LENGTH: 1485
<212> TYPE: DNA
<213> ORGANISM: Corynebacterium glutamicum
<220> FEATURE:
<221> NAME/KEY: misc_feature
<223> OTHER INFORMATION: ATCC 13032 putrescine exporter

<400> SEQUENCE: 27

```
atgacttcag aaaccttaca ggcgcaagcg cctacgaaaa cccaacgttg ggctttcctc      60
gccgttatca gcggtggtct ctttctgatc ggtgtagaca actcgattct ctacaccgca     120
ctccctctgc tgcgtgaaca gctcgcagcc accgaaaccc aagcgttgtg gatcatcaac     180
gcatatcccc tgctcatggc gggccttctt ttgggtaccg gcactttggg tgacaaaatc     240
ggccaccgcc ggatgttcct catgggcttg agcattttcg gaatcgcttc acttggtgct     300
gcgtttgctc caactgcgtg ggctcttgtt gctgcgagag cttccttgg catcggtgcg      360
gcaacgatga tgcctgcaac cttggctctg atccgcatta cgtttgagga tgagcgtgag     420
cgcaacactg caattggtat ttggggttcc gtggcaattc ttggcgctgc ggcaggcccg     480
atcattggtg gtgcgctgtt ggaattcttc tggtggggtt cggttttcct cattaacgtt     540
ccggtggctt ttatcgcgtt gatcgctacg ctttttgtgg cgccggccaa tatcgcgaat     600
ccgtctaagc attgggattt cttgtcgtcg ttctatgcgc tgctcacact gctgggttg      660
atcatcacga tcaaggaatc tgtgaatact gcacgccata tgcctcttct tttgggtgca     720
gtcatcatgt tgatcattgg tgcggtgttg tttagcagtc gtcagaagaa gatcgaggag     780
ccacttctag atctgtcgtt gttccgtaat cgccttttct taggcggtgt ggttgctgcg     840
ggcatggcga tgtttactgt gtccggtttg gaaatgacta cctcgcagcg tttccagttg     900
tctgtgggtt tcactccact tgaggctggt ttgctcatga tcccagctgc attgggtagc     960
ttcccgatgt ctattatcgg tggtgcaaac ctgcatcgtt ggggcttcaa accgctgatc    1020
agtggtggtt ttgctgccac tgccgttggc atcgccctgt gtatttgggg cgcgactcat    1080
actgatggtt tgccgttttt catcgcgggt ctattcttca tgggcgcggg tgctggttcg    1140
gtaatgtctg tgtcttccac tgcgattatc ggttccgcgc cggtgcgtaa ggctggcatg    1200
gcgtcgtcga tcgaagaggt ctcttatgag ttcggcacgc tgttgtctgt cgcgattttg    1260
ggtagcttgt tcccattctt ctactcgctg catgccccgg cagaggttgc ggataacttc    1320
tcggcgggtg ttcaccacgc gattgatggc gatgcggcgc gtgcatcttt ggacaccgca    1380
tacattaacg tgttgatcat tgccctagta tgcgcagtag cggctgctct gatcagcagt    1440
taccttttcc gcggaaatcc gaagggagcc aataatgcgc actag                    1485
```

<210> SEQ ID NO 28
<211> LENGTH: 494
<212> TYPE: PRT
<213> ORGANISM: Corynebacterium glutamicum
<220> FEATURE:
<221> NAME/KEY: MISC_FEATURE
<223> OTHER INFORMATION: ATCC 13869 putrescine exporter

<400> SEQUENCE: 28

Met Ile Ser Glu Thr Leu Gln Ala Gln Ala Pro Thr Lys Thr Gln Arg
1               5                   10                  15

Trp Ala Phe Leu Ala Val Ile Ser Gly Gly Leu Phe Leu Ile Gly Val
            20                  25                  30

-continued

Asp Asn Ser Ile Leu Tyr Thr Ala Leu Pro Leu Leu Arg Glu Gln Leu
         35                  40                  45

Ala Ala Thr Glu Thr Gln Ala Leu Trp Ile Ile Asn Ala Tyr Pro Leu
 50                  55                  60

Leu Met Ala Gly Leu Leu Leu Gly Thr Gly Thr Leu Gly Asp Lys Ile
 65                  70                  75                  80

Gly His Arg Arg Met Phe Leu Met Gly Leu Ser Ile Phe Gly Ile Ala
                     85                  90                  95

Ser Leu Gly Ala Ala Phe Ala Pro Thr Ala Trp Ala Leu Val Ala Ala
                    100                 105                 110

Arg Ala Phe Leu Gly Ile Gly Ala Ala Thr Met Met Pro Ala Thr Leu
                    115                 120                 125

Ala Leu Ile Arg Ile Thr Phe Glu Asp Glu Arg Glu Arg Asn Thr Ala
130                 135                 140

Ile Gly Ile Trp Gly Ser Val Ala Ile Leu Gly Ala Ala Gly Pro
145                 150                 155             160

Ile Ile Gly Gly Ala Leu Leu Glu Phe Phe Trp Trp Gly Ser Val Phe
                    165                 170                 175

Leu Ile Asn Val Pro Val Ala Val Ile Ala Leu Ile Ala Thr Leu Phe
                    180                 185                 190

Val Ala Pro Ala Asn Ile Ala Asn Pro Ser Lys His Trp Asp Phe Leu
                    195                 200                 205

Ser Ser Phe Tyr Ala Leu Leu Thr Leu Ala Gly Leu Ile Val Thr Ile
                    210                 215                 220

Lys Glu Ser Val Asn Thr Ala Arg His Leu Pro Leu Leu Val Gly Ala
225                 230                 235                 240

Ile Ile Leu Leu Ile Ile Gly Ala Val Leu Phe Ser Ser Arg Gln Lys
                    245                 250                 255

Lys Ile Glu Glu Pro Leu Leu Asp Leu Ser Leu Phe Arg Asn Arg Leu
                    260                 265                 270

Phe Leu Gly Gly Val Val Ala Ala Gly Met Ala Met Phe Thr Val Ser
                    275                 280                 285

Gly Leu Glu Met Thr Thr Ser Gln Arg Phe Gln Leu Ser Val Gly Phe
                    290                 295                 300

Thr Pro Leu Glu Ala Gly Leu Leu Met Ile Pro Ala Ala Leu Gly Ser
305                 310                 315                 320

Phe Pro Met Ser Ile Ile Gly Gly Ala Asn Leu His Arg Trp Gly Phe
                    325                 330                 335

Lys Pro Leu Ile Ser Gly Gly Phe Leu Ala Thr Ala Val Gly Ile Ala
                    340                 345                 350

Leu Cys Ile Trp Gly Ala Thr His Thr Asp Gly Leu Pro Phe Phe Ile
                    355                 360                 365

Ala Gly Leu Phe Phe Met Gly Ala Gly Ala Gly Ser Val Met Ser Val
370                 375                 380

Ser Ser Thr Ala Ile Ile Gly Ser Ala Pro Val Arg Lys Ala Gly Met
385                 390                 395                 400

Ala Ser Ser Ile Glu Glu Val Ser Tyr Glu Phe Gly Thr Leu Leu Ser
                    405                 410                 415

Val Ala Ile Leu Gly Ser Leu Phe Pro Phe Tyr Ser Leu His Ala
                    420                 425                 430

Pro Ala Glu Val Ala Asp Asn Phe Ser Ala Gly Val His His Ala Ile
                    435                 440                 445

Tyr Gly Asp Ala Ala Arg Ala Ser Leu Asp Thr Ala Tyr Ile Asn Val
    450                 455                 460

Leu Ile Ile Ala Leu Val Cys Ala Val Ala Ala Leu Ile Ser Ser
465                 470                 475                 480

Tyr Leu Phe Arg Gly Asn Pro Lys Gly Ala Asn Asn Ala His
                485                 490

<210> SEQ ID NO 29
<211> LENGTH: 1485
<212> TYPE: DNA
<213> ORGANISM: Corynebacterium glutamicum
<220> FEATURE:
<221> NAME/KEY: misc_feature
<223> OTHER INFORMATION: ATCC 13869 putrescine exporter

<400> SEQUENCE: 29

```
atgatttcag aaactttgca ggcgcaagcg cctacgaaaa cccaacgttg ggctttcctc      60
gctgttatca gcggtggtct ctttctgatc ggtgtagaca actcaatcct ctacaccgca     120
ctccccctgc tgcgtgaaca actcgcagcc actgaaaccc aagcgttgtg atcatcaac     180 gcatatcccc tgctcatggc gggtcttctt ttgggtaccg cactttggg tgacaaaatc     240 ggccaccgcc ggatgttcct catgggcttg agcattttcg gaatcgcttc acttggcgct     300
gcgtttgctc caactgcgtg ggctcttgtt gctgcgagag cttttccttgg catcggtgcg     360 gcgacgatga tgcccgcaac cttggctctg atccgcatta cgtttgaaga tgaacgcgaa     420
cggaacaccg cgattggcat ttggggttct gtggcaattc ttggcgcggc ggcaggtccg     480
atcattggtg gtgcgctgtt ggaattcttc tggtgggggtt cggttttcct cattaacgtt     540
ccggtggctg ttatcgcgtt gatcgctacg cttttttgtgg cgccggccaa tatcgcgaat     600
ccgtccaagc actgggattt cttatcctcg ttctatgcat tgcttaccct tgcaggtttg     660
attgtcacca tcaaagaatc ggtaaacact gcacgtcatc tgccactgct tgtaggtgcc     720
atcatcttgc ttatcattgg tcggtgttg tttagcagtc gtcagaagaa gatcgaggag     780
ccacttctag atctgtcgtt gttccgtaat cgccttttct taggcggtgt ggttgctgcg     840
ggcatggcga tgtttactgt gtccggtttg gaaatgacta cctcgcagcg tttccagttg     900
tctgtgggtt tcactccact tgaggctggt ttgctcatga tcccagctgc attgggtagc     960
ttcccgatgt ctattatcgg tggtgcaaac ttgcatcgtt ggggcttcaa accgctgatc    1020
agtggtggtt tccttgccac ggcagtcggc atcgccctgt gtatttgggg cgcgactcat    1080
actgatggtt gccgttttt catcgcgggt ctgttcttca tgggcgcggg tgctggttcg    1140
gtaatgtctg tgtcttccac tgcgattatc ggttccgcgc cggtgcgtaa ggctggcatg    1200
gcgtcgtcga tcgaagaggt ctcttatgag ttcggcacgc tgttgtctgt cgcgattttg    1260
ggtagcttgt tcccattctt ctactcgctg catgccccgg cagaggttgc ggataacttc    1320
tcggcgggtg ttcaccacgc gatttatggc gatgcggcgc gtgcatcttt ggacaccgca    1380
tacattaacg tgttgatcat tgccctagta tgcgcagtag cggctgctct gatcagcagt    1440
taccttttcc gcggaaatcc gaagggagcc aataatgcgc actag                    1485
```

<210> SEQ ID NO 30
<211> LENGTH: 203
<212> TYPE: PRT
<213> ORGANISM: Corynebacterium glutamicum
<220> FEATURE:
<221> NAME/KEY: MISC_FEATURE
<223> OTHER INFORMATION: ATCC 13032 acetyltransferase

<400> SEQUENCE: 30

```
Met Ser Pro Thr Val Leu Pro Ala Thr Gln Ala Asp Phe Pro Lys Ile
1               5                   10                  15

Val Asp Val Leu Val Glu Ala Phe Ala Asn Asp Pro Ala Phe Leu Arg
            20                  25                  30

Trp Ile Pro Gln Pro Asp Pro Gly Ser Ala Lys Leu Arg Ala Leu Phe
        35                  40                  45

Glu Leu Gln Ile Glu Lys Gln Tyr Ala Val Ala Gly Asn Ile Asp Val
    50                  55                  60

Ala Arg Asp Ser Glu Gly Glu Ile Val Gly Val Ala Leu Trp Asp Arg
65                  70                  75                  80

Pro Asp Gly Asn His Ser Ala Lys Asp Gln Ala Ala Met Leu Pro Arg
                85                  90                  95

Leu Val Ser Ile Phe Gly Ile Lys Ala Ala Gln Val Ala Trp Thr Asp
            100                 105                 110

Leu Ser Ser Ala Arg Phe His Pro Lys Phe Pro His Trp Tyr Leu Tyr
        115                 120                 125

Thr Val Ala Thr Ser Ser Ala Arg Gly Thr Gly Val Gly Ser Ala
    130                 135                 140

Leu Leu Asn His Gly Ile Ala Arg Ala Gly Asp Glu Ala Ile Tyr Leu
145                 150                 155                 160

Glu Ala Thr Ser Thr Arg Ala Ala Gln Leu Tyr Asn Arg Leu Gly Phe
                165                 170                 175

Val Pro Leu Gly Tyr Ile Pro Ser Asp Asp Asp Gly Thr Pro Glu Leu
            180                 185                 190

Ala Met Trp Lys Pro Pro Ala Met Pro Thr Val
        195                 200
```

<210> SEQ ID NO 31
<211> LENGTH: 203
<212> TYPE: PRT
<213> ORGANISM: Corynebacterium glutamicum
<220> FEATURE:
<221> NAME/KEY: MISC_FEATURE
<223> OTHER INFORMATION: ATCC 13869 acetyltransferase

<400> SEQUENCE: 31

```
Met Ser Pro Thr Val Leu Pro Ala Thr Gln Ala Asp Phe Pro Lys Ile
1               5                   10                  15

Val Asp Val Leu Val Glu Ala Phe Ala Asn Asp Pro Ala Phe Leu Arg
            20                  25                  30

Trp Ile Pro Gln Pro Asp Pro Gly Ser Ala Lys Leu Arg Ala Leu Phe
        35                  40                  45

Glu Leu Gln Ile Glu Lys Gln Tyr Ala Val Ala Gly Asn Ile Asp Val
    50                  55                  60

Ala Arg Asp Ser Glu Gly Glu Ile Val Gly Val Ala Leu Trp Asp Arg
65                  70                  75                  80

Pro Asp Gly Asn His Ser Ala Lys Asp Gln Ala Ala Ile Leu Pro Arg
                85                  90                  95

Leu Val Ser Ile Phe Gly Ile Lys Ala Ala Gln Val Ala Trp Thr Asp
            100                 105                 110

Leu Ser Ser Ala Arg Phe His Pro Lys Phe Pro His Trp Tyr Leu Tyr
        115                 120                 125

Thr Val Ala Thr Ser Ser Ala Arg Gly Thr Gly Val Gly Ser Ala
    130                 135                 140
```

```
Leu Leu Asn His Gly Ile Ala Arg Ala Gly Asp Glu Ala Ile Tyr Leu
145                 150                 155                 160

Glu Ala Thr Ser Thr Arg Ala Ala Gln Leu Tyr Asn Arg Leu Gly Phe
            165                 170                 175

Val Pro Leu Gly Tyr Ile Pro Ser Asp Asp Gly Thr Pro Glu Leu
        180                 185                 190

Ala Met Trp Lys Pro Pro Ala Met Pro Thr Val
        195                 200

<210> SEQ ID NO 32
<211> LENGTH: 357
<212> TYPE: PRT
<213> ORGANISM: Unknown
<220> FEATURE:
<223> OTHER INFORMATION: Acetyl gamma glutamyl phosphate reductase
      (ArgC)
<220> FEATURE:
<221> NAME/KEY: MISC_FEATURE
<223> OTHER INFORMATION: Acetyl gamma glutamyl phosphate reductase
      (ArgC)

<400> SEQUENCE: 32

Met Ile Met His Asn Val Tyr Gly Val Thr Met Thr Ile Lys Val Ala
1               5                   10                  15

Ile Ala Gly Ala Ser Gly Tyr Ala Gly Gly Glu Ile Leu Arg Leu Leu
            20                  25                  30

Leu Gly His Pro Ala Tyr Ala Ser Gly Glu Leu Glu Ile Gly Ala Leu
        35                  40                  45

Thr Ala Ala Ser Thr Ala Gly Ser Thr Leu Gly Glu Leu Met Pro His
50                  55                  60

Ile Pro Gln Leu Ala Asp Arg Val Ile Gln Asp Thr Thr Ala Glu Thr
65                  70                  75                  80

Leu Ala Gly His Asp Val Val Phe Leu Gly Leu Pro His Gly Phe Ser
                85                  90                  95

Ala Glu Ile Ala Leu Gln Leu Gly Pro Asp Val Thr Val Ile Asp Cys
            100                 105                 110

Ala Ala Asp Phe Arg Leu Gln Asn Ala Ala Asp Trp Glu Lys Phe Tyr
        115                 120                 125

Gly Ser Glu His Gln Gly Thr Trp Pro Tyr Gly Ile Pro Glu Met Pro
130                 135                 140

Gly His Arg Glu Ala Leu Arg Gly Ala Lys Arg Val Ala Val Pro Gly
145                 150                 155                 160

Cys Phe Pro Thr Gly Ala Thr Leu Ala Leu Leu Pro Ala Val Gln Ala
                165                 170                 175

Gly Leu Ile Glu Pro Asp Val Ser Val Val Ser Ile Thr Gly Val Ser
            180                 185                 190

Gly Ala Gly Lys Lys Ala Ser Val Ala Leu Leu Gly Ser Glu Thr Met
        195                 200                 205

Gly Ser Leu Lys Ala Tyr Asn Thr Ser Gly Lys His Arg His Thr Pro
210                 215                 220

Glu Ile Ala Gln Asn Leu Gly Glu Val Ser Asp Lys Pro Val Lys Val
225                 230                 235                 240

Ser Phe Thr Pro Val Leu Ala Pro Leu Pro Arg Gly Ile Leu Thr Thr
                245                 250                 255

Ala Thr Ala Pro Leu Lys Glu Gly Val Thr Ala Glu Gln Ala Arg Ala
            260                 265                 270

Val Tyr Glu Glu Phe Tyr Ala Gln Glu Thr Phe Val His Val Leu Pro
```

```
                275                 280                 285
Glu Gly Ala Gln Pro Gln Thr Gln Ala Val Leu Gly Ser Asn Met Cys
        290                 295                 300
His Val Gln Val Glu Ile Asp Glu Glu Ala Gly Lys Val Leu Val Thr
305                 310                 315                 320
Ser Ala Ile Asp Asn Leu Thr Lys Gly Thr Ala Gly Ala Ala Val Gln
                325                 330                 335
Cys Met Asn Leu Ser Val Gly Phe Asp Glu Ala Ala Gly Leu Pro Gln
        340                 345                 350
Val Gly Val Ala Pro
        355

<210> SEQ ID NO 33
<211> LENGTH: 388
<212> TYPE: PRT
<213> ORGANISM: Unknown
<220> FEATURE:
<223> OTHER INFORMATION: Acetyl glutamate synthase or Ornithine acetyl
      transferase (ArgJ)
<220> FEATURE:
<221> NAME/KEY: MISC_FEATURE
<223> OTHER INFORMATION: Acetyl glutamate synthase or Ornithine acetyl
      transferase (ArgJ)

<400> SEQUENCE: 33

Met Ala Glu Lys Gly Ile Thr Ala Pro Lys Gly Phe Val Ala Ser Ala
1               5                   10                  15
Thr Thr Ala Gly Ile Lys Ala Ser Gly Asn Pro Asp Met Ala Leu Val
            20                  25                  30
Val Asn Gln Gly Pro Glu Phe Ser Ala Ala Val Phe Thr Arg Asn
        35                  40                  45
Arg Val Phe Ala Ala Pro Val Lys Val Ser Arg Glu Asn Val Ala Asp
50                  55                  60
Gly Gln Ile Arg Ala Val Leu Tyr Asn Ala Gly Asn Ala Asn Ala Cys
65                  70                  75                  80
Asn Gly Leu Gln Gly Glu Lys Asp Ala Arg Glu Ser Val Ser His Leu
                85                  90                  95
Ala Gln Asn Leu Gly Leu Glu Asp Ser Asp Ile Gly Val Cys Ser Thr
            100                 105                 110
Gly Leu Ile Gly Glu Leu Leu Pro Met Asp Lys Leu Asn Ala Gly Ile
        115                 120                 125
Asp Gln Leu Thr Ala Glu Gly Ala Leu Gly Asp Asn Gly Ala Ala Ala
130                 135                 140
Ala Lys Ala Ile Met Thr Thr Asp Thr Val Asp Lys Glu Thr Val Val
145                 150                 155                 160
Phe Ala Asp Gly Trp Thr Val Gly Gly Met Gly Lys Gly Val Gly Met
                165                 170                 175
Met Ala Pro Ser Leu Ala Thr Met Leu Val Cys Leu Thr Thr Asp Ala
            180                 185                 190
Ser Val Thr Gln Glu Met Ala Gln Ile Ala Leu Ala Asn Ala Thr Ala
        195                 200                 205
Val Thr Phe Asp Thr Leu Asp Ile Asp Gly Ser Thr Ser Thr Asn Asp
210                 215                 220
Thr Val Phe Leu Leu Ala Ser Gly Ala Ser Gly Ile Thr Pro Thr Gln
225                 230                 235                 240
Asp Glu Leu Asn Asp Ala Val Tyr Ala Ala Cys Ser Asp Ile Ala Ala
                245                 250                 255
```

```
Lys Leu Gln Ala Asp Ala Glu Gly Val Thr Lys Arg Val Ala Val Thr
                260                 265                 270

Val Val Gly Thr Thr Asn Asn Glu Gln Ala Ile Asn Ala Ala Arg Thr
            275                 280                 285

Val Ala Arg Asp Asn Leu Phe Lys Cys Ala Met Phe Gly Ser Asp Pro
        290                 295                 300

Asn Trp Gly Arg Val Leu Ala Ala Val Gly Met Ala Asp Ala Asp Met
305                 310                 315                 320

Glu Pro Glu Lys Ile Ser Val Phe Phe Asn Gly Gln Ala Val Cys Leu
                325                 330                 335

Asp Ser Thr Gly Ala Pro Gly Ala Arg Glu Val Asp Leu Ser Gly Ala
            340                 345                 350

Asp Ile Asp Val Arg Ile Asp Leu Gly Thr Ser Gly Glu Gly Gln Ala
        355                 360                 365

Thr Val Arg Thr Thr Asp Leu Ser Phe Ser Tyr Val Glu Ile Asn Ser
    370                 375                 380

Ala Tyr Ser Ser
385

<210> SEQ ID NO 34
<211> LENGTH: 317
<212> TYPE: PRT
<213> ORGANISM: Unknown
<220> FEATURE:
<223> OTHER INFORMATION: Acetyl glutamate kinase (ArgB)
<220> FEATURE:
<221> NAME/KEY: MISC_FEATURE
<223> OTHER INFORMATION: Acetyl glutamate kinase (ArgB)

<400> SEQUENCE: 34

Met Asn Asp Leu Ile Lys Asp Leu Gly Ser Glu Val Arg Ala Asn Val
1               5                   10                  15

Leu Ala Glu Ala Leu Pro Trp Leu Gln His Phe Arg Asp Lys Ile Val
            20                  25                  30

Val Val Lys Tyr Gly Gly Asn Ala Met Val Asp Asp Asp Leu Lys Ala
        35                  40                  45

Ala Phe Ala Ala Asp Met Val Phe Leu Arg Thr Val Gly Ala Lys Pro
    50                  55                  60

Val Val Val His Gly Gly Gly Pro Gln Ile Ser Glu Met Leu Asn Arg
65                  70                  75                  80

Val Gly Leu Gln Gly Glu Phe Lys Gly Gly Phe Arg Val Thr Thr Pro
                85                  90                  95

Glu Val Met Asp Ile Val Arg Met Val Leu Phe Gly Gln Val Gly Arg
            100                 105                 110

Asp Leu Val Gly Leu Ile Asn Ser His Gly Pro Tyr Ala Val Gly Thr
        115                 120                 125

Ser Gly Glu Asp Ala Gly Leu Phe Thr Ala Gln Lys Arg Met Val Asn
    130                 135                 140

Ile Asp Gly Val Pro Thr Asp Ile Gly Leu Val Gly Asp Ile Ile Asn
145                 150                 155                 160

Val Asp Ala Ser Ser Leu Met Asp Ile Ile Glu Ala Gly Arg Ile Pro
                165                 170                 175

Val Val Ser Thr Ile Ala Pro Gly Glu Asp Gly Gln Ile Tyr Asn Ile
            180                 185                 190

Asn Ala Asp Thr Ala Ala Gly Ala Leu Ala Ala Ala Ile Gly Ala Glu
        195                 200                 205
```

```
Arg Leu Leu Val Leu Thr Asn Val Glu Gly Leu Tyr Thr Asp Trp Pro
        210                 215                 220

Asp Lys Ser Ser Leu Val Ser Lys Ile Lys Ala Thr Glu Leu Glu Ala
225                 230                 235                 240

Ile Leu Pro Gly Leu Asp Ser Gly Met Ile Pro Lys Met Glu Ser Cys
                245                 250                 255

Leu Asn Ala Val Arg Gly Gly Val Ser Ala Ala His Val Ile Asp Gly
            260                 265                 270

Arg Ile Ala His Ser Val Leu Leu Glu Leu Leu Thr Met Gly Gly Ile
        275                 280                 285

Gly Thr Met Val Leu Pro Asp Val Phe Asp Arg Glu Asn Tyr Pro Glu
    290                 295                 300

Gly Thr Val Phe Arg Lys Asp Asp Lys Asp Gly Glu Leu
305                 310                 315
```

<210> SEQ ID NO 35
<211> LENGTH: 391
<212> TYPE: PRT
<213> ORGANISM: Unknown
<220> FEATURE:
<223> OTHER INFORMATION: Acetyl ornithine aminotransferase (ArgD)
<220> FEATURE:
<221> NAME/KEY: MISC_FEATURE
<223> OTHER INFORMATION: Acetyl ornithine aminotransferase (ArgD)

<400> SEQUENCE: 35

```
Met Ser Thr Leu Glu Thr Trp Pro Gln Val Ile Ile Asn Thr Tyr Gly
1               5                   10                  15

Thr Pro Pro Val Glu Leu Val Ser Gly Lys Gly Ala Thr Val Thr Asp
                20                  25                  30

Asp Gln Gly Asn Val Tyr Ile Asp Leu Leu Ala Gly Ile Ala Val Asn
            35                  40                  45

Ala Leu Gly His Ala His Pro Ala Ile Ile Glu Ala Val Thr Asn Gln
        50                  55                  60

Ile Gly Gln Leu Gly His Val Ser Asn Leu Phe Ala Ser Arg Pro Val
65                  70                  75                  80

Val Glu Val Ala Glu Glu Leu Ile Lys Arg Phe Ser Leu Asp Asp Ala
                85                  90                  95

Thr Leu Ala Ala Gln Thr Arg Val Phe Phe Cys Asn Ser Gly Ala Glu
            100                 105                 110

Ala Asn Glu Ala Ala Phe Lys Ile Ala Arg Leu Thr Gly Arg Ser Arg
        115                 120                 125

Ile Leu Ala Ala Val His Gly Phe His Gly Arg Thr Met Gly Ser Leu
130                 135                 140

Ala Leu Thr Gly Gln Pro Asp Lys Arg Glu Ala Phe Leu Pro Met Pro
145                 150                 155                 160

Ser Gly Val Glu Phe Tyr Pro Tyr Gly Asp Thr Asp Tyr Leu Arg Lys
                165                 170                 175

Met Val Glu Thr Asn Pro Thr Asp Val Ala Ala Ile Phe Leu Glu Pro
            180                 185                 190

Ile Gln Gly Glu Thr Gly Val Val Pro Ala Pro Glu Gly Phe Leu Lys
        195                 200                 205

Ala Val Arg Glu Leu Cys Asp Glu Tyr Gly Ile Leu Met Ile Thr Asp
210                 215                 220

Glu Val Gln Thr Gly Val Gly Arg Thr Gly Asp Phe Phe Ala His Gln
225                 230                 235                 240
```

```
His Asp Gly Val Val Pro Asp Val Val Thr Met Ala Lys Gly Leu Gly
            245                 250                 255

Gly Gly Leu Pro Ile Gly Ala Cys Leu Ala Thr Gly Arg Ala Ala Glu
        260                 265                 270

Leu Met Thr Pro Gly Lys His Gly Thr Thr Phe Gly Gly Asn Pro Val
            275                 280                 285

Ala Cys Ala Ala Ala Lys Ala Val Leu Ser Val Val Asp Asp Ala Phe
        290                 295                 300

Cys Ala Glu Val Ala Arg Lys Gly Glu Leu Phe Lys Glu Leu Leu Ala
305                 310                 315                 320

Lys Val Asp Gly Val Asp Val Arg Gly Arg Gly Leu Met Leu Gly
            325                 330                 335

Val Val Leu Glu Arg Asp Val Ala Lys Gln Ala Val Leu Asp Gly Phe
        340                 345                 350

Lys His Gly Val Ile Leu Asn Ala Pro Ala Asp Asn Ile Ile Arg Leu
        355                 360                 365

Thr Pro Pro Leu Val Ile Thr Asp Glu Glu Ile Ala Asp Ala Val Lys
    370                 375                 380

Ala Ile Ala Glu Thr Ile Ala
385                 390

<210> SEQ ID NO 36
<211> LENGTH: 319
<212> TYPE: PRT
<213> ORGANISM: Unknown
<220> FEATURE:
<223> OTHER INFORMATION: Ornithine carbamoyl transferase (argF)
<220> FEATURE:
<221> NAME/KEY: MISC_FEATURE
<223> OTHER INFORMATION: Ornithine carbamoyl transferase (argF)

<400> SEQUENCE: 36

Met Thr Ser Gln Pro Gln Val Arg His Phe Leu Ala Asp Asp Leu
1               5                   10                  15

Thr Pro Ala Glu Gln Ala Glu Val Leu Thr Leu Ala Ala Lys Leu Lys
            20                  25                  30

Ala Ala Pro Phe Ser Glu Arg Pro Leu Glu Gly Pro Lys Ser Val Ala
        35                  40                  45

Val Leu Phe Asp Lys Thr Ser Thr Arg Thr Arg Phe Ser Phe Asp Ala
    50                  55                  60

Gly Ile Ala His Leu Gly Gly His Ala Ile Val Val Asp Ser Gly Ser
65                  70                  75                  80

Ser Gln Met Gly Lys Gly Glu Ser Leu Gln Asp Thr Ala Ala Val Leu
                85                  90                  95

Ser Arg Tyr Val Glu Ala Ile Val Trp Arg Thr Tyr Ala His Ser Asn
            100                 105                 110

Phe His Ala Met Ala Glu Thr Ser Thr Val Pro Leu Val Asn Ser Leu
        115                 120                 125

Ser Asp Asp Leu His Pro Cys Gln Ile Leu Ala Asp Leu Gln Thr Ile
    130                 135                 140

Val Glu Asn Leu Ser Pro Glu Glu Gly Pro Ala Gly Leu Lys Gly Lys
145                 150                 155                 160

Lys Ala Val Tyr Leu Gly Asp Gly Asp Asn Asn Met Ala Asn Ser Tyr
                165                 170                 175

Met Ile Gly Phe Ala Thr Ala Gly Met Asp Ile Ser Ile Ile Ala Pro
            180                 185                 190
```

Glu Gly Phe Gln Pro Arg Ala Glu Phe Val Glu Arg Ala Glu Lys Arg
        195                 200                 205

Gly Gln Glu Thr Gly Ala Lys Val Val Val Thr Asp Ser Leu Asp Glu
        210                 215                 220

Val Ala Gly Ala Asp Val Val Ile Thr Asp Thr Trp Val Ser Met Gly
225                 230                 235                 240

Met Glu Asn Asp Gly Ile Asp Arg Thr Thr Pro Phe Val Pro Tyr Gln
                245                 250                 255

Val Asn Asp Glu Val Met Ala Lys Ala Asn Asp Gly Ala Ile Phe Leu
                260                 265                 270

His Cys Leu Pro Ala Tyr Arg Gly Lys Glu Val Ala Ala Ser Val Ile
                275                 280                 285

Asp Gly Pro Ala Ser Lys Val Phe Asp Glu Ala Glu Asn Arg Leu His
                290                 295                 300

Ala Gln Lys Ala Leu Leu Val Trp Leu Leu Ala Asn Gln Pro Arg
305                 310                 315

<210> SEQ ID NO 37
<211> LENGTH: 533
<212> TYPE: PRT
<213> ORGANISM: Unknown
<220> FEATURE:
<223> OTHER INFORMATION: Glutamate expoter (NCgl1221)
<220> FEATURE:
<221> NAME/KEY: MISC_FEATURE
<223> OTHER INFORMATION: Glutamate expoter (NCgl1221)

<400> SEQUENCE: 37

Met Ile Leu Gly Val Pro Ile Gln Tyr Leu Leu Tyr Ser Leu Trp Asn
1               5                   10                  15

Trp Ile Val Asp Thr Gly Phe Asp Val Ala Ile Ile Leu Val Leu Ala
                20                  25                  30

Phe Leu Ile Pro Arg Ile Gly Arg Leu Ala Met Arg Ile Ile Lys Arg
            35                  40                  45

Arg Val Glu Ser Ala Ala Asp Ala Asp Thr Thr Lys Asn Gln Leu Ala
        50                  55                  60

Phe Ala Gly Val Gly Val Tyr Ile Ala Gln Ile Val Ala Phe Phe Met
65                  70                  75                  80

Leu Ala Val Ser Ala Met Gln Ala Phe Gly Phe Ser Leu Ala Gly Ala
                85                  90                  95

Ala Ile Pro Ala Thr Ile Ala Ser Ala Ala Ile Gly Leu Gly Ala Gln
            100                 105                 110

Ser Ile Val Ala Asp Phe Leu Ala Gly Phe Phe Ile Leu Thr Glu Lys
        115                 120                 125

Gln Phe Gly Val Gly Asp Trp Val Arg Phe Glu Gly Asn Gly Ile Val
    130                 135                 140

Val Glu Gly Thr Val Ile Glu Ile Thr Met Arg Ala Thr Lys Ile Arg
145                 150                 155                 160

Thr Ile Ala Gln Glu Thr Val Ile Ile Pro Asn Ser Thr Ala Lys Val
                165                 170                 175

Cys Ile Asn Asn Ser Asn Asn Trp Ser Arg Ala Val Val Val Ile Pro
            180                 185                 190

Ile Pro Met Leu Gly Ser Glu Asn Ile Thr Asp Val Ile Ala Arg Ser
        195                 200                 205

Glu Ala Ala Thr Arg Arg Ala Leu Gly Gln Glu Lys Ile Ala Pro Glu
    210                 215                 220

Ile Leu Gly Glu Leu Asp Val His Pro Ala Thr Glu Val Thr Pro Pro
225                 230                 235                 240

Thr Val Val Gly Met Pro Trp Met Val Thr Met Arg Phe Leu Val Gln
            245                 250                 255

Val Thr Ala Gly Asn Gln Trp Leu Val Glu Arg Ala Ile Arg Thr Glu
            260                 265                 270

Ile Ile Ser Glu Phe Trp Glu Tyr Gly Ser Ala Thr Thr Thr Ser
            275                 280                 285

Gly Thr Leu Ile Asp Ser Leu His Val Glu His Glu Pro Lys Thr
            290                 295                 300

Ser Leu Ile Asp Ala Ser Pro Gln Ala Leu Lys Glu Pro Lys Pro Glu
305                 310                 315                 320

Ala Ala Ala Thr Val Ala Ser Leu Ala Ala Ser Ser Asn Asp Ala
            325                 330                 335

Asp Asn Ala Asp Ala Ser Val Ile Asn Ala Gly Asn Pro Glu Lys Glu
            340                 345                 350

Leu Asp Ser Asp Val Leu Glu Gln Glu Leu Ser Ser Glu Glu Pro Glu
            355                 360                 365

Glu Thr Ala Lys Pro Asp His Ser Leu Arg Gly Phe Phe Arg Thr Asp
            370                 375                 380

Tyr Tyr Pro Asn Arg Trp Gln Lys Ile Leu Ser Phe Gly Gly Arg Val
385                 390                 395                 400

Arg Met Ser Thr Ser Leu Leu Leu Gly Ala Leu Leu Leu Leu Ser Leu
            405                 410                 415

Phe Lys Val Met Thr Val Glu Pro Glu Asn Trp Gln Asn Ser Ser
            420                 425                 430

Gly Trp Leu Ser Pro Ser Thr Ala Thr Ser Thr Ala Val Thr Thr Ser
            435                 440                 445

Glu Thr Ser Ala Pro Val Ser Thr Pro Ser Met Thr Val Pro Thr Thr
450                 455                 460

Val Glu Glu Thr Pro Thr Met Glu Ser Asn Val Glu Thr Gln Gln Glu
465                 470                 475                 480

Thr Ser Thr Pro Ala Thr Ala Thr Pro Gln Arg Ala Asp Thr Ile Glu
            485                 490                 495

Pro Thr Glu Glu Ala Thr Ser Gln Glu Glu Thr Thr Ala Ser Gln Thr
            500                 505                 510

Gln Ser Pro Ala Val Glu Ala Pro Thr Ala Val Gln Glu Thr Val Ala
            515                 520                 525

Pro Thr Ser Thr Pro
    530

<210> SEQ ID NO 38
<211> LENGTH: 711
<212> TYPE: PRT
<213> ORGANISM: Unknown
<220> FEATURE:
<223> OTHER INFORMATION: Ornithine decarboxylase (ODC)
<220> FEATURE:
<221> NAME/KEY: MISC_FEATURE
<223> OTHER INFORMATION: Ornithine decarboxylase (ODC)
<220> FEATURE:
<221> NAME/KEY: MISC_FEATURE
<223> OTHER INFORMATION: lysCP1 promoter

<400> SEQUENCE: 38

Met Lys Ser Met Asn Ile Ala Ala Ser Ser Glu Leu Val Ser Arg Leu
1               5                   10                  15

```
Ser Ser His Arg Arg Val Val Ala Leu Gly Asp Thr Asp Phe Thr Asp
         20                  25                  30
Val Ala Ala Val Val Ile Thr Ala Ala Asp Ser Arg Ser Gly Ile Leu
     35                  40                  45
Ala Leu Leu Lys Arg Thr Gly Phe His Leu Pro Val Phe Leu Tyr Ser
 50                  55                  60
Glu His Ala Val Glu Leu Pro Ala Gly Val Thr Ala Val Ile Asn Gly
65                  70                  75                  80
Asn Glu Gln Gln Trp Leu Glu Leu Glu Ser Ala Ala Cys Gln Tyr Glu
                 85                  90                  95
Glu Asn Leu Leu Pro Pro Phe Tyr Asp Thr Leu Thr Gln Tyr Val Glu
            100                 105                 110
Met Gly Asn Ser Thr Phe Ala Cys Pro Gly His Gln His Gly Ala Phe
        115                 120                 125
Phe Lys Lys His Pro Ala Gly Arg His Phe Tyr Asp Phe Phe Gly Glu
130                 135                 140
Asn Val Phe Arg Ala Asp Met Cys Asn Ala Asp Val Lys Leu Gly Asp
145                 150                 155                 160
Leu Leu Ile His Glu Gly Ser Ala Lys Asp Ala Gln Lys Phe Ala Ala
                165                 170                 175
Lys Val Phe His Ala Asp Lys Thr Tyr Phe Val Leu Asn Gly Thr Ser
            180                 185                 190
Ala Ala Asn Lys Val Val Thr Asn Ala Leu Leu Thr Arg Gly Asp Leu
        195                 200                 205
Val Leu Phe Asp Arg Asn Asn His Lys Ser Asn His His Gly Ala Leu
    210                 215                 220
Ile Gln Ala Gly Ala Thr Pro Val Tyr Leu Glu Ala Ser Arg Asn Pro
225                 230                 235                 240
Phe Gly Phe Ile Gly Gly Ile Asp Ala His Cys Phe Asn Glu Glu Tyr
                245                 250                 255
Leu Arg Gln Gln Ile Arg Asp Val Ala Pro Glu Lys Ala Asp Leu Pro
            260                 265                 270
Arg Pro Tyr Arg Leu Ala Ile Ile Gln Leu Gly Thr Tyr Asp Gly Thr
        275                 280                 285
Val Tyr Asn Ala Arg Gln Val Ile Asp Thr Val Gly His Leu Cys Asp
    290                 295                 300
Tyr Ile Leu Phe Asp Ser Ala Trp Val Gly Tyr Glu Gln Phe Ile Pro
305                 310                 315                 320
Met Met Ala Asp Ser Ser Pro Leu Leu Leu Glu Leu Asn Glu Asn Asp
                325                 330                 335
Pro Gly Ile Phe Val Thr Gln Ser Val His Lys Gln Gln Ala Gly Phe
            340                 345                 350
Ser Gln Thr Ser Gln Ile His Lys Lys Asp Asn His Ile Arg Gly Gln
        355                 360                 365
Ala Arg Phe Cys Pro His Lys Arg Leu Asn Asn Ala Phe Met Leu His
    370                 375                 380
Ala Ser Thr Ser Pro Phe Tyr Pro Leu Phe Ala Ala Leu Asp Val Asn
385                 390                 395                 400
Ala Lys Ile His Glu Gly Glu Ser Gly Arg Arg Leu Trp Ala Glu Cys
                405                 410                 415
Val Glu Ile Gly Ile Glu Ala Arg Lys Ala Ile Leu Ala Arg Cys Lys
            420                 425                 430
```

```
Leu Phe Arg Pro Phe Ile Pro Pro Val Val Asp Gly Lys Leu Trp Gln
            435                 440                 445

Asp Tyr Pro Thr Ser Val Leu Ala Ser Asp Arg Arg Phe Phe Ser Phe
450                 455                 460

Glu Pro Gly Ala Lys Trp His Gly Phe Glu Gly Tyr Ala Ala Asp Gln
465                 470                 475                 480

Tyr Phe Val Asp Pro Cys Lys Leu Leu Leu Thr Thr Pro Gly Ile Asp
                485                 490                 495

Ala Glu Thr Gly Glu Tyr Ser Asp Phe Gly Val Pro Ala Thr Ile Leu
            500                 505                 510

Ala His Tyr Leu Arg Glu Asn Gly Ile Val Pro Glu Lys Cys Asp Leu
        515                 520                 525

Asn Ser Ile Leu Phe Leu Leu Thr Pro Ala Glu Ser His Glu Lys Leu
530                 535                 540

Ala Gln Leu Val Ala Met Leu Ala Gln Phe Glu Gln His Ile Glu Asp
545                 550                 555                 560

Asp Ser Pro Leu Val Glu Val Leu Pro Ser Val Tyr Asn Lys Tyr Pro
                565                 570                 575

Val Arg Tyr Arg Asp Tyr Thr Leu Arg Gln Leu Cys Gln Glu Met His
            580                 585                 590

Asp Leu Tyr Val Ser Phe Asp Val Lys Asp Leu Gln Lys Ala Met Phe
        595                 600                 605

Arg Gln Gln Ser Phe Pro Ser Val Val Met Asn Pro Gln Asp Ala His
610                 615                 620

Ser Ala Tyr Ile Arg Gly Asp Val Glu Leu Val Arg Ile Arg Asp Ala
625                 630                 635                 640

Glu Gly Arg Ile Ala Ala Glu Gly Ala Leu Pro Tyr Pro Pro Gly Val
                645                 650                 655

Leu Cys Val Val Pro Gly Glu Val Trp Gly Gly Ala Val Gln Arg Tyr
            660                 665                 670

Phe Leu Ala Leu Glu Glu Gly Val Asn Leu Leu Pro Gly Phe Ser Pro
        675                 680                 685

Glu Leu Gln Gly Val Tyr Ser Glu Thr Asp Ala Asp Gly Val Lys Arg
690                 695                 700

Leu Tyr Gly Tyr Val Leu Lys
705                 710

<210> SEQ ID NO 39
<211> LENGTH: 289
<212> TYPE: DNA
<213> ORGANISM: Artificial Sequence
<220> FEATURE:
<223> OTHER INFORMATION: lysCP1 promoter

<400> SEQUENCE: 39
ccgatgctag ggcgaaaagc acggcgagca gattgctttg cacttgattc agggtagttg      60
actaaagagt tgctcgcgaa gtagcacctg tcacttttgt ctcaaatatt aaatcgaata     120
tcaatatatg gtctgtttat tggaacgcgt cccagtggct gagacgcatc cgctaaagcc     180
ccaggaaccc tgtgcagaaa gaaaacactc ctctggctag gtagacacag tttattgtgg     240
tagagttgag cgggtaactg tcagcacgta gatcgaaagg tgcacaaag                 289
```

MICROORGANISMS FOR PRODUCING PUTRESCINE OR ORNITHINE AND PROCESS FOR PRODUCING PUTRESCINE OR ORNITHINE USING THEM

CROSS REFERENCE TO RELATED APPLICATIONS

This application is a continuation of U.S. patent application Ser. No. 15/746,300, filed on Jan. 19, 2018, which is a National Stage application under 35 U.S.C. § 371 of International Application No. PCT/KR2016/007841, filed Jul. 19, 2016, which claims the benefit under 35 U.S.C. § 119(a) of Korean Patent Application No. 10-2015-0102624, filed Jul. 20, 2015, the contents of all of which are incorporated herein in their entireties by reference thereto.

SEQUENCE LISTING

This application contains a Sequence Listing which has been submitted in ASCII format via EFS and is hereby incorporated by reference. The ASCII copy was originally created in parent application U.S. Ser. No. 15/746,300 on Jan. 16, 2018 and amended therein on Apr. 16, 2018. In the instant application herein, the first sequence listing was filed Feb. 28, 2020 and subsequently amended on Sep. 15, 2020 and Jun. 4, 2020. The amended sequence listing filed Jun. 4, 2020, via EFS-Web, is named OPA16079_Seq_List.txt with a file size of 89,068 bytes.

TECHNICAL FIELD

The present disclosure relates to a recombinant microorganism producing putrescine or ornithine, and a method for producing putrescine or ornithine using the same.

BACKGROUND ART

Biogenic amines (BAs) are nitrogen compounds that are mainly produced by decarboxylation of amino acids or amination and transamination of aldehydes and ketones. These biogenic amines have low molecular weight and are synthesized during the metabolic processes in microorganisms, plants, and animals thus being known as constituting elements which are frequently discovered in their cells.

Among them, putrescine is discovered in gram negative bacteria or fungi and is present in high concentration in various species, and thus putrescine is expected to play an important role in the metabolism of microorganisms. In general, putrescine is an important raw material for the synthesis of polyamine nylon-4,6 and is produced mainly by chemical synthesis. The chemical synthesis is a 3-step process including a catalytic oxidation reaction, a reaction using a cyanide compound, and a hydrogenation reaction using high-pressure hydrogen. Accordingly, there is a demand for the development of a more environment-friendly and energy-effective method involving biomass utilization.

Under these circumstances, various methods for producing putrescine at high concentration by transforming *E. coli* and a microorganism of the genus *Corynebacterium* were disclosed (International Patent Publication No. WO 06/005603; International Patent Publication No. WO 09/125924; Qian Z D et al., *Biotechnol. Bioeng.* 104 (4): 651-662, 2009; Schneider et al., *Appl. Microbiol. Biotechnol.* 88 (4): 859-868, 2010; Schneider et al., *Appl. Microbiol. Biotechnol.* 95: 169-178, 2012).

On the other hand, ornithine is a material widely discovered in plants, animals, and microorganisms, and serves as a precursor for biosynthesis of arginine, proline, and polyamine. Additionally, ornithine plays an important role in the pathway of producing urea from amino acids or ammonia and disposing through the ornithine cycle during the in-vivo metabolism of higher organisms. Ornithine is effective in muscle production and reduction of body fat, and thus it has been used as a nutrient supplement and also as a pharmaceutical drug for improving liver cirrhosis and hepatic dysfunction. Methods of producing ornithine include a method of using milk casein as a digestive enzyme and a method of using *E. coli* or a microorganism of the genus *Corynebacterium* (Korean Patent No. 10-1372635; T. Gotoh et al., *Bioprocess Biosyst. Eng.*, 33: 773-777, 2010).

*E. coli* and a microorganism of the genus *Corynebacterium* are similar in the biosynthetic pathways for producing putrescine or ornithine, but they also exhibit differences as follows. First, the microorganism of the genus *Corynebacterium* has a "cyclic pathway", in which glutamic acid is converted into N-acetyl-L-glutamic acid and N-acetyl-L-ornithine is converted into L-ornithine by argJ (bifunctional ornithine acetyltransferase/N-acetylglutamate synthase, EC 2.3.1.35). In contrast, *E. coli* is involved in the biosynthesis of putrescine or ornithine by a "linear pathway", in which argA (N-acetylglutamate synthase, EC 2.3.1.1) and argE (Acetylornithine deacetylase, EC 3.5.1.16) replace the role of the argJ in the microorganism of the genus *Corynebacterium*.

In the microorganism of the genus *Corynebacterium*, it is known that an acetyl group recycles between ornithine and glutamic acid in ArgJ. However, in *E. coli*, ArgA attaches the acetyl group of acetyl-CoA to glutamate in order to produce N-acetylglutamate, and ArgE N-acetyl-ornithine decomposes N-acetyl-ornithine to produce ornithine and acetate (Schneider et al., *Appl. Microbiol. Biotechnol.* 91, 17-30, 2011).

In particular, pta-ackA (pta, phosphotransacetylase; ackA, acetate kinase) operon and acetyl-coenzyme A synthetase (acs) are known as genes to synthesize acetyl-CoA using acetate.

DISCLOSURE

Technical Problem

The present inventors have made many efforts to improve the ability of a microorganism of the genus *Corynebacterium* to produce ornithine and putrescine, and as a result they have discovered that the introduction of *E. coli*-derived argA and argE into a microorganism of the genus *Corynebacterium* can improve its ability to produce ornithine and putrescine, thereby completing the present invention.

Technical Solution

An object of the present disclosure provides a recombinant microorganism producing putrescine or ornithine in high yield.

Another object of the present disclosure provides a method for producing putrescine or ornithine using the microorganism above.

Advantageous Effects of the Invention

It was confirmed that the microorganism of the genus *Corynebacterium* of the present disclosure producing putrescine or ornithine can improve the amount of putrescine- or ornithine production when the microorganism is introduced with *E. coli*-derived argA and *E. coli*-derived argE, and also when the acetate utilization pathway is reinforced. Accordingly, the microorganism of the present disclosure can be widely used for the production of putrescine or ornithine, and also, can be widely used as an effective and desirable means to supply raw materials for the production of various polymer products, in which the putrescine or ornithine is used as a raw material, from the economic and environmental aspects.

BEST MODE

Figure 1:
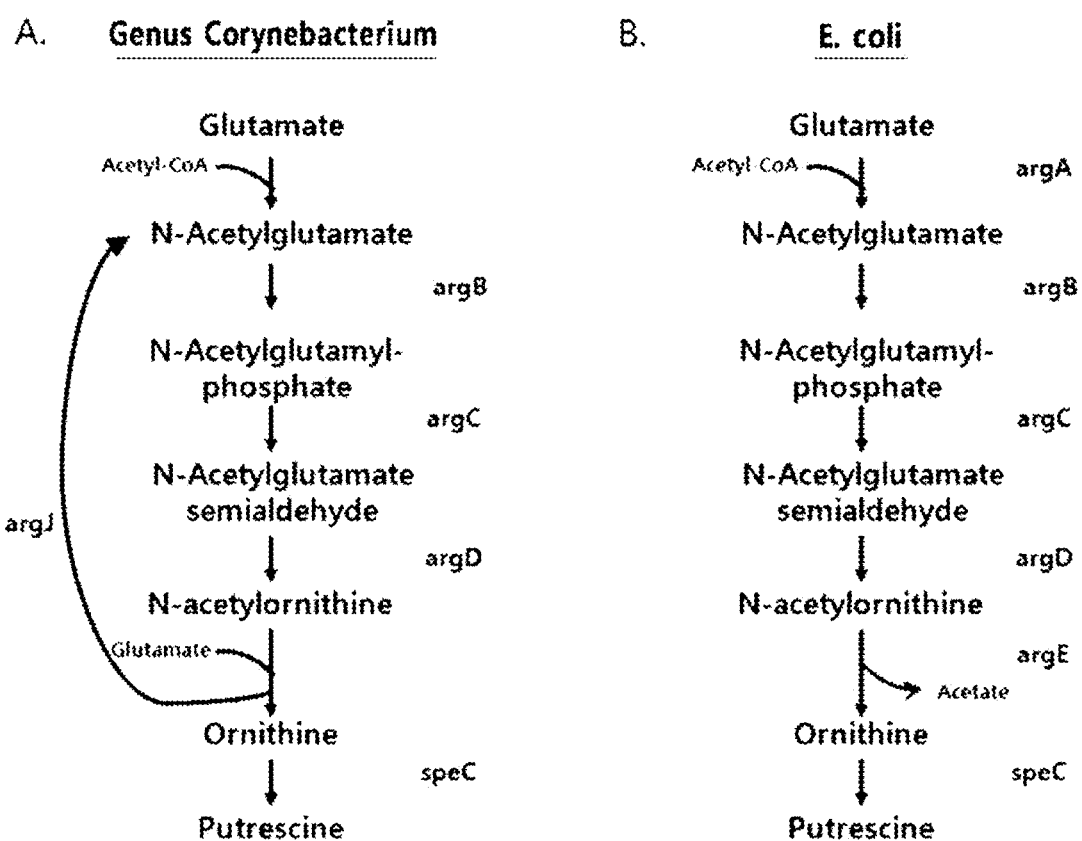
FIG. 1 is a schematic diagram illustrating a biosynthetic pathway (a cyclic pathway) for producing putrescine and ornithine in a microorganism of the genus *Corynebacterium* (A) and a biosynthetic pathway (a linear pathway) for producing putrescine and ornithine in *E. coli* (B).
Figure 2:
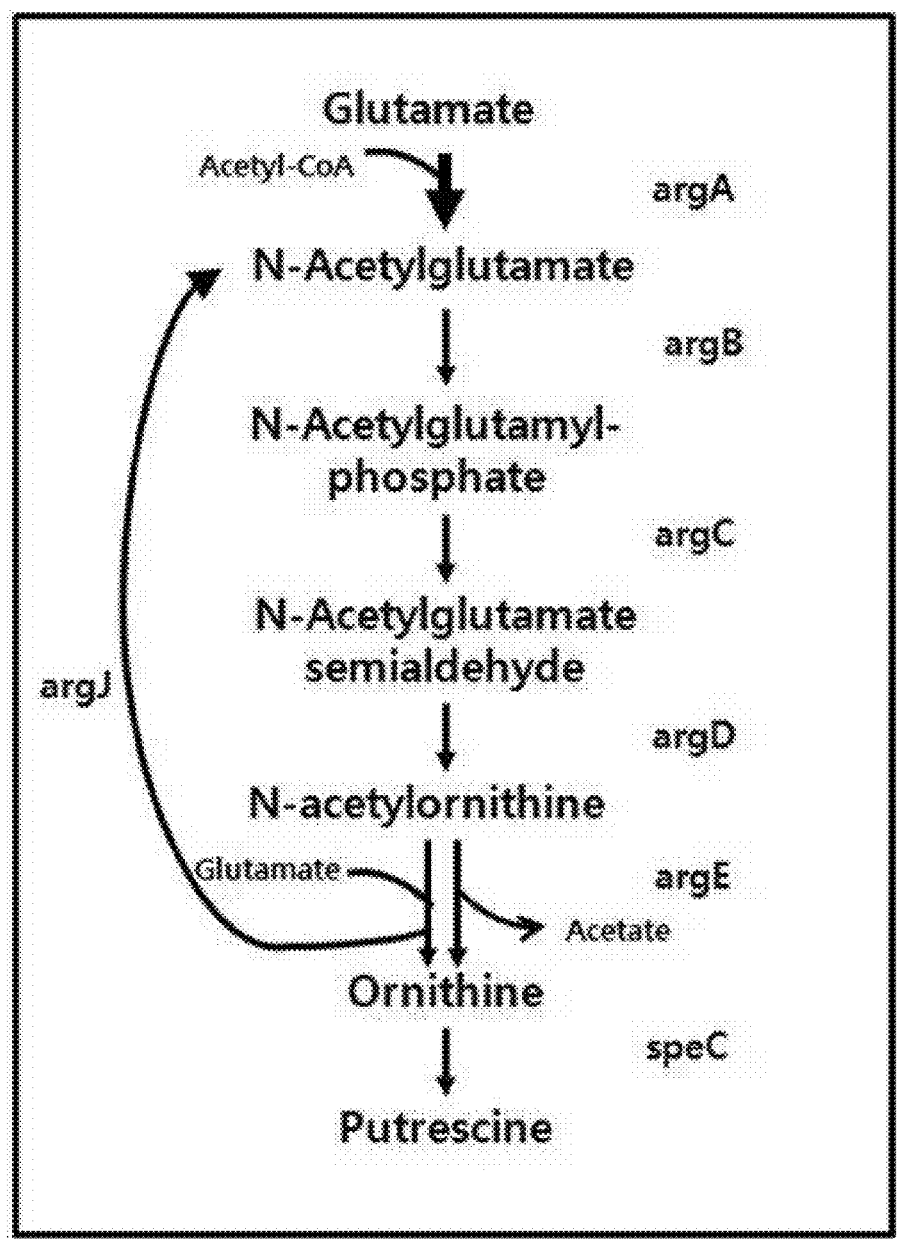
FIG. 2 is a schematic diagram illustrating the biosynthetic pathway which has improved the ability to produce putrescine and ornithine by introducing *E. coli*-derived argA and *E. coli*-derived argE into a microorganism of the genus *Corynebacterium*, which is in a state expressing argJ.

An aspect of the present disclosure provides a modified microorganism of the genus *Corynebacterium* producing putrescine or ornithine, in which activities of N-acetylglutamate synthase from *E. coli* and acetylornithine deacetylase from *E. coli* are introduced.

An exemplary embodiment of the present disclosure provides a modified microorganism of the genus *Corynebacterium* producing putrescine or ornithine, in which the *E. coli*-derived N-acetylglutamate synthase consists of an amino acid sequence of SEQ ID NO: 1.

Another exemplary embodiment of the present disclosure provides a modified microorganism of the genus *Corynebacterium* producing putrescine or ornithine, in which the *E. coli*-derived acetylornithine deacetylase consists of an amino acid sequence of SEQ ID NO: 3.

Still another exemplary embodiment of the present disclosure provides a modified microorganism of the genus *Corynebacterium* producing putrescine or ornithine, in which the microorganism of the genus *Corynebacterium* is selected from the group consisting of *Corynebacterium glutamicum*, *Corynebacterium ammoniagenes*, *Corynebacterium thermoaminogenes*, *Brevibacterium flavum*, and *Brevibacterium lactofermentum*.

Still another exemplary embodiment of the present disclosure provides a modified microorganism of the genus *Corynebacterium* producing putrescine or ornithine, in which an activity of phosphotransacetylase and acetate kinase operon (pta-ackA operon) is further enhanced compared to its endogenous activity.

Still another exemplary embodiment of the present disclosure provides a modified microorganism of the genus *Corynebacterium* producing putrescine or ornithine, in which the phosphotransacetylase and acetate kinase operon consists of an amino acid sequence of SEQ ID NO: 5 or 7.

Still another exemplary embodiment of the present disclosure provides a modified microorganism of the genus *Corynebacterium* producing putrescine or ornithine, in which an activity of *E. coli*-derived acetyl-CoA synthetase (acs) is further introduced.

Still another exemplary embodiment of the present disclosure provides a modified microorganism of the genus *Corynebacterium* producing putrescine or ornithine, in which the *E. coli*-derived acetyl-CoA synthetase (acs) consists of an amino acid sequence of SEQ ID NO: 9.

Still another exemplary embodiment of the present disclosure provides a modified microorganism of the genus *Corynebacterium* producing putrescine or ornithine, in which an activity of ornithine decarboxylase (ODC) is further introduced.

Still another exemplary embodiment of the present disclosure provides a modified microorganism of the genus *Corynebacterium* producing putrescine or ornithine, in which an activity of i) ornithine carbamoyltransferase (ArgF), ii) glutamate exporter, or iii) ornithine carbamoyltransferase and glutamate exporter is further weakened, compared to its endogenous activity.

Still another exemplary embodiment of the present disclosure provides a modified microorganism of the genus *Corynebacterium* producing putrescine or ornithine, in which an activity of at least one selected from the group consisting of acetyl gamma glutamyl phosphate reductase (ArgC), acetylglutamate synthase or ornithine acetyltransferase (ArgJ), acetylglutamate kinase (ArgB), and acetyl ornithine aminotransferase (ArgD), is further enhanced compared to its endogenous activity.

Still another exemplary embodiment of the present disclosure provides a modified microorganism of the genus *Corynebacterium* producing putrescine or ornithine, in which an activity of acetyltransferase is further weakened compared to its endogenous activity.

Still another exemplary embodiment of the present disclosure provides a modified microorganism of the genus *Corynebacterium* producing putrescine or ornithine, in which the acetyltransferase consists of the amino acid sequence of SEQ ID NO: 30 or 31.

Still another exemplary embodiment of the present disclosure provides a modified microorganism of the genus *Corynebacterium* producing putrescine or ornithine, in which an activity of the putrescine exporter is further enhanced compared to its endogenous activity.

Still another exemplary embodiment of the present disclosure provides a modified microorganism of the genus *Corynebacterium* producing putrescine or ornithine, in which the putrescine exporter consists of the amino acid sequence of SEQ ID NO: 26 or 28.

Another aspect of the present disclosure provides a method for producing putrescine or ornithine, including:

(i) culturing the modified microorganism of the genus *Corynebacterium* producing putrescine or ornithine in a medium; and (ii) recovering putrescine or ornithine from the cultured microorganism or the medium.

In an exemplary embodiment of the present disclosure, the modified microorganism of the genus *Corynebacterium* is *Corynebacterium glutamicum*.

Hereinafter, the present disclosure will be described in detail.

An embodiment of the present disclosure provides a modified microorganism of the genus *Corynebacterium* producing putrescine or ornithine, in which activities of *E. coli*-derived N-acetylglutamate synthase and *E. coli*-derived acetylornithine deacetylase are introduced.

As used herein, the term "N-acetylglutamate synthase" refers to an enzyme which mediates the reaction producing N-acetylglutamate from glutamate and acetyl-CoA, and the N-acetylglutamate produced thereof may be used as a precursor of ornithine and arginine.

In the present disclosure, N-acetylglutamate synthase may include, for example, the protein having an amino acid sequence of SEQ ID NO: 1, and any protein, which has a homology of 70% or higher, specifically 80% or higher, more specifically 90% or higher, even more specifically 95% or higher, yet even more specifically 98% or higher, and most specifically 99% or higher, to the amino acid sequence above, as long as the protein has the substantial activity of N-acetylglutamate synthase, without limitation.

Additionally, the proteins exhibiting the activity above may show differences in amino acid sequences, according to the species and strains of the microorganism. Accordingly, the N-acetylglutamate synthase of the present disclosure may be, for example, one from *E. coli*, although it is not limited thereto.

As a sequence having a homology to the sequence above, if the amino acid sequence is one which has substantially the same or corresponding to biological activity of a protein of SEQ ID NO: 1, it is obvious in that amino acid sequences with a deletion, a modification, a substitution, or an addition in part of the sequences should also be included in the scope of the present disclosure.

The polynucleotide encoding the N-acetylglutamate synthase of the present disclosure may include, without limitation, a polynucleotide encoding the protein having an amino acid sequence of SEQ ID NO: 1, and any protein, which has a homology of 70% or higher, specifically 80% or higher, more specifically 90% or higher, even more specifically 95% or higher, yet even more specifically 98% or higher, and most specifically 99% or higher, to the above amino acid sequence, as long as the polynucleotide has an activity similar to that of N-acetylglutamate synthase, and for example, a polynucleotide sequence of SEQ ID NO: 2 may be included.

As used herein, the term "acetylornithine deacetylase" refers to an enzyme which mediates the reaction involved in the production of acetic acid and ornithine by mediating the hydrolysis of acetylornithine.

In the present disclosure, acetylornithine deacetylase may include, without limitation, the protein having an amino acid sequence of SEQ ID NO: 3, and any protein, which has a homology of 70% or higher, specifically 80% or higher, more specifically 90% or higher, even more specifically 95% or higher, yet even more specifically 98% or higher, and most specifically 99% or higher, to the above amino acid sequence, as long as the protein has the substantial activity of separating acetyl group and ornithine from acetylornithine.

Additionally, the proteins exhibiting the activity above may show a difference in amino acid sequences, according to the species and strains of the microorganism. Accordingly, the acetylornithine deacetylase of the present disclosure may be one from *E. coli*, although it is not limited thereto. As a sequence having a homology, if the amino acid sequence is one which has substantially the same or corresponding to biological activity of a protein of SEQ ID NO: 3, it is obvious in that amino acid sequences with a deletion, a modification, a substitution, or an addition in part of the sequences should also be included in the scope of the present disclosure.

The polynucleotide encoding acetylornithine deacetylase of the present disclosure may include, as long as the polynucleotide has an activity similar to that of the acetylornithine deacetylase protein, the protein having an amino acid sequence of SEQ ID NO: 3, or a polynucleotide encoding a protein, which has a homology of 70% or higher, specifically 80% or higher, more specifically 90% or higher, even more specifically 95% or higher, yet even more specifically 98% or higher, and most specifically 99% or higher, to the amino acid sequence above, for example, a polynucleotide sequence of SEQ ID NO: 4.

Additionally, the polynucleotide encoding N-acetylglutamate synthase or acetylornithine deacetylase of the present disclosure may be hybridized with the polynucleotide sequence of SEQ ID NO: 2 or SEQ ID NO: 4 or a probe derived from the polynucleotide sequence under stringent conditions, and it may be a modified type of N-acetylglutamate synthase or acetylornithine deacetylase that functions normally. In the above, the term "stringent conditions" refers to a condition that enables a specific hybridization between polynucleotides. For example, the stringent conditions are specifically described in references (e.g., J. Sambrook et al., supra).

In the above, the term "homology" refers to the degree of identity with the given amino acid sequence or a polynucleotide sequence, and may be indicated in percentage. As used herein, the homologous sequence having the same or similar activity with the given polypeptide sequence or polynucleotide sequence may be indicated in terms of "% homology". For example, the % homology may be confirmed using standard software, i.e., BLAST 2.0, for calculating parameters such as score, identity, and similarity, or by comparing sequences via southern hybridization experiments, and the appropriate hybridization condition to be defined may be determined by a method known to a skilled person in the art (e.g., J. Sambrook et al., Molecular Cloning, A Laboratory Manual, 2nd Edition, Cold Spring Harbor Laboratory press, Cold Spring Harbor, N.Y., 1989; F. M. Ausubel et al., Current Protocols in Molecular Biology, John Wiley & Sons, Inc., New York).

On the other hand, the microorganism of the present disclosure may include both a natural type and a modified type, e.g., microorganisms that belong to the genus *Escherichia*, the genus *Shigella*, the genus *Citrobacter*, the genus *Salmonella*, the genus *Enterobacter*, the genus *Yersinia*, the genus *Klebsiella*, the genus *Erwinia*, the genus *Corynebacterium*, the genus *Brevibacterium*, the genus *Lactobacillus*, the genus *Selenomanas*, the genus *Vibrio*, the genus *Pseudomonas*, the genus *Streptomyces*, the genus *Arcanobacterium*, the genus *Alcaligenes*, etc. Specifically, the microorganism of the present disclosure may be a microorganism belonging to the genus *Corynebacterium*, more specifically, a microorganism selected from the group consisting of *Corynebacterium glutamicum*, *Corynebacterium ammoniagenes*, *Corynebacterium thermoaminogenes*, *Brevibacterium flavum*, and *Brevibacterium lactofermentum*, and more specifically, *Corynebacterium glutamicum*, but it is not limited thereto.

Specifically, as used herein, the term "a microorganism of the genus *Corynebacterium* producing putrescine or ornithine" refers to a microorganism of the genus *Corynebacterium* producing putrescine or ornithine in a natural state; or a microorganism of the genus *Corynebacterium* producing putrescine or ornithine prepared by providing the ability to produce putrescine or ornithine into its parent strain, which cannot produce putrescine or ornithine.

The microorganism, which is provided with the ability to produce putrescine or ornithine or can produce putrescine or ornithine, may have an improved ability to produce ornithine, which is used as a raw material for biosynthesis of putrescine, by modifying the activities of acetylglutamate synthase (which converts glutamate into N-acetylglutamate), ornithine acetyltransferase (ArgJ, which converts acetylornithine into ornithine), acetylglutamate kinase (ArgB, which converts acetylglutamate into N-acetylglutamyl phosphate), gamma glutamyl phosphate reductase (ArgC, which converts N-acetylglutamyl phosphate into N-acetylglutamate semialdehyde), and acetyl ornithine aminotransferase (ArgD, which converts acetylglutamate semialdehyde into N-acetylornithine) to be increased, compared to their endogenous activities, in order to increase the biosynthetic pathway from glutamate to ornithine, although not particularly limited thereto.

Additionally, the microorganism may be modified to weaken the activities of ornithine carbamoyltransferase (ArgF, which is involved in the synthesis arginine from ornithine), a protein(s) involved in the export of glutamate, and/or a protein(s) that acetylates putrescine, compared to their endogenous activities; and/or to introduce the activity of ornithine decarboxylase (ODC).

As used herein, the term "introduction of activity" may refer to an activity of a protein, which is not present or weak in a microorganism, is newly introduced or enhanced in the corresponding microorganism. Specifically, it may include inserting or derlivering a gene encoding a protein, which is not present in the microorganism, into the microorganism to be expressed therein, or inducing a modification of the protein for enhancing the expression of the protein, which is not expressed or almost not expressed in the microorganism, but is not limited thereto.

On the other hand, in the present disclosure, modifications such as introduction of activity, enhancement of activity, weakening of activity, etc., may occur through a process called transformation. As used herein, the term "transformation" refers to a process of introducing a vector, which includes a polynucleotide encoding a particular protein or a promoter sequence with strong or weak activity, etc., into the host cell thereby enabling the expression of the protein encoded by the polynucleotide or inducing a modification of the chromosome in the host cell. Additionally, the polynucleotide includes DNA and RNA which encode the target protein. The polynucleotide may be inserted in any form insofar as it can be introduced into a host cell and expressed or induce a modification therein. For example, the polynucleotide may be introduced into a host cell in the form of an expression cassette, which is a gene construct including all essential elements required for self-expression. The expression cassette may conventionally include a promoter operably connected to the polynucleotide, a transcription termination signal, a ribosome-binding domain, and a translation termination signal, and may be in the form of an expression vector capable of self-replication. Additionally, the polynucleotide may be introduced into a host cell as it is, and operably connected to a sequence essential for its expression in the host cell, but is not limited thereto.

Additionally, as used herein, the term "operably connected" refers to a functional connection between a promoter sequence, which initiates and mediates the transcription of the polynucleotide encoding the particular protein of the present disclosure, and the gene sequence.

As used herein, the term "vector" refers to a DNA construct including the nucleotide sequence of the polynucleotide encoding a protein of interest, in which the protein of interest is operably linked to a suitable regulatory sequence so that the protein of interest can be expressed in an appropriate host. The regulatory sequence includes a promoter capable of initiating transcription, any operator sequence for regulation of the transcription, a sequence encoding a suitable mRNA ribosome-binding domain, and a sequence for regulating transcription and translation. The vector, after being transformed into a suitable host cell, may be replicated or function irrespective of the host genome, or may be integrated into the host genome itself.

The vector used in the present disclosure may not be particularly limited as long as the vector is replicable in a host cell, and any vector known in the art may be used. Examples of the vector may include natural or recombinant plasmids, cosmids, viruses, and bacteriophages. For example, as a phage vector or cosmid vector, pWE15, M13, MBL3, MBL4, IXII, ASHII, APII, t10, t11, Charon4A, Charon21A, etc., may be used; and as a plasmid vector, those based on pBR, pUC, pBluescriptII, pGEM, pTZ, pCL, pET, etc., may be used. The vector to be used in the present disclosure may not be particularly limited and any vector known in the art may be used. Specifically, pDZTn, pACYC177, pACYC184, pCL, pECCG117, pUC19, pBR322, pMW 118, pCC1BAC vectors, etc., may be used.

As such, a polynucleotide encoding a target protein may be substituted with a modified polynucleotide using a vector for chromosomal insertion within bacteria. The insertion of the polynucleotide into the chromosome may be performed using a known method in the art, for example, by homologous recombination, but is not limited thereto. Since the vector of the present disclosure can be inserted into the chromosome via homologous recombination, a selection marker for confirming the insertion into the chromosome may be further included. The selection marker is used for selecting a transformed cell, i.e., in order to confirm whether the target polynucleotide has been inserted, and markers providing selectable phenotypes such as drug resistance, nutrient requirement, resistance to cytotoxic agents, and expression of surface proteins may be used. Under the circumstances where selective agents are treated, only the cells expressing the selection markers can survive or express other phenotypic traits, and thus the transformed cells can be easily selected.

The microorganism of the genus *Corynebacterium* of the present disclosure may be a modified microorganism of the genus *Corynebacterium* producing putrescine or ornithine, in which an activity of phosphotransacetylase and acetate kinase operon (pta-ackA operon) is further enhanced compared to its endogenous enzyme.

In the present disclosure, the phosphotransacetylase and acetate kinase operon (pta-ackA operon) are operons including genes that reversibly mediate the metabolic pathway, in which acetyl-CoA produced from glucose or pyruvate converts into acetic acid via acetyl phosphate, and the metabolic pathway in the opposite direction.

In the present disclosure, the phosphotransacetylase and acetate kinase operon may include, without limitation, the proteins including an amino acid sequence of SEQ ID NO: 5 or SEQ ID NO: 7, or any protein, which has a homology of 70% or higher, specifically 80% or higher, more specifically 90% or higher, specifically, even more specifically 95% or higher, yet even more specifically 98% or higher, or most specifically 99% or higher, to the above amino acid sequences, as long as the protein substantially mediates the reaction of producing acetyl-CoA from acetic acid.

Additionally, since the amino acid sequences of the proteins exhibiting the activities may vary according to the species or strains of a given microorganism, the phosphotransacetylase and acetate kinase operon in the present disclosure may not be limited to those origins from which they are derived. It is obvious in that any amino acid sequence, which has a homology to the sequences above and has a biological activity substantially the same as or corresponding to the protein of SEQ ID NO: 5 or SEQ ID NO: 7, can also belong to the scope of the present disclosure, although the amino acid sequence may have deletion, modification, substitution, or addition, in part of the sequence.

The polynucleotide encoding the phosphotransacetylase and acetate kinase operon of the present disclosure may include the polynucleotide which encodes the amino acid of SEQ ID NO: 5 or SEQ ID NO: 7, or the polynucleotide which encodes a protein having a homology of 70% or higher, specifically 80% or higher, more specifically 90% or higher, even more specifically 95% or higher, yet even more specifically 98% or higher, and most specifically 99% or higher to the above amino acid sequences, and most specifically may include the polynucleotide sequence of SEQ ID NO: 6 or SEQ ID NO: 8.

As used herein, the term "enhancement of activity" not only includes the drawing of a higher effect than the original function due to the new introduction of an activity or an increase in the activity of a protein itself, but also includes the increase in its activity by an increase in the activity of an endogenous gene, amplification of an endogenous gene from internal or external factor(s), deletion of regulatory factor(s) for inhibiting the gene expression, an increase in gene copy number, introduction of a gene from outside, modification of the expression regulatory sequence, and specifically, an increase in enzyme activity due to replacement or modification of a promoter and a mutation within the gene, etc.

Specifically, in the present disclosure, the increase in activity may be performed by:
1) increasing copy number of a polynucleotide encoding the enzyme,
2) modifying the expression regulatory sequence for increasing the expression of the polynucleotide,
3) modifying the polynucleotide sequence on the chromosome for enhancing the activity of the enzyme, or
4) modifying by a combination thereof,
but the method is not limited thereto.

The increase of copy number of a polynucleotide (method 1) may be performed in a form in which the polynucleotide is operably linked to a vector, or by inserting the polynucleotide into the chromosome of a host cell, although the method is not particularly limited thereto. Specifically, the copy number of a polynucleotide within the chromosome of the host cell may be increased by introducing a vector which can replicate and function regardless of a host cell and to which the polynucleotide encoding the protein of the present disclosure is operably linked; or may be increased by introducing a vector, which can insert the polynucleotide into the chromosome of a host cell and to which the polynucleotide is operably linked, into a host cell.

Then, the modification of the expression regulatory sequence for increasing the expression of a polynucleotide (method 2) may be performed by inducing a modification on the sequence through deletion, insertion, non-conservative or conservative substitution of the polynucleotide sequence, or a combination thereof to further enhance the activity of expression regulatory sequence, or by replacing the polynucleotide sequence with a polynucleotide sequence having a stronger activity, although the method is not particularly limited thereto. The expression regulatory sequence includes a promoter, an operator sequence, a sequence coding for ribosome-binding site, and a sequence regulating the termination of transcription and translation, although not particularly limited thereto.

A strong exogenous promoter, instead of the original promoter, may be connected to the upstream region of the expression unit of the polynucleotide. Examples of the strong promoter may be CJ7 promoter, lysCP1 promoter, EF-Tu promoter, groEL promoter, aceA or aceB promoter, etc., and more specifically, the expression rate may be improved by being operably connected to Corynebacterium-derived lysCP1 promoter (WO 2009/096689) or CJ7 promoter (Korean Patent No. 10-0620092 and WO 2006/065095), but the strong promoter is not limited thereto.

Furthermore, the modification of a polynucleotide sequence on the chromosome (method 3) may be performed by inducing a modification on the expression regulatory sequence through deletion, insertion, non-conservative or conservative substitution of the polynucleotide sequence, or a combination thereof to further enhance the activity of the polynucleotide sequence, or by replacing the polynucleotide sequence with an improved polynucleotide sequence having a stronger activity, although the method is not particularly limited thereto.

Specifically, in the present disclosure, the activity of the phosphotransacetylase and acetate kinase operon (pta-ackA operon) may be enhanced in comparison with its endogenous activity by any one method selected from the group consisting of a method of increasing the copy number of the operon in a cell, a method of introducing a modification on an expression regulatory sequence of the operon, a method of replacing an expression regulatory sequence of a gene on the operon with a sequence having a stronger activity, a method of replacing the genes encoding the enzymes with mutated genes on the chromosome for increasing the activities of the enzymes constituting the operon, and a method of introducing a modification on the gene on the chromosome for increasing the activities of the enzymes constituting the operon. Specifically, the method of replacing an expression regulatory sequence of a gene on the operon with a sequence having a stronger activity may be achieved by replacing an endogenous promoter of the acetylase and acetate kinase operon with CJ7 promoter, lysCP1 promoter, EF-Tu promoter, groEL promoter, aceA or aceB promoter, etc., but the replacement is not limited thereto.

As used herein, the term "endogenous activity" refers to an active state of an enzyme in a non-modified state originally possessed by a microorganism, and the term "enhancement compared to its endogenous activity" refers to an increased state of the activity of the enzyme possessed by the microorganism after manipulation, such as the introduction of a gene exhibiting an activity or an increase of the copy number of the corresponding gene, deletion of the inhibition-regulatory factor of the expression of the gene, or modification of the expression regulatory sequence, e.g., use of an improved promoter, compared to the activity possessed by the microorganism before manipulation.

In the present disclosure, the microorganism of the genus Corynebacterium producing putrescine or ornithine, in which an activity of E. coli-derived acetyl-CoA synthetase (acs) may be further introduced therein.

In the present disclosure, acetyl-CoA synthetase (acs) is an enzyme which mediates the reaction for producing acetyl-CoA from ATP, acetic acid, and CoA.

In the present disclosure, the acetyl-CoA synthetase may include, without limitation, the proteins having the amino acid sequence of SEQ ID NO: 9, or any protein having a homology of 70% or higher, specifically 80% or higher, more specifically 90% or higher, even more specifically 95% or higher, yet even more specifically 98% or higher, and most specifically 99% or higher, to the amino acid sequence above, as long as the protein has the substantial activity of mediating the synthesis of acetyl-CoA.

Additionally, since the amino acid sequences of the proteins exhibiting the activities may vary according to the species or strains of a given microorganism, the acetyl-CoA synthetase (acs) in the present disclosure may not be limited to the origin from which it is derived, and for example, it may be from *E. coli*. It is obvious in that any amino acid sequence, which has a homology to the sequence above and has a biological activity substantially the same as or corresponding to the protein of SEQ ID NO: 9, can also belong to the scope of the present disclosure, although the amino acid sequence may have deletion, modification, substitution, or addition, in part of the sequence.

The polynucleotide encoding the acetyl-CoA synthetase (acs) of the present disclosure may include the polynucleotide which encodes a protein including the amino acid sequence of SEQ ID NO: 9, or any protein having a homology of 70% or higher, specifically 80% or higher, more specifically 90% or higher, even more specifically 95% or higher, yet even more specifically 98% or higher, and most specifically 99% or higher, to the above amino acid sequence, and most specifically, it may include the polynucleotide sequence of SEQ ID NO: 10.

The microorganism of the genus *Corynebacterium* of the present disclosure may be a modified microorganism of the genus *Corynebacterium* producing putrescine or ornithine, in which an activity of ornithine decarboxylase (ODC) is further introduced therein.

As used herein, the term "ornithine decarboxylase" refers to an enzyme which produces putrescine by mediating the decarboxylation of ornithine. Although the microorganism of the genus *Corynebacterium* lacks the putrescine biosynthetic enzyme, when ornithine decarboxylase (ODC) is introduced from the outside, putrescine is exported outside the cell as putrescine is being synthesized. The ornithine decarboxylase that can be introduced from the outside can be used in the present disclosure as long as it has the activity above, irrespective of the origin from which the microorganism is derived, and specifically, one from *E. coli* may be introduced.

The microorganism of the genus *Corynebacterium* of the present disclosure may be a modified microorganism of the genus *Corynebacterium* producing putrescine or ornithine, in which, activities of i) ornithine carbamoyltransferase (ArgF), ii) glutamate exporter, or iii) ornithine carbamoyltransferase and glutamate exporter is further weakened, compared to itsr endogenous activity. The glutamate exporter of the genus *Corynebacterium* may be NCgl1221.

The microorganism of the genus *Corynebacterium* of the present disclosure may be a modified microorganism of the genus *Corynebacterium* producing putrescine or ornithine, in which, an activity of at least one selected from the group consisting of acetyl gamma glutamyl phosphate reductase (ArgC), acetylglutamate synthase or ornithine acetyltransferase (ArgJ), acetylglutamate kinase (ArgB), and acetyl ornithine aminotransferase (ArgD) is further enhanced compared to its endogenous activity.

Additionally, the microorganism of the genus *Corynebacterium* may be a modified microorganism of the genus *Corynebacterium* producing putrescine or ornithine, in which, an activity of acetyltransferase, specifically the activity of NCgl1469, is further weakened in comparison with its endogenous activity.

Lastly, the microorganism of the genus *Corynebacterium* may be a modified microorganism of the genus *Corynebacterium* producing putrescine or ornithine, in which an activity of a putrescine exporter, specifically the activity of NCgl2522, is further enhanced compared to its endogenous activity As used herein, "weakening of activity" not only includes the drawing of a lower effect than the original function due to the reduction or inactivation of the activity of a protein itself, but also includes the decrease in its activity by a decrease in the activity of an endogenous gene, activation of regulatory factor(s) for inhibiting gene expression, a decrease in gene copy number, modification of the expression regulatory sequence, and specifically, an inactivation or reduction in enzyme activity due to replacement or modification of a promoter and a mutation within a gene, etc.

Specifically, in the present disclosure, the weakening of activity may be performed by:
1) deleting a part or an entirety of a polynucleotide encoding the protein,
2) modifying an expression regulatory sequence for reducing an expression of the polynucleotide,
3) modifying a polynucleotide sequence on the chromosomes to weaken an activity of the protein, and
4) a selected method from a combination thereof,
but the method is not limited thereto.

Specifically, the method of deleting a part or an entirety of a polynucleotide encoding a protein may be performed by replacing a polynucleotide encoding the endogenous target protein on the chromosome with a polynucleotide having a partial deletion in the polynucleotide sequence or a marker gene using a vector for chromosomal insertion within bacteria. As used herein, the term "a part" may vary depending on the kinds of polynucleotides, but it may specifically refer to 1 to 300, more specifically 1 to 100, and even more specifically 1 to 50.

Additionally, the method of modifying the expression regulatory sequence may be performed by inducing a modification on the expression regulatory sequence through deletion, insertion, non-conservative or conservative substitution of a polynucleotide sequence, or a combination thereof to further weaken the activity of the expression regulatory sequence, or by replacing the polynucleotide sequence with a polynucleotide sequence having a weaker activity. The expression regulatory sequence includes a promoter, an operator sequence, a sequence encoding a ribosome-binding site, and a sequence regulating the termination of transcription and translation.

Additionally, the method of modifying a polynucleotide sequence on the chromosome may be performed by inducing a modification on the sequence through deletion, insertion, non-conservative or conservative substitution of the polynucleotide sequence, or a combination thereof to further weaken the activity of the enzyme, or by replacing the polynucleotide sequence with an improved polynucleotide sequence having a stronger activity.

Additionally, the method of deleting the regulatory factor which inhibits the expression of the polynucleotide of the enzyme may be performed by replacing the polynucleotide for the expression inhibiting factor with a polynucleotide having a partial deletion in the polynucleotide sequence or a marker gene. As used herein, the term "a part" may vary depending on the kinds of polynucleotides, but it may specifically refer to 1 to 300, more specifically 1 to 100, and even more specifically 1 to 50.

In particular, acetyl gamma glutamyl phosphate reductase (ArgC), acetylglutamate synthase or ornithine acetyltransferase (ArgJ), acetylglutamate kinase (ArgB), acetylornithine aminotransferase (ArgD), ornithine carbamoyltransferase (ArgF), proteins involved in the export of glutamate and ornithine decarboxylase (ODC) may respectively include the amino acid sequence of SEQ ID NO: 32, 33, 34, 35, 36, 37, or 38, or any amino acid sequence, which specifically has a homology of 70% or higher, more specifically 80% or higher, and even more specifically 90% or higher, to the above amino acid sequences, although not particularly limited thereto. Additionally, the protein that acetylates putrescine may include an amino acid sequence of SEQ ID NO: 30 or 31, or any amino acid sequence, which specifically has a homology of 70% or higher, more specifically 80% or higher, and even more specifically 90% or higher, to the above amino acid sequences, although the amino acid sequence is not particularly limited thereto.

Additionally, in the present disclosure, the putrescine exporter may include an amino acid sequence of SEQ ID NO: 26 or 28, or any amino acid sequence, which specifically has a homology of 70% or higher, more specifically 80% or higher, and even more specifically 90% or higher, to the above amino acid sequences.

Among the proteins described above, the enhancement of activities of acetyl gamma glutamyl phosphate reductase (ArgC), acetylglutamate synthase or ornithineacetyltransferase (ArgJ), acetylglutamate kinase (ArgB), acetylornithine aminotransferase (ArgD), ornithine decarboxylase (ODC) and putrescine exporter may be achieved, for example, by a method selected from an increase in copy number of the polynucleotides encoding the proteins, modification of the expression regulatory sequence for increasing the expression of the polynucleotides, modification of the polynucleotide sequences on the chromosome for enhancing the activities of the above enzymes, deletion of regulatory factor(s) for inhibiting the expression of the polynucleotides of the above enzymes, or a combination thereof.

Additionally, the weakening of ornithine carbamoyltransferase (ArgF), proteins involved in the export of glutamate, and the proteins that acetylate putrescine may be achieved by a method selected from deletion of a part or the entirety of the polynucleotides encoding the proteins, modification of the expression regulatory sequence to reduce the expression of the polynucleotides, modification of the polynucleotide sequences on the chromosome to weaken the activities of the proteins, and a combination thereof.

Another aspect of the present disclosure provides a method for producing putrescine or ornithine, including:

(i) culturing the microorganism of the genus *Corynebacterium* producing putrescine or ornithine in a medium; and (ii) recovering putrescine or ornithine from the cultured microorganism or the medium.

In the above method, the microorganism may be cultured in batch culture, continuous culture, fed-batch culture, etc., known in the art, although not particularly limited thereto. In particular, regarding the culturing condition, proper pH (i.e., an optimal pH of 5 to 9, specifically pH 6 to 8, and most specifically pH 6.8) can be maintained using a basic compound (e.g., sodium hydroxide, potassium hydroxide, or ammonia) or an acidic compound (e.g., phosphoric acid or sulfuric acid, although not particularly limited thereto. Additionally, an aerobic condition can be maintained by adding oxygen or an oxygen-containing gas mixture to a cell culture. The culture temperature may be maintained at 20° C. to 45° C., and specifically at 25° C. to 40° C., and the microorganism may be cultured for about 10 hours to 160 hours. The putrescine or ornithine produced by the culturing above may be secreted to a culture medium or remain in the cells.

Additionally, in the culture medium, carbon sources, such as sugars and carbohydrates (e.g., glucose, sucrose, lactose, fructose, maltose, molasses, starch, and cellulose), oils and fats (e.g., soybean oil, sunflower seed oil, peanut oil, and coconut oil), fatty acids (e.g., palmitic acid, stearic acid, and linoleic acid), alcohols (e.g., glycerol and ethanol), and organic acids (e.g., acetic acid), may be used individually or in combination, but are not limited thereto; nitrogen sources, such as nitrogen-containing organic compounds (e.g., peptone, yeast extract, meat juice, malt extract, corn steep liquor, soybean flour, and urea), or inorganic compounds (e.g., ammonium sulfate, ammonium chloride, ammonium phosphate, ammonium carbonate, and ammonium nitrate), may be used individually or in combination, but are not limited thereto; and potassium sources, such as potassium dihydrogen phosphate, dipotassium hydrogen phosphate, or sodium-containing salts corresponding thereto, may be used individually or in combination, but are not limited thereto. Additionally, other essential growth-stimulating substances including metal salts (e.g., magnesium sulfate or iron sulfate), amino acids, and vitamins may be further contained in the medium, but are not limited thereto.

The method of recovering the putrescine or ornithine produced during the culturing of the present disclosure may be performed by an appropriate culture method known in the art, for example, such as batch culture, continuous culture, or fed-batch culture, and thereby the target amino acid can be recovered from the culture.

MODE FOR INVENTION

Hereinafter, the present disclosure will be described in more detail with reference to the following Examples. However, these Examples are for illustrative purposes only, and the disclosure is not intended to be limited by these Examples.

Example 1: Introduction of *E. coli*-Derived argA and *E. coli*-Derived argE into a Strain Producing Putrescine and Confirmation of Putrescine-Producing Ability of the Strain 1-1. Preparation of a Strain Simultaneously Introduced with *E. coli*-Derived argA and *E. coli*-Derived argE into a Transposon Gene of ATCC13032-Based Strain Producing Putrescine In order to confirm whether the introduction of the *E. coli*-derived argA gene and the *E. coli*-derived argE gene into an ATCC13032-based strain producing putrescine can improve putrescine-producing ability, argA and argE genes were introduced into the transposon gene of the strain.

As the vector for transformation enabling the introduction of the transposon gene region of a microorganism of the genus *Corynebacterium* within the chromosome, pDZTn (WO 2009/125992) was used, and lysCP1 promoter (International Patent Publication No. WO 2009/096689, SEQ ID NO: 39) was used as the promoter.

Specifically, a primer pair of SEQ ID NOS: 11 and 12 for obtaining the homologous recombinant fragments in the argA ORF region was prepared based on the polynucleotide sequence (SEQ ID NO: 2) of the *E. coli*-derived argA gene, which encodes N-acetylglutamate synthase. Additionally, a primer pair of SEQ ID NOS: 15 and 16 for obtaining the homologous recombinant fragments in the argE ORF region was prepared based on the polynucleotide sequence (SEQ ID NO: 4) of the *E. coli*-derived argE gene, which encodes the acetylornithine deacetylase, and a primer pair of SEQ ID NOS: 13 and 14 for obtaining the homologous recombinant fragments in the lysCP1 region was prepared based on the polynucleotide sequence (SEQ ID NO: 39) of the lysCP1 (Table 1).

TABLE 1

| Primer | Sequence (5'→3') |
|---|---|
| PlysC-argA-F (SEQ ID NO: 11) | GAAAGGTGCACAAAGATGGTAAAGGAACGTAAA ACCG |
| Tn-argA-RXh (SEQ ID NO: 12) | GCCCACTAGTCTCGAGCATGCGGCGTTGATTTT G |
| Tn-PlysC-FXh (SEQ ID NO: 13) | GAATGAGTTCCTCGAGCCGATGCTAGGGCGAAA A |
| PlysC-R (SEQ ID NO: 14) | CTTTGTGCACCTTTCGATCTACGTGCTGACAGT TAC |
| PlysC-argE-F (SEQ ID NO: 15) | GAAAGGTGCACAAAGATGAAAAACAAATTACCG CC |
| Tn-argE-RXh (SEQ ID NO: 16) | GCCCACTAGTCTCGAGGTTTGAGTCACTGTCGG TCG |

First, a gene fragment with a size of about 1.6 kb was amplified using the chromosome of *E. coli* W3110 strain as the template along with a primer pair of SEQ ID NOS: 11 and 12, in order to obrain the argA gene. In particular, PCR was performed by repeating 30 cycles of denaturation at 95° C. for 30 seconds, annealing at 55° C. for 30 seconds, and extension at 72° C. for 1 minute and 30 seconds. The thus-obtained fragments were subjected to electrophoresis in a 0.8% agarose gel, and the bands of desired sizes were eluted and purified.

Additionally, the lysCP1 promoter region was by performing PCR using the chromosome of the KCCM10919P (International Patent Publication No. WO 2009/096689) strain as the template along with a primer pair of SEQ ID NOS: 13 and 14, which was performed by repeating 30 cycles of denaturation at 95° C. for 30 seconds, annealing at 55° C. for 30 seconds, and extension at 72° C. for 30 seconds.

The pDZTn vector was treated with XhoI and then each of the PCR products obtained thereof was subjected to fusion cloning. The fusion cloning was performed using the In-Fusion® HD Cloning Kit (Clontech) and the thus-obtained plasmid was named as pDZTn-lysCP1-argA.

Then, for obtaining the argE gene, PCR products were obtained by amplifying the gene fragment with a size of about 1.4 kb in the same manner as described above, using the chromosome of the *E. coli* W3110 strain as the template along with a primer pair of SEQ ID NOS: 15 and 16, and was subjected to fusion cloning with the lysCP1 promoter region. The thus-obtained plasmid was named as pDZTn-lysCP1-argE.

Then, the plasmid pDZTn-lysCP1-argA was introduced into the KCCM11240P (Korean Patent Application Publication No. 10-2013-0082478) strain by electroporation to obtain transformants, and the transformants were plated on BHIS plate media (Braine heart infusion (37 g/L), sorbitol (91 g/L), and agar (2%)) containing kanamycin (25 μg/mL) and X-gal (5-bromo-4-chloro-3-indolin-D-galactoside) and cultured to form colonies. Among the colonies, blue colonies were selected and thereby the transformed strains introduced with the plasmid pDZTn-lysCP1-argA were selected.

The selected strains were cultured with shaking (30° C., 8 hours) in CM media (glucose (10 g/L), polypeptone (10 g/L), yeast extract (5 g/L), beef extract (5 g/L), NaCl (2.5 g/L), urea (2 g/L), pH 6.8) and sequentially diluted from $10^{-4}$ to $10^{-10}$, plated on solid media containing X-gal, and cultured to form colonies. Among the thus-formed colonies, white colonies which appeared at a relatively low rate were selected and the strain introduced with the argA-encoding gene by a secondary crossover was finally selected. The finally selected strain was subjected to PCR using a primer pair of SEQ ID NOS: 12 and 13 and it was confirmed that the argA-encoding gene was introduced, and the modified strain of *Corynebacterium glutamicum* was named as KCCM11240P Tn:lysCP1-argA.

For the introduction of the strain introduced with argA prepared above, the pDZTn-lysCP1-argE prepared above was transformed into the KCCM11240P Tn:lysCP1-argA in the same manner as described above, and the introduction of argE into the transposon was confirmed in the finally selected strain by performing PCR using a primer pair of SEQ ID NOS: 13 and 16. The thus-selected modified strain of *Corynebacterium glutamicum* was named as KCCM11240P Tn:lysCP1-argA Tn:lysCP1-argE.

1-2. Preparation of a Strain Simultaneously Introduced with *E. coli*-Derived argA and *E. coli*-Derived argE into a Transposon Gene of ATCC13869-Based Strain Producing Putrescine The DAB12-a ΔNCgl1469 (Korean Patent Application Publication No. 10-2013-0082478), which is a *Corynebacterium glutamicum* ATCC13869-based strain producing putrescine, was named as DAB12-b, and argA and argE were introduced into the transposon gene in order to confirm whether the introduction of the *E. coli*-derived argA and *E. coli*-derived argE genes can be associated with the improvement of the putrescine-producing ability of the resulting strain.

First, the pDZTn-lysCP1-argA, which was previously prepared, was transformed into the *Corynebacterium glutamicum* DAB12-b in the same manner as in Example 1-1, and the introduction of argA into the transposon was confirmed. The thus-selected modified strain of *Corynebacterium glutamicum* was named as DAB12-b Tn:lysCP1-argA.

Then, for the introduction of argE into the strain, which is already introduced with argA, the pDZTn-lysCP1-argE, which was previously prepared, was transformed into the DAB12-b Tn:lysCP1-argA in the same manner as in Example 1-1, and the introduction of argE into the transposon was confirmed. The thus-selected modified strain of *Corynebacterium glutamicum* was named as DAB12-b Tn:lysCP1-argE.

1-3. Evaluation of Putrescine-Producing Ability of a *Corynebacterium* Strain Producing Putrescine Introduced with *E. coli*-Derived argA Gene and *E. coli*-Derived argE Gene The putrescine-producing ability was compared among the modified strains of *Corynebacterium glutamicum* prepared in Examples 1-1 and 1-2, in order to confirm the effect of the introduction of the *E. coli*-derived argA and the *E. coli*-derived argE into a strain producing putrescine on putrescin production.

Specifically, two different kinds of modified strains of *Corynebacterium glutamicum*, i.e., (KCCM11240P Tn:lysCP1-argA Tn:lysCP1-argE; DAB12-b Tn:lysCP1-argA Tn:lysCP1-argE) prepared in Examples 1-1 and 1-2, and two different kinds of parent strains (i.e., KCCM11240P and DAB12-b) were respectively plated on 1 mM arginine-containing CM plate media (1% glucose, 1% polypeptone, 0.5% yeast extract, 0.5% beef extract, 0.25% NaCl, 0.2% urea, 100 μL of 50% NaOH, 2% agar, pH 6.8, based on 1 L), and cultured at 30° C. for 24 hours.

Each of the strains cultured therefrom in an amount of about one platinum loop was inoculated into 25 mL of titer media (8% glucose, 0.25% soybean protein, 0.50% corn steep solids, 4% $(NH_4)_2SO_4$, 0.1% $KH_2PO_4$, 0.05% $MgSO_4 \cdot 7H_2O$, 0.15% urea, biotin (100 μg), thiamine HCl (3 mg), calcium-pantothenic acid (3 mg), nicotinamide (3 mg), 5% $CaCO_3$, based on 1 L), and cultured with shaking at 30° C. at a rate of 200 rpm for 98 hours. In all cultures of the strains, 1 mM arginine was added to the media. Upon completion of culture, the concentration of putrescine produced in each culture broth was measured and the results are shown in Table 2 below.

TABLE 2

| Strains | Putrescine (g/L) |
| --- | --- |
| KCCM11240P | 12.2 |
| KCCM11240P Tn:lysCP1-argA Tn:lysCP1-argE | 13.4 |
| DAB12-b | 13.3 |
| DAB12-b Tn:lysCP1-argA Tn:lysCP1-argE | 14.6 |

As shown in Table 2 above, both of the two modified strains of *Corynebacterium glutamicum* simultaneously introduced with *E. coli*-derived argA and *E. coli*-derived argE genes showed an increase of putrescine production by 9.8% or higher.

Example 2: Enhancement of pta-ackA in the Strain Producing Putrescine Introduced with *E. coli*-Derived argA and *E. coli*-Derived argE and Confirmation of Putrescine-Producing Ability of the Strain 2-1. Preparation of a Strain Having a Substitution of the pta-ackA Promoter from an ATCC13032-Based *Corynebacterium* Strain Producing Putrescine The strain producing putrescine introduced with *E. coli*-derived argA and *E. coli*-derived argE genes, prepared in Example 1, was further enhanced in its activity of phosphotransacetylase and acetate kinase (pta-ackA) and the effect of the enhancement on the putrescine-producing ability of the strain was examined.

For this purpose, the promoter of the pta-ackA operon within the chromosome was substituted with a promoter having a stronger activity in comparison with its endogenous promoter, specifically, the lysCP1 promoter (International Patent Publication No. WO 2009/096689) was introduced to the upstream of the initiation codon of the pta-ackA operon.

First, a homologous recombinant fragment, which includes the lysCP1 promoter and both ends of the promoter have the original pta-ackA sequence on the chromosome, was obtained. Specifically, the 5'-end region of the lysCP1 promoter was obtained by performing PCR using the genomic DNA of the *Corynebacterium glutamicum* ATCC13032 along with a primer pair of SEQ ID NOS: 17 and 18. In particular, PCR reaction was performed by repeating 30 cycles of denaturation at 95° C. for 30 seconds, annealing at 55° C. for 30 seconds, and extension at 72° C. for 30 seconds.

Additionally, the lysCP1 promoter region was obtained by performing PCR in the same condition using a primer pair of SEQ ID NOS: 14 and 19, and the 3'-end region of the lysCP1 promoter was obtained by performing PCR using the genomic DNA of the *Corynebacterium glutamicum* ATCC13032 as a template along with a primer pair of SEQ ID NOS: 20 and 21. The primers used in obtaining the lysCP1 promoter are shown in Table 1 above and Table 3 below.

TABLE 3

| Primer | Sequence (5'→3') |
| --- | --- |
| Pro-pta-FX (SEQ ID NO: 17) | CCGGG-GATCCTCTAGAGGGGTTCTAAAAAATGTGGAGT |
| pta-PlysC-R (SEQ ID NO: 18) | GCCGTGCTTTTCGCCCTAGCATCGGA-CATCGCCTTTCTAATTT |
| PlysC-F (SEQ ID NO: 19) | CCGATGCTAGGGCGAAAAGCACGGC |
| PlysC-pta-ackA-F (SEQ ID NO: 20) | GAAAGGTGCACAAA-GATGTCTGACACACCGACCTCAGCTC |
| Pro-pta-RX (SEQ ID NO: 21) | GCAGGTCGACTCTAGATTATCCGGCAT-TGGCTCT |

Each of the PCR products obtained above was subjected to fusion cloning using the pDZ vector treated with XbaI. The fusion cloning was performed using the In-Fusion® HD Cloning Kit (Clontech) and the thus-obtained plasmid was named as pDZ-lysCP1-1'pta-ackA.

The plasmid pDZ-lysCP1-1'pta-ackA prepared from the above was respectively introduced into the KCCM11240P and KCCM11240P Tn:lysCP1-argA Tn:lysCP1-argE strains, which is a modified strain of *Corynebacterium glutamicum* prepared in Example 1-1, by electroporation to obtain transformants, and the transformants were plated on BHIS plate media (Braine heart infusion (37 g/L), sorbitol (91 g/L), and agar (2%)) containing kanamycin (25 μg/mL) and X-gal (5-bromo-4-chloro-3-indolin-D-galactoside) and cultured to form colonies. Among the colonies, blue colonies were selected and thereby the transformed strains introduced with the plasmidpDZ-lysCP1-1'pta-ackA were selected.

The selected strains were cultured with shaking (30° C., 8 hours) in CM media (glucose (10 g/L), polypeptone (10 g/L), yeast extract (5 g/L), beef extract (5 g/L), NaCl (2.5 g/L), urea (2 g/L), pH 6.8) and sequentially diluted from $10^{-4}$ to $10^{-10}$, plated on solid media containing X-gal, and cultured to form colonies. Among the thus-formed colonies, white colonies which appeared at a relatively low rate were selected and the strain, in which the pta-ackA promoter was substituted with the lysCP1 promoter by a secondary crossover, was finally selected.

The finally selected strain was subjected to PCR using a primer pair of SEQ ID NOS: 19 and 21 and was confirmed that the lysCP1 promoter was introduced to the upstream of the initiation codon of pta-ackA within the chromosome. In particular, the PCR reaction was performed by repeating 30 cycles of denaturation at 95° C. for 30 seconds, annealing at 55° C. for 30 seconds, and extension at 72° C. for 1 minute.

The thus-selected modified strains of *Corynebacterium glutamicum* were named as KCCM11240P lysCP1-1'pta-ackA and KCCM11240P Tn:lysCP1-argA Tn:lysCP1-argE lysCP1-1'pta-ackA, respectively.

2-2. Preparation of a Strain Having a Substitution of the pta-ackA Promoter from an ATCC13869-Based *Corynebacterium* Strain Producing Putrescine In order to confirm the sequence of the gene encoding the pta-ackA derived from *Corynebacterium glutamicum* ATCC13869 and the protein expressed therefrom by the method disclosed in Example 2-1, PCR was performed using the genomic DNA of *Corynebacterium glutamicum* ATCC13869 as a template along with a primer pair of SEQ ID NOS: 17 and 22 (Tables 3 and 4). In particular, the PCR reaction was performed by repeating 30 cycles of denaturation at 95° C. for 30 seconds, annealing at 55° C. for 30 seconds, and extension at 72° C. for 3 minutes.

The thus-obtained PCR products were separated by electrophoresis and the sequences were analyzed. As a result, it was confirmed that the gene encoding the pta-ackA derived from *Corynebacterium glutamicum* ATCC13869 includes a polynucleotide sequence described by SEQ ID NO: 8 and that the protein encoded by the gene includes an amino acid sequence described by SEQ ID NO: 7.

On the other hand, as a result of the comparison between the amino acid sequence of pta-ackA derived from *Corynebacterium glutamicum* ATCC13032 (SEQ ID NO: 5) and the amino acid sequence of pta-ackA derived from *Corynebacterium glutamicum* ATCC13869, it was confirmed that they have a sequence homology of 99.4%.

TABLE 4

| Primer | Sequence (5'→3') |
|---|---|
| Pta-ackA-R (SEQ ID NO: 22) | TGCAGTTTCACCCCTTAA |
| 13869_pta-PlysC-R (SEQ ID NO: 23) | GCCGTGCTTTTCGCCCTAGCATCGGACATC GCCTTTCTAGTTT |

First, a homologous recombinant fragment, which includes the lysCP1 promoter and both ends of the promoter have the original pta-ackA sequence on the chromosome, was obtained. Specifically, the 5'-end region of the lysCP1 promoter was obtained by performing PCR using the genomic DNA of the *Corynebacterium glutamicum* ATCC13869 along with a primer pair of SEQ ID NOS: 17 and 23. In particular, PCR reaction was performed by repeating 30 cycles of denaturation at 95° C. for 30 seconds, annealing at 55° C. for 30 seconds, and extension at 72° C. for 30 seconds. Additionally, the lysCP1 promoter region was obtained by performing PCR in the same condition using a primer pair of SEQ ID NOS: 14 and 19, and the 3'-end region of the lysCP1 promoter was obtained by performing PCR using the genomic DNA of the *Corynebacterium glutamicum* ATCC13869 as a template along with a primer pair of SEQ ID NOS: 20 and 21. The primers used in the promoter substitution are shown in Tables 1, 3 and 4.

Each of the PCR products obtained thereof was subjected to fusion cloning using the pDZTn vector treated with XhoI. The fusion cloning was performed using the In-Fusion® HD Cloning Kit (Clontech) and the thus-obtained plasmid was named as pDZ-lysCP1-2'pta-ackA.

The plasmid pDZ-lysCP1-2'pta-ackA prepared from the above was respectively transformed into DAB12-b and DAB12-b Tn:lysCP1-argA Tn:lysCP1-argE, which is a modified strain of *Corynebacterium glutamicum* prepared in Example 1-2, in the same manner as in Example 2-1. As a result, it was confirmed that the lysCP1 promoter was introduced to the upstream of the initiation codon of pta-ackA within the chromosome. The modified strains of *Corynebacterium glutamicum* were named as DAB12-b lysCP1-2'pta-ackA and DAB12-b Tn:lysCP1-argA Tn:lysCP1-argE lysCP1-2'pta-ackA, respectively.

2-3. Evaluation of Putrescine-Producing Ability of a Strain with Enhanced pta-ackA In order to confirm the effect of the enhancement of pta-ackA in a strain producing putrescine introduced with *E. coli*-derived argA and *E. coli*-derived argE, the putrescine-producing ability was compared among the modified strains of *Corynebacterium glutamicum* prepared in Examples 2-1 and 2-2.

Specifically, four kinds of modified strains of *Corynebacterium glutamicum* (KCCM11240P lysCP1-1'pta-ackA; KCCM11240P Tn:lysCP1-argA Tn:lysCP1-argE lysCP1-1'pta-ackA; DAB12-b lysCP1-2'pta-ackA; and DAB12-b Tn:lysCP1-argA Tn:lysCP1-argE lysCP1-2'pta-ackA) and four kinds of parent strains (KCCM11240P; KCCM11240P Tn:lysCP1-argA Tn:lysCP1-argE; DAB12-b; and DAB12-b Tn:lysCP1-argA Tn:lysCP1-argE) were respectively plated on 1 mM arginine-containing CM plate media (1% glucose, 1% polypeptone, 0.5% yeast extract, 0.5% beef extract, 0.25% NaCl, 0.2% urea, 100 μL of 50% NaOH, 2% agar, pH 6.8, based on 1 L), and cultured at 30° C. for 24 hours. Each of the strains cultured therefrom in an amount of about one platinum loop was inoculated into 25 mL of titer media (8% glucose, 0.25% soybean protein, 0.50% corn steep solids, 4% $(NH_4)_2SO_4$, 0.1% $KH_2PO_4$, 0.05% $MgSO_4.7H_2O$, 0.15% urea, biotin (100 μg), thiamine HCl (3 mg), calcium-pantothenic acid (3 mg), nicotinamide (3 mg), 5% $CaCO_3$, based on 1 L), and cultured with shaking at 30° C. at a rate of 200 rpm for 98 hours. In all cultures of the strains, 1 mM arginine was added to the media. Upon completion of culture, the concentration of putrescine produced in each culture broth was measured and the results are shown in Table 5 below.

TABLE 5

| Strains | Putrescine (g/L) |
|---|---|
| KCCM 11240P | 12.2 |
| KCCM 11240P lysCP1-1'pta-ackA | 12.3 |
| KCCM 11240P Tn:lysCP1-argA Tn:lysCP1-argE | 13.4 |
| KCCM 11240P Tn:lysCP1-argA Tn:lysCP1-argE lysCP1-1'pta-ackA | 14.1 |
| DAB12-b | 13.3 |
| DAB12-b lysCP1-2'pta-ackA | 13.4 |
| DAB12-b Tn:lysCP1-argA Tn:lysCP1-argE | 14.6 |
| DAB12-b Tn:lysCP1-argA Tn:lysCP1-argE lysCP1-2'pta-ackA | 15.2 |

As shown in Table 5, when pta-ackA was enhanced in KCCM 11240P and DAB12-b, respectively, the amout of putrescine production was at the same level. However, when pta-ackA was enhanced in the two different kinds of modified strains of *Corynebacterium glutamicum* simultaneously introduced with *E. coli*-derived argA and *E. coli*-derived argE genes (KCCM11240P Tn:lysCP1-argA Tn:lysCP1-argE; DAB12-b Tn:lysCP1-argA Tn:lysCP1-argE), respectively, the amount of putrescine production was increased by 14.3% or higher, compared to the parent strain. Additionally, the amount of putrescine production was increased by 4% or higher, based on the modified strains.

As such, the present inventors named the microorganism of the genus *Corynebacterium* (*Corynebacterium glutamicum* KCCM11240P Tn:lysCP1-argA Tn:lysCP1-argE:lysCP1-1'pta-ackA), which has an improved ability to produce putrescine, prepared from the *Corynebacterium glutamicum* KCCM 11240P strain producing putrescine by introducing the activities of *E. coli*-derived argA and *E. coli*-derived argE and enhancing the activity of pta-ackA to the *Corynebacterium glutamicum* KCCM 11240P strain, as CC01-1145, and deposited in the Korean Culture Center of Microorganisms (KCCM), (Address: Yurim B/D, 45, Hongjenae- 2ga-gil, Seodaemun-gu, SEOUL 120-861, Republic of Korea), on Nov. 21, 2014, with the accession number KCCM11606P under the Budapest Treaty on the International Recognition of the Deposit of Microorganisms for the Purposes of Patent Procedure.

Example 3: Introduction of E. coli-Derived acs into a Strain Producing Putrescine Introduced with E. coli-Derived argA and E. coli-Derived argE and Confirmation of the Putrescine-Producing Ability of the Resulting Strain 3-1. Preparation of a Strain Introduced with E. coli-Derived acs into a Transposon Gene of an ATCC13032-Based Strain Producing Putrescine The acs was introduced into the transposon gene using the lysCP1 promoter in order to confirm whether the introduction of E. coli-derived acetyl-CoA synthetase (acs) gene into an ATCC13032-based strain producing putrescine, which is already introduced with E. coli-derived argA and E. coli-derived argE, can improve the putrescine-producing ability.

Specifically, a primer pair of SEQ ID NOS: 24 and 25 for obtaining the homologous recombinant fragment around the acs ORF region and a primer pair of SEQ ID NOS: 13 and 14 for obtaining the homologous recombinant fragment around the lysCP1 promoter region were prepared as shown in Table 1 above and Table 6 below, based on the polynucleotide sequence described by SEQ ID NO: 10 of the gene encoding the acs.

TABLE 6

| Primer | Sequence (5'→3') |
|---|---|
| PlysC-acs-F (SEQ ID NO: 24) | GAAAGGTGCACAAAGATGAGCCAAATTCACAAA |
| Tn-acs-RXh (SEQ ID NO: 25) | GCCCACTAGTCTCGAGAAGGCGTTTACGCCGCA TCC |

Specifically, for obtaining the acs gene, the gene fragment with a size of about 2 kb was amplified using the chromosome of the E. coli W3110 strain as a template along with a primer pair of SEQ ID NOS: 24 and 25. In particular, PCR reaction was performed by repeating 30 cycles of denaturation at 95° C. for 30 seconds, annealing at 55° C. for 30 seconds, and extension at 72° C. for 1 minute and 30 seconds. Then, the thus-obtained PCR products were subjected to electrophoresis in a 0.8% agarose gel and the bands of desired sizes were eluted and purified.

Additionally, the lysCP1 promoter region was obtained by performing PCR using the chromosome of the KCCM10919P (International Patent Publication No. WO 2009/096689) strain as the template along with a primer pair of SEQ ID NOS: 13 and 14, which was performed by repeating 30 cycles of denaturation at 95° C. for 30 seconds, annealing at 55° C. for 30 seconds, and extension at 72° C. for 30 seconds.

The pDZ vector was treated with XhoI and each of the thus-obtained PCR products was subjected to fusion cloning. The fusion cloning was performed using the InFusion® HD Cloning Kit (Clontech). The thus-obtained plasmid was named as pDZTn-lysCP1-acs.

Then, the plasmid pDZTn-lysCP1-acs was introduced into the KCCM11240P and KCCM11240P Tn:lysCP1-argA Tn:lysCP1-argE, which is a modified strain of Corynebacterium glutamicum prepared in Example 1-1, respectively, by electroporation to obtain transformants, and the transformants were plated on BHIS plate media (Braine heart infusion (37 g/L), sorbitol (91 g/L), and agar (2%)) containing kanamycin (25 µg/mL) and X-gal (5-bromo-4-chloro-3-indolin-D-galactoside) and cultured to form colonies. Among the colonies, blue colonies were selected and thereby the transformed strains introduced with the plasmid pDZTn-lysCP1-acs were selected.

The selected strains were cultured with shaking (30° C., 8 hours) in CM media (glucose (10 g/L), polypeptone (10 g/L), yeast extract (5 g/L), beef extract (5 g/L), NaCl (2.5 g/L), urea (2 g/L), pH 6.8) and sequentially diluted from $10^{-4}$ to $10^{-10}$, plated on solid media containing X-gal, and cultured to form colonies. Among the thus-formed colonies, white colonies which appeared at a relatively low rate were selected and the strains introduced with the acs-encoding gene by a secondary crossover were finally selected. The finally selected strains were subjected to PCR using a primer pair of SEQ ID NOS: 13 and 25 and confirmed that the acs-encoding gene was introduced, and the modified strains of Corynebacterium glutamicum were named as KCCM11240P Tn:lysCP1-acs and KCCM11240P Tn:lysCP1-argA Tn:lysCP1-argE Tn:lysCP1-acs, respectively.

3-2. Preparation of a Strain Introduced with E. coli-Derived acs into a Transposon Gene of ATCC13869-Based Strain Producing Putrescine As in Example 3-1, the pDZTn-lysCP1-acs prepared from the above was transformed into DAB12-b and the DAB12-b Tn:lysCP1-argA Tn:lysCP1-argE, which is a modified strain of Corynebacterium glutamicum prepared in Example 1-2, respectively, in the same manner as in Example 3-1, and it was confirmed that the acs was introduced into the transposon gene.

The thus-selected modified strains of Corynebacterium glutamicum were named as DAB12-b Tn:lysCP1-acs and DAB12-b Tn:lysCP1-argA Tn:lysCP1-argE Tn:lysCP1-acs, respectively.

3-3. Evaluation of Putrescine-Producing Ability of a Strain Introduced with E. coli-Derived acs In order to confirm the effect of the introduction of acs in a strain producing putrescine, which is already introduced with E. coli-derived argA and E. coli-derived argE, putrescine-producing ability was compared among the modified strains of Corynebacterium glutamicum prepared in Examples 3-1 and 3-2.

Specifically, four kinds of modified strains of Corynebacterium glutamicum (KCCM11240P Tn:lysCP1-acs; KCCM11240P Tn:lysCP1-argA Tn:lysCP1-argE Tn:lysCP1-acs; DAB12-b Tn:lysCP1-acs; and DAB12-b Tn:lysCP1-argA Tn:lysCP1-argE Tn:lysCP1-acs) and four kinds of parent strains (KCCM11240P; KCCM11240P Tn:lysCP1-argA Tn:lysCP1-argE; DAB12-b; and DAB12-b Tn:lysCP1-argA Tn:lysCP1-argE) were respectively plated on 1 mM arginine-containing CM plate media (1% glucose, 1% polypeptone, 0.5% yeast extract, 0.5% beef extract, 0.25% NaCl, 0.2% urea, 100 µL of 50% NaOH, 2% agar, pH 6.8, based on 1 L), and cultured at 30° C. for 24 hours. Each of the strains cultured therefrom in an amount of about one platinum loop was inoculated into 25 mL of titer media (8% glucose, 0.25% soybean protein, 0.50% corn steep solids, 4% $(NH_4)_2SO_4$, 0.1% $KH_2PO_4$, 0.05% $MgSO_4.7H_2O$, 0.15% urea, biotin (100 µg), thiamine HCl (3 mg), calcium-pantothenic acid (3 mg), nicotinamide (3 mg), 5% $CaCO_3$, based on 1 L), and cultured with shaking at 30° C. at a rate of 200 rpm for 98 hours. In all cultures of the strains, 1 mM arginine was added to the media. Upon completion of culture, the concentration of putrescine produced in each culture broth was measured and the results are shown in Table 7 below.

TABLE 7

| Strains | Putrescine (g/L) |
| --- | --- |
| KCCM 11240P | 12.2 |
| KCCM 11240P Tn:lysCP1-acs | 12.2 |
| KCCM11240P Tn:lysCP1-argA Tn:lysCP1-argE | 13.4 |
| KCCM11240P Tn:lysCP1-argA Tn:lysCP1-argE Tn:lysCP1-acs | 13.9 |
| DAB12-b | 13.3 |
| DAB12-b Tn:lysCP1-acs | 13.2 |
| DAB12-b Tn:lysCP1-argA Tn:lysCP1-argE | 14.6 |
| DAB12-b Tn:lysCP1-argA Tn:lysCP1-argE Tn:lysCP1-acs | 15.1 |

As shown in Table 7, when acs was introduced into KCCM 11240P and DAB12-b, respectively, the amount of putrescine production was at the same level. However, when acs was introduce in the two different kinds of modified strains of Corynebacterium glutamicum simultaneously introduced with E. coli-derived argA and E. coli-derived argE genes (KCCM11240P Tn:lysCP1-argA Tn:lysCP1-argE; DAB12-b Tn:lysCP1-argA Tn:lysCP1-argE), respectively, the amount of putrescine production was increased by 13.5% or higher, compared to the parent strain. Additionally, the amount of putrescine production was increased by 3.4% or higher, compared to the above modified strains.

Example 4: A Strain Having Introduction of E. coli-Derived argA, E. coli-Derived argE, and Substitution of pta-ackA Promoter from a Strain Producing Putrescine with Improved Putrescine Export Ability, and the Putrescine-Producing Ability of the Strain 4-1. Preparation of a Strain Having Introduction of E. coli-Derived argA, -argE and Substitution of pta-ackA Promoter from a Strain Having Improved Putrescine Export Ability A strain was prepared to examine whether the introduction of E. coli-derived argA and E. coli-derived argE and the enhancement of the activity of the Corynebacterium pta-ackA can improve the putrescine-producing ability, based on the KCCM11401P (Korean Patent Application Publication No. 10-2014-0115244) strain with improved putrescine export ability.

Specifically, the pDZTn-lysCP1-argA prepared in Example 1-1 was transformed into the KCCM11401P in the same manner as in Example 1-1, and as a result, it was confirmed that argA was introduced into the transposon gene. The thus-selected modified strain of Corynebacterium glutamicum was named as KCCM11401P Tn:lysCP1-argA.

Additionally, for introducing argE into the strain, which is already introduced with argA as prepared in Example 1-1, the pDZTn-lysCP1-argE prepared in Example 1-1 was transformed into the KCCM11401P Tn:lysCP1-argA in the same manner as in Example 1-1 and it was confirmed that argE was introduced into the transposon gene. The thus-selected modified strain was named as KCCM11401P Tn:lysCP1-argA Tn:lysCP1-argE.

Then, the pDZ-lysCP1-1'pta-ackA prepared in Example 2-1 was transformed into the KCCM11401P Tn: lysCP1-argA Tn:lysCP1-argE in the same manner as in Example 2-1, and it was confirmed that the lysCP1 promoter was introduced to the upstream of the initiation codon of pta-ackA within the chromosome. The above modified strain of Corynebacterium glutamicum was named as KCCM11401P Tn:lysCP1-argA Tn:lysCP1-argE lysCP1-1'pta-ackA.

4-2. Evaluation of a Strain Having Introduction of E. coli-Derived argA, E. coli-Derived argE and Substitution of pta-ackA Promoter from a Strain Having Improved Putrescine Export Ability In order to confirm the effect of the introduction of E. coli-derived argA and E. coli-derived argE and the enhancement of pta-ackA activity on a strain of Corynebacterium glutamicum producing putrescine with improved putrescine export ability, the putrescine-producing ability was compared among the modified strains of Corynebacterium glutamicum prepared in Example 4-1.

Specifically, the modified strains of Corynebacterium glutamicum (KCCM11401P Tn:lysCP1-argA Tn:lysCP1-argE, KCCM11401P Tn:lysCP1-argA Tn:lysCP1-argE lysCP1-1'pta-ackA) and the parent strain (KCCM11401P) were respectively plated on 1 mM arginine-containing CM plate media (1% glucose, 1% polypeptone, 0.5% yeast extract, 0.5% beef extract, 0.25% NaCl, 0.2% urea, 100 µL of 50% NaOH, 2% agar, pH 6.8, based on 1 L), and cultured at 30° C. for 24 hours. Each of the strains cultured therefrom in an amount of about one platinum loop was inoculated into 25 mL of titer media (8% glucose, 0.25% soybean protein, 0.50% corn steep solids, 4% $(NH_4)_2SO_4$, 0.1% $KH_2PO_4$, 0.05% $MgSO_4 \cdot 7H_2O$, 0.15% urea, biotin (100 µg), thiamine HCl (3 mg), calcium-pantothenic acid (3 mg), nicotinamide (3 mg), 5% $CaCO_3$, based on 1 L), and cultured with shaking at 30° C. at a rate of 200 rpm for 98 hours. In all cultures of the strains, 1 mM arginine was added to the media. Upon completion of culture, the concentration of putrescine produced in each culture broth was measured and the results are shown in Table 8 below.

TABLE 8

| Strains | Putrescine (g/L) |
| --- | --- |
| KCCM11401P | 11.8 |
| KCCM11401P Tn:lysCP1-argA Tn:lysCP1-argE | 13.2 |
| KCCM11401P Tn:lysCP1-argA Tn:lysCP1-argE lysCP1-1'pta-ackA | 13.7 |

As shown in Table 8, it was confirmed that when the KCCM11401P having enhanced putrescine export ability was introduced with E. coli-derived argA gene and E. coli-derived argE gene, the amount of putrescine production was increased by 11.9% compared to that of the partent strain, and when the strain was further enhanced with pta-ackA, the amount of putrescine production was increased by 16.1% compared to that of the partent strain.

Example 5: Introduction of E. coli-Derived argA and E. coli-Derived argE in a Strain Producing Ornithine and Confirmation of the Ornithine-Producing Ability of the Strain 5-1. Preparation of a Strain Simultaneously Introduced with E. coli-Derived argA and E. coli-Derived argE into a Transposon Gene of KCCM11137P-Based Strain Producing Ornithine In order to confirm whether the introduction of E. coli-derived argA gene and E. coli-derived argE gene into the KCCM11137P (Korean Patent Application Publication No. 10-1372635) strain, which is a Corynebacterium glutamicum ATCC13032-based strain producing ornithine, can improve ornithine-producing ability, argA gene and argE gene were introduced into a transposon gene of the strain using the vector prepared in Example 1-1.

First, the plasmid pDZTn-lysCP1-argA was introduced into the KCCM11137P strain by electroporation to obtain transformants, and the transformants were plated on BHIS plate media (Braine heart infusion (37 g/L), sorbitol (91 g/L), and agar (2%)) containing kanamycin (25 μg/mL) and X-gal (5-bromo-4-chloro-3-indolin-D-galactoside) and cultured to form colonies. Among the colonies, blue colonies were selected and thereby the strains introduced with the plasmid pDZTn-lysCP1-argA were selected.

The selected strains were cultured with shaking (30° C., 8 hours) in CM media (glucose (10 g/L), polypeptone (10 g/L), yeast extract (5 g/L), beef extract (5 g/L), NaCl (2.5 g/L), urea (2 g/L), pH 6.8) and sequentially diluted from $10^{-4}$ to $10^{-10}$, plated on solid media containing X-gal, and cultured to form colonies. Among the thus-formed colonies, white colonies which appeared at a relatively low rate were selected and the strain introduced with the argA-encoding gene by a secondary crossover was finally selected. The finally selected strain was subjected to PCR using a primer pair of SEQ ID NOS: 12 and 13 and confirmed that the argA-encoding gene was introduced, and the modified strain of *Corynebacterium glutamicum* was named as KCCM11137P Tn:lysCP1-argA.

For the introduction of argE into the strain, which is already introduced with argA as prepared above, the pDZTn-lysCP1-argE prepared in Example 1-1 was transformed into the KCCM11137P Tn:lysCP1-argA in the same manner as in Example 1-1, and thereby it was confirmed that the argE was introduced within the transposon gene.

The thus-selected modified strain of *Corynebacterium glutamicum* was named as KCCM11137P Tn:lysCP1-argA Tn:lysCP1-argE.

5-2. Evaluation of Ornithine-Producing Ability of a *Corynebacterium* Strain Producing Ornithine Introduced with *E. coli*-Derived argA and *E. coli*-Derived argE In order to confirm the effect of the introduction of *E. coli*-derived argA and *E. coli*-derived argE on ornithine production in a strain producing ornithine, the ornithine-producing ability was compared among the modified strains of *Corynebacterium glutamicum* prepared in Example 5-1.

Specifically, one kind of a modified strain of *Corynebacterium glutamicum* (KCCM11137P Tn:lysCP1-argA Tn:lysCP1-argE) and one kind of a parent strain (KCCM11137P) were respectively plated on 1 mM arginine-containing CM plate media (1% glucose, 1% polypeptone, 0.5% yeast extract, 0.5% beef extract, 0.25% NaCl, 0.2% urea, 100 μL of 50% NaOH, 2% agar, pH 6.8, based on 1 L), and cultured at 30° C. for 24 hours. Each of the strains cultured therefrom in an amount of about one platinum loop was inoculated into 25 mL of titer media (8% glucose, 0.25% soybean protein, 0.50% corn steep solids, 4% $(NH_4)_2SO_4$, 0.1% $KH_2PO_4$, 0.05% $MgSO_4 \cdot 7H_2O$, 0.15% urea, biotin (100 μg), thiamine HCl (3 mg), calcium-pantothenic acid (3 mg), nicotinamide (3 mg), 5% $CaCO_3$, based on 1 L), and cultured with shaking at 30° C. at a rate of 200 rpm for 98 hours. In all cultures of the strains, 1 mM arginine was added to the media. Upon completion of culture, the concentration of putrescine produced in each culture broth was measured and the results are shown in Table 9 below.

TABLE 9

| Strains | Ornithine (g/L) |
|---|---|
| KCCM11137P | 7.8 |
| KCCM11137P Tn:lysCP1-argA Tn:lysCP1-argE | 8.9 |

As shown in Table 9, it was confirmed that when the modified strain of *Corynebacterium glutamicum* introduced with *E. coli*-derived argA gene and *E. coli*-derived argE gene showed an increase in the amount of ornithine production by 14.1% compared to that of the parent strain.

Example 6: Enhancement of pta-ackA in a Strain Introduced with *E. coli*-Derived argA and *E. coli*-Derived argE and Confirmation of Ornithine-Producing Ability of the Strain 6-1. Preparation of a Strain Having a Substitution of pta-ackA Promoter from an ATCC13032-Based Strain Producing Ornithine In order to confirm whether the enhancement of pta-ackA activity into the ATCC13032-based strain producing ornithine introduced with *E. coli*-derived argA and *E. coli*-derived argE can improve the ornithine-producing ability, the lysCP1 promoter (WO 2009/096689) was introduced to the upstream of the initiation codon of pta-ackA operon within the chromosome.

First, the plasmid pDZ-lysCP1-1'pta-ackA prepared in Example 2-1 was introduced into KCCM11137P and KCCM11137P Tn:lysCP1-argA Tn:lysCP1-argE strains, respectively, by electroporation to obtain transformants and the transformants were plated on BHIS plate media (Braine heart infusion (37 g/L), sorbitol (91 g/L), and agar (2%)) containing kanamycin (25 μg/mL) and X-gal (5-bromo-4-chloro-3-indolin-D-galactoside) and cultured to form colonies. Among the colonies, blue colonies were selected and thereby the transformed strains introduced with the plasmid pDZ-lysCP1-1'pta-ackA were selected.

The selected strains were cultured with shaking (30° C., 8 hours) in CM media (glucose (10 g/L), polypeptone (10 g/L), yeast extract (5 g/L), beef extract (5 g/L), NaCl (2.5 g/L), urea (2 g/L), pH 6.8) and sequentially diluted from $10^{-4}$ to $10^{-10}$, plated on solid media containing X-gal, and cultured to form colonies. Among the thus-formed colonies, white colonies which appeared at a relatively low rate were selected and the strain, in which the pta-ackA promoter was substituted with the lysCP1 promoter by a secondary crossover, was finally selected. The finally selected strain was subjected to PCR using a primer pair of SEQ ID NOS: 19 and 21 and confirmed that the lysCP1 promoter was introduced to the upstream of the initiation codon of pta-ackA operon within the chromosome. In particular, PCR reaction was performed by repeating 30 cycles of denaturation at 95° C. for 30 seconds, annealing at 55° C. for 30 seconds, and extension at 72° C. for 1 minute.

The thus-selected modified strains of *Corynebacterium glutamicum* were named as KCCM11137P lysCP1-1'pta-ackA and KCCM11137P Tn:lysCP1-argA Tn:lysCP1-argE lysCP1-1'pta-ackA, respectively.

6-2. Evaluation of Ornithine-Producing Ability of a Strain with Enhanced pta-ackA Activity In order to confirm the effect of the enhancement of pta-ackA activity on a strain producing ornithine introduced with *E. coli*-derived argA and *E. coli*-derived argE, the ornithine-producing ability was compared among the modified strains of *Corynebacterium glutamicum* prepared in Example 6-1.

Specifically, two different kinds of modified strains of *Corynebacterium glutamicum*, (KCCM11137P lysCP1-1'pta-ackA; KCCM11137P Tn:lysCP1-argA Tn:lysCP1-argE lysCP1-1'pta-ackA) and two different kinds of parent strains (KCCM11137P; KCCM11137P Tn:lysCP1-argA Tn:lysCP1-argE) were respectively plated on 1 mM arginine-containing CM plate media (1% glucose, 1% polypeptone, 0.5% yeast extract, 0.5% beef extract, 0.25% NaCl, 0.2% urea, 100 µL of 50% NaOH, 2% agar, pH 6.8, based on 1 L), and cultured at 30° C. for 24 hours. Each of the strains cultured therefrom in an amount of about one platinum loop was inoculated into 25 mL of titer media (8% glucose, 0.25% soybean protein, 0.50% corn steep solids, 4% $(NH_4)_2SO_4$, 0.1% $KH_2PO_4$, 0.05% $MgSO_4.7H_2O$, 0.15% urea, biotin (100 µg), thiamine HCl (3 mg), calcium-pantothenic acid (3 mg), nicotinamide (3 mg), 5% $CaCO_3$, based on 1 L), and cultured with shaking at 30° C. at a rate of 200 rpm for 98 hours. In all cultures of the strains, 1 mM arginine was added to the media. Upon completion of culture, the concentration of ornithine produced in each culture broth was measured and the results are shown in Table 10 below.

TABLE 10

| Strains | Ornithine (g/L) |
| --- | --- |
| KCCM11137P | 7.8 |
| KCCM11137P lysCP1-1'pta-ackA | 7.7 |
| KCCM11137P Tn:lysCP1-argA Tn:lysCP1-argE | 8.9 |
| KCCM11137P Tn:lysCP1-argA Tn:lysCP1-argE lysCP1-1'pta-ackA | 9.4 |

As shown in Table 10, it was confirmed that when the KCCM11137P strain was enhanced with the pta-ackA activity, the amount of ornithine production was not increased, whereas when the KCCM11137P Tn:lysCP1-argA Tn:lysCP1-argE strain, which is the modified strain of *Corynebacterium glutamicum* simultaneously introduced with *E. coli*-derived argA gene and *E. coli*-derived argE gene, the amount of ornithine production was increased by 20.5% compared to that of the KCCM11137P strain, and also increased by 5.6% compared to the KCCM11137P Tn:lysCP1-argA Tn:lysCP1-argE strain.

Example 7: Introduction of *E. coli*-Derived acs in a Strain Introduced with *E. coli*-Derived argA and *E. coli*-Derived argE and Confirmation of Ornithine-Producing Ability of the Strain 7-1. Preparation of a Strain Introduced with *E. coli*-Derived acs into a Transposon Gene from KCCM11137-Based Strain Producing Ornithine The acs was introduced into the transposon gene using the lysCP1 promoter in order to confirm whether the introduction of *E. coli*-derived acs into the KCCM11137P (Korean Patent No. 10-1372635) strain, which is a *Corynebacterium glutamicum* ATCC13032-based strain producing ornithine, can improve the ornithine-producing ability.

First, the plasmid pDZTn-lysCP1-acs prepared in Example 3-1 was introduced into KCCM11137P and KCCM11137P Tn:lysCP1-argA Tn:lysCP1-argE strains, respectively, by electroporation to obtain transformants, and the transformants were plated on BHIS plate media (Braine heart infusion (37 g/L), sorbitol (91 g/L), and agar (2%)) containing kanamycin (25 µg/mL) and X-gal (5-bromo-4-chloro-3-indolin-D-galactoside) and cultured to form colonies. Among the colonies, blue colonies were selected and thereby the transformed strains introduced with the plasmid pDZTn-lysCP1-acs were selected.

The selected strains were cultured with shaking (30° C., 8 hours) in CM media (glucose (10 g/L), polypeptone (10 g/L), yeast extract (5 g/L), beef extract (5 g/L), NaCl (2.5 g/L), urea (2 g/L), pH 6.8) and sequentially diluted from $10^{-4}$ to $10^{-10}$, plated on solid media containing X-gal, and cultured to form colonies. Among the thus-formed colonies, white colonies which appeared at a relatively low rate were selected and the strain introduced with acs-encoding gene by a secondary crossover was finally selected.

The finally selected strains were subjected to PCR using a primer pair of SEQ ID NOS: 13 and 25 and confirmed that the acs-encoding gene was introduced. The thus-selected modified strains of *Corynebacterium glutamicum* were named as KCCM11137P Tn:lysCP1-acs and KCCM11137P Tn:lysCP1-argA Tn:lysCP1-argE Tn:lysCP1-acs, respectively.

7-2. Evaluation of Ornithine-Producing Ability of a Strain Introduced with *E. coli*-Derived acs In order to confirm the effect of the introduction of acs on a strain producing ornithine introduced with *E. coli*-derived argA and *E. coli*-derived argE, the ornithine-producing ability was compared among the modified strains of *Corynebacterium glutamicum* prepared in Example 7-1.

Specifically, two different kinds of modified strains of *Corynebacterium glutamicum*, (KCCM11137P Tn:lysCP1-acs; KCCM11137P Tn:lysCP1-argA Tn:lysCP1-argE Tn:lysCP1-acs) and two different kinds of parent strains (KCCM11137P; KCCM11137P Tn:lysCP1-argA Tn:lysCP1-argE) were respectively plated on 1 mM arginine-containing CM plate media (1% glucose, 1% polypeptone, 0.5% yeast extract, 0.5% beef extract, 0.25% NaCl, 0.2% urea, 100 µL of 50% NaOH, 2% agar, pH 6.8, based on 1 L), and cultured at 30° C. for 24 hours. Each of the strains cultured therefrom in an amount of about one platinum loop was inoculated into 25 mL of titer media (8% glucose, 0.25% soybean protein, 0.50% corn steep solids, 4% $(NH_4)_2SO_4$, 0.1% $KH_2PO_4$, 0.05% $MgSO_4.7H_2O$, 0.15% urea, biotin (100 µg), thiamine HCl (3 mg), calcium-pantothenic acid (3 mg), nicotinamide (3 mg), 5% $CaCO_3$, based on 1 L), and cultured with shaking at 30° C. at a rate of 200 rpm for 98 hours. In all cultures of the strains, 1 mM arginine was added to the media. Upon completion of culture, the concentration of ornithine produced in each culture broth was measured and the results are shown in Table 11 below.

TABLE 11

| Strains | Ornithine (g/L) |
| --- | --- |
| KCCM11137P | 7.8 |
| KCCM11137P Tn:lysCP1-acs | 7.8 |
| KCCM11137P Tn:lysCP1-argA Tn:lysCP1-argE | 8.9 |
| KCCM11137P Tn:lysCP1-argA Tn:lysCP1-argE Tn:lysCP1-acs | 9.2 |

As shown in Table 11, it was confirmed that when the KCCM11137P strain was introduced with acs, the amount of ornithine production was not increased, whereas when the KCCM11137P Tn:lysCP1-argA Tn:lysCP1-argE strain, which is the modified strain of *Corynebacterium glutamicum* simultaneously introduced with *E. coli*-derived argA gene and *E. coli*-derived argE gene, the amount of ornithine production was increased by 17.9% compared to that of the KCCM11137P strain, and also increased by 3.4% compared to the KCCM11137P Tn:lysCP1-argA Tn:lysCP1-argE strain.

Summarizing the foregoing, it was confirmed that the introduction of *E. coli*-derived argA and *E. coli*-derived argE into a strain of *Corynebacterium* can increase the amount of putrescine- and ornithine production, and additionally, it was confirmed that the enhancement of the activity of pta-ackA gene within a strain of *Corynebacterium* or the introduction of *E. coli*-derived acs can further increase the amount of putrescine- and ornithine production.

From the foregoing, a skilled person in the art to which the present invention pertains will be able to understand that the present invention may be embodied in other specific forms without modifying the technical concepts or essential characteristics of the present invention. In this regard, the exemplary embodiments disclosed herein are only for illustrative purposes and should not be construed as limiting the scope of the present invention. On the contrary, the present invention is intended to cover not only the exemplary embodiments but also various alternatives, modifications, equivalents and other embodiments that may be included within the spirit and scope of the present invention as defined by the appended claims.

The invention claimed is:

1. A modified microorganism of the genus *Corynebacterium* having enhanced production of ornithine, wherein the activities of N-acetylglutamate synthase from *E. coli* and acetylornithine deacetylase from *E. coli* are introduced.

2. The modified microorganism according to claim 1, wherein the N-acetylglutamate synthase from *E. coli* consists of the amino acid sequence of SEQ ID NO: 1.

3. The modified microorganism according to claim 1, wherein the microorganism of the genus *Corynebacterium* is *Corynebacterium glutamicum*.

4. The modified microorganism according to claim 1, wherein the activity of i) an ornithine carbamoyltransferase (ArgF), ii) a glutamate exporter, or iii) an ornithine carbamoyltransferase and a glutamate exporter is further weakened compared to its endogenous activity.

5. The modified microorganism according to claim 1, wherein the activity of at least one selected from the group consisting of an acetyl gamma glutamyl phosphate reductase (ArgC), an acetylglutamate synthase/ornithine acetyltransferase (ArgJ), an acetylglutamate kinase (ArgB), and an acetyl ornithine aminotransferase (ArgD) is further enhanced compared to its endogenous activity.

6. The modified microorganism according to claim 1, wherein the activity of an acetyltransferase is further weakened compared to its endogenous activity.

7. The modified microorganism according to claim 6, wherein the acetyltransferase consists of the amino acid sequence of SEQ ID NO: 30 or SEQ ID NO: 31.

8. The modified microorganism according to claim 1, wherein an activity of putrescine exporter is further enhanced compared to its endogenous activity.

9. The modified microorganism according to claim 8, wherein the putrescine exporter consists of the amino acid sequence of SEQ ID NO: 26 or SEQ ID NO: 28.

* * * * *